US010011650B2

(12) United States Patent
Hershberg et al.

(10) Patent No.: US 10,011,650 B2
(45) Date of Patent: Jul. 3, 2018

(54) COMPOSITIONS AND METHODS FOR THE THERAPY AND DIAGNOSIS OF INFLAMMATORY BOWEL DISEASE

(71) Applicant: CORIXA CORPORATION, Seattle, WA (US)

(72) Inventors: Robert Hershberg, Seattle, WA (US); Nancy Ann Hosken, Seattle, WA (US); Michael J. Lodes, Seattle, WA (US); Raodoh Mohamath, Seattle, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 15/868,734

(22) Filed: Jan. 11, 2018

(65) Prior Publication Data

US 2018/0142001 A1 May 24, 2018

Related U.S. Application Data

(60) Division of application No. 15/047,547, filed on Feb. 18, 2016, now Pat. No. 9,868,779, which is a continuation of application No. 12/036,588, filed on Feb. 25, 2008, now Pat. No. 9,290,543, which is a division of application No. 10/449,857, filed on May 30, 2003, now Pat. No. 7,361,733, which is a continuation-in-part of application No. PCT/US02/40422, filed on Dec. 16, 2002.

(60) Provisional application No. 60/426,835, filed on Nov. 15, 2002, provisional application No. 60/396,242, filed on Jul. 16, 2002, provisional application No. 60/341,830, filed on Dec. 17, 2001.

(51) Int. Cl.

| | |
|---|---|
| ***C07K 16/12*** | (2006.01) |
| ***A61K 39/395*** | (2006.01) |
| ***C07K 14/195*** | (2006.01) |
| ***C07K 14/205*** | (2006.01) |
| ***G01N 33/50*** | (2006.01) |
| ***G01N 33/68*** | (2006.01) |
| ***C07K 14/00*** | (2006.01) |
| ***A61K 39/40*** | (2006.01) |
| ***A61K 45/06*** | (2006.01) |
| *A61K 39/00* | (2006.01) |
| *A61K 38/00* | (2006.01) |

(52) U.S. Cl.

CPC .......... *C07K 16/1232* (2013.01); *A61K 39/40* (2013.01); *A61K 45/06* (2013.01); *C07K 14/001* (2013.01); *C07K 14/195* (2013.01); *C07K 14/205* (2013.01); *G01N 33/505* (2013.01); *G01N 33/6893* (2013.01); *A61K 38/00* (2013.01); *A61K 39/00* (2013.01); *A61K 2039/505* (2013.01); *A61K 2039/523* (2013.01); *A61K 2039/53* (2013.01); *C07K 2317/21* (2013.01); *C07K 2317/24* (2013.01); *C07K 2317/76* (2013.01); *C07K 2319/00* (2013.01); *G01N 2800/065* (2013.01)

(58) Field of Classification Search

CPC .......................... C07K 16/1232; A61K 39/395

See application file for complete search history.

(56) References Cited

U.S. PATENT DOCUMENTS

| | | | |
|---|---|---|---|
| 6,248,562 | B1 | 6/2001 | Dunn et al. |
| 7,361,733 | B2 | 4/2008 | Hershberg et al. |
| 8,318,901 | B2 | 11/2012 | Hershberg et al. |
| 9,175,046 | B2 | 11/2015 | Hershberg et al. |
| 9,290,543 | B2 | 3/2016 | Hershberg et al. |
| 9,868,779 | B2 | 1/2018 | Hershberg et al. |
| 2004/0043931 | A1 | 3/2004 | Hersberg et al. |
| 2009/0142778 | A1 | 6/2009 | Hershberg et al. |
| 2012/0039924 | A1 | 2/2012 | Hershberg et al. |
| 2013/0231293 | A1 | 9/2013 | Hershberg et al. |
| 2016/0362481 | A1 | 12/2016 | Hershberg et al. |

FOREIGN PATENT DOCUMENTS

| | | | |
|---|---|---|---|
| EP | 1 285 271 | B1 | 2/2003 |
| JP | 05-166483 | A | 2/1993 |
| WO | 2004/048600 | A2 | 8/2004 |

OTHER PUBLICATIONS

Caradonna, L. et al, "Enteric bacteria, lipopolysaccharides and related cytokines in inflammatory bowel disease: biological and clinical significance," Journal of Endotoxin Research, 2000, vol. 6, No. 3, pp. 205-214.

Chamberlin, W. et al, "Review article: *Mycobacterium avium* subsp. *paratuberculosis* as one cause of Crohn's disease," Aliment. Pharmacol. Ther., 2001, 15:337-346.

Database: Genseq: "Fla gene of Borrelia burgdorferi," EBI accession No. GSN:AAQ27078, 1993, 2 pages.

Database: Geneseq: "Clostridium chauvoei blackleg microbe flagellin gene," EBI accession No. GSN:AAX00225, 1999, 2 pages.

(Continued)

*Primary Examiner* — Ruixiang Li

(74) *Attorney, Agent, or Firm* — Kilpatrick Townsend & Stockton LLP

(57) ABSTRACT

Compositions and methods for the therapy and diagnosis of Inflammatory Bowel Disease (IBD), including Crohn's Disease and Ulcerative Colitis, are disclosed. Illustrative compositions comprise one or more bacterial polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention and/or treatment of IBD.

13 Claims, 7 Drawing Sheets

(56) References Cited

OTHER PUBLICATIONS

Gewirtz, A. et al., "Cutting edge: Bacterial flagellin activates basolaterally expressed tlr5 to induce epithelial proinflammatory gene expression," Journal of Immunology, Aug. 2001, vol. 167, pp. 1882-1885.

Gewrtz, A. et al., "*Salmonella typhimurium* translocates flagellin across intestinal epithelia, inducing a proinflammatory response," Journal of Clinical Investigation, Jan. 2001, vol. 107, pp. 99-109.

Kalmokoff et al., GenEmbl, Accession No. AF026812, Nov. 3, 1997.

Kalmokoff, M. et al, "Biochemical and Genetic characterization of the flagellar filaments from the rumen anaerobe Butyrivibrio fibrisolvens OR77," Anaerobe, 2000, vol. 6, No. 2, pp. 93-109.

Kojima et al., "Rapid detection and identification of Clostridium chauvoei by PCR based on flagellin gene sequence," Veterinary Microbiology, 2001, vol. 78, pp. 363-371.

Lodes, M., "Bacterial flagellin is a dominant antigen in Crohn disease," Journal of Clinical Investigation; May 2004; 1296-1306; vol. 113.

McSorley, S. et al., "Bacterial Flagellin is an effective adjuvant for $CD4^{+}T$ Cells in vivo," Journal of Immunology, Oct. 2002, vol. 169, pp. 3914-3919.

Papadakis, K. et al., "Anti-flagellin (CBirl) Phenotypic and genetic Crohn's disease associations," Inflammatory Bowel Diseases, 2007, vol. 13, No. 5, pp. 524-530.

Targan, S.R. et al., "Antibodies to a Novel flagellin (CBir1) Define a unique serologic response in Crohn's disease (CD)," AGA Abstracts, Apr. 2004, vol. 126, No. 4 Suppl. 2, p. A-113, Abstract No. 817.

Targan, S.R. et al., "Antibodies to CBir1 Flagellin define a unique response that is associated independently with complicated Crohn's disease," Gastroenterology, Jun. 2005, vol. 128, vol. 7, pp. 2020-2028.

COMPOSITIONS AND METHODS FOR THE THERAPY AND DIAGNOSIS OF INFLAMMATORY BOWEL DISEASE

CROSS REFERENCE TO RELATED APPLICATIONS

This application is a divisional of U.S. patent application Ser. No. 15/047,547, filed on Feb. 18, 2016; which application is a continuation of U.S. application Ser. No. 12/036,588, filed on Feb. 25, 2008, which issued on Mar. 22, 2016 as U.S. Pat. No. 9,290,543; which is a divisional application of U.S. patent application Ser. No. 10/449,857, filed May 30, 2003, which issued Apr. 22, 2008 as U.S. Pat. No. 7,361,733; which is a continuation-in-part of PCT Application No. PCT/US02/40422, filed on Dec. 16, 2002; which claims the benefit of U.S. Provisional Patent Application No. 60/426,835, filed Nov. 15, 2002; 60/396,242, filed Jul. 16, 2002; and 60/341,830, filed Dec. 17, 2001, which are all incorporated herein in their entireties.

BACKGROUND OF THE INVENTION

Field of the Invention

The present invention relates generally to therapy and diagnosis of Crohn's Disease and Ulcerative Colitis (collectively referred to as Inflammatory Bowel Disease, or IBD). The invention is more particularly related to polypeptides comprising at least a portion of a protein that is recognized, and to which individuals with IBD mount an aberrant immune response, and to polynucleotides encoding such polypeptides. Such polypeptides and polynucleotides are useful in pharmaceutical compositions, e.g., vaccines, and other compositions for the diagnosis and treatment of IBD.

Description of the Related Art

Crohn's Disease and Ulcerative Colitis (collectively referred to as Inflammatory Bowel Disease or IBD) are chronic, inflammatory diseases of the gastrointestinal tract. While the clinical features vary somewhat between these two disorders, both are characterized by abdominal pain, diarrhea (often bloody), a variable group of 'extra-intestinal' manifestations (such as arthritis, uveitis, skin changes, etc) and the accumulation of inflammatory cells within the small intestine and colon (observed in pathologic biopsy or surgical specimens).

IBD affects both children and adults, and has a bimodal age distribution (one peak around 20, and a second around 40). IBD is a chronic, lifelong disease, and is often grouped with other so-called "autoimmune" disorders (e.g. rheumatoid arthritis, type I diabetes mellitus, multiple sclerosis, etc). IBD is found almost exclusively in the industrialized world. The most recent data from the Mayo Clinic suggest an overall incidence greater than 1 in 100,000 people in the United States, with prevalence data in some studies greater than 1 in 1000. There is a clear trend towards the increasing incidence of IBD in the US and Europe, particularly Crohn's Disease. The basis for this increase is not presently clear. As such, IBD represents the $2^{nd}$ most common autoimmune disease in the United States (after rheumatoid arthritis).

Treatment of IBD is varied. First line therapy typically includes salicylate derivatives (e.g. 5-ASA) given orally or rectally. Response rates in uncomplicated Crohn's Disease are approximately 40% (compared to 20% for placebo). Corticosteroids remain a mainstay in the treatment of patients with more "refractory" disease, despite the untoward side-effects. Newer treatment options include anti-metabolites (e.g. methotrexate, 6-mercaptopurine) and immunomodulators (e.g. Remicade—a chimeric human antibody directed at the TNFα receptor).

In spite of considerable research into therapies for these disorders, IBD remains difficult to diagnose and treat effectively. Furthermore, there are no clear laboratory tests that are diagnostic for IBD, nor are there suitable laboratory tests that serve as "surrogate marker" that are uniformly useful to follow the course of disease in patients. Accordingly, there is a need in the art for improved methods for detecting and treating such inflammatory bowel diseases. The present invention fulfills these needs and further provides other related advantages.

BRIEF SUMMARY OF THE INVENTION

Figure 1:
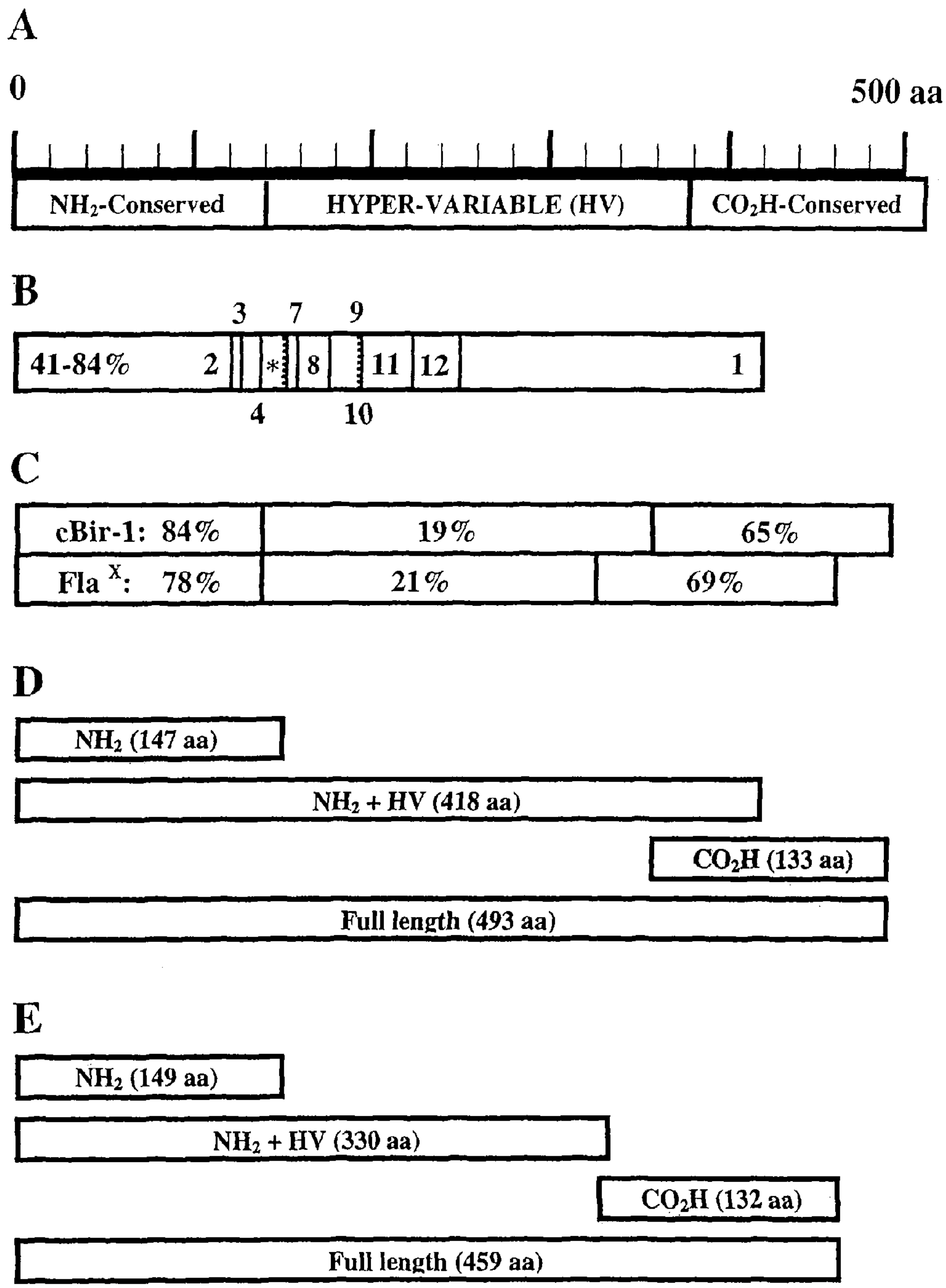
FIG. 1 shows a schematic of flagellin clones with percent similarity to related flagellin B from the rumen anaerobe, *Butyrivibrio fibrisolvens*.

In one aspect, the present invention provides polynucleotide compositions comprising a sequence selected from the group consisting of:

(a) sequences provided in SEQ ID NOs: 75, 83, 85, 1-37, 51-74, 76-78 and 87;

(b) complements of the sequences provided in SEQ ID NOs: 75, 83, 85, 1-37, 51-74, 76-78 and 87;

(c) sequences consisting of at least 20, 25, 30, 35, 40, 45, 50, 75 and 100 contiguous residues of a sequence provided in SEQ ID NOs: 75, 83, 85, 1-37, 51-74, 76-78 and 87;

(d) sequences that hybridize to a sequence provided in SEQ ID NOs: 75, 83, 85, 1-37, 51-74, and 76-78, under moderate or highly stringent conditions;

(e) sequences having at least 75%, 80%, 85%, 90%, 95%, 96%, 97%, 98% or 99% identity to a sequence of SEQ ID NOs: 75, 83, 85, 1-37, 51-74, 76-78 and 87;

(f) degenerate variants of a sequence provided in SEQ ID NOs: 75, 83, 85, 1-37, 51-74, 76-78 and 87.

The present invention, in another aspect, provides polypeptide compositions comprising an amino acid sequence that is encoded by a polynucleotide sequence described above.

The present invention further provides polypeptide compositions comprising an amino acid sequence selected from the group consisting of sequences recited in SEQ ID NOs: 79, 84, 86, 80-82, 38-50 and 88-89.

In certain preferred embodiments, the polypeptides and/or polynucleotides of the present invention are immunogenic, i.e., they are capable of eliciting an immune response, particularly a humoral and/or cellular immune response, as further described herein.

The present invention further provides fragments, variants and/or derivatives of the disclosed polypeptide and/or polynucleotide sequences, wherein the fragments, variants and/or derivatives preferably have a level of immunogenic activity of at least about 50%, preferably at least about 70% and more preferably at least about 90% of the level of immunogenic activity of a polypeptide sequence set forth in SEQ ID NOs: 79, 84, 86, 80-82, and 38-50 or a polypeptide sequence encoded by a polynucleotide sequence set forth in SEQ ID NOs: 75, 83, 85, 1-37, 51-74, 76-78 and 88-89.

The present invention further provides polynucleotides that encode a polypeptide described above, expression vectors comprising such polynucleotides and host cells transformed or transfected with such expression vectors.

Another aspect of the present invention provides for isolated antibodies, or antigen-binding fragment thereof, that specifically bind to the polypeptides of the present invention. In one embodiment of the invention, the antibody may be a monoclonal antibody. In a further embodiment the antibody is a human antibody or an antibody that has been humanized. In yet further embodiments, the antibodies of the present invention bind to flagellin proteins and in one embodiment the antibodies are neutralizing antibodies against flagellin proteins. In an additional embodiment, said antibodies block the interaction between a flagellin protein and a Toll-like receptor. In one particular embodiment, the Toll-like receptor is TLR5.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusions proteins may comprise multiple immunogenic polypeptides or portions/variants thereof, as described herein, and may further comprise one or more polypeptide segments for facilitating the expression, purification and/or immunogenicity of the polypeptide(s).

The present invention also provides, in other aspects, oligonucleotides that hybridize to the polynucloeotides of the present invention. In one embodiment, the oligonucleotides hybridize to the polynucleotides of the present invention under highly stringent conditions. In one embodiment, the oligonucleotides hybridize to polynucleotides that encode flagellin proteins.

The present invention further provides, in one aspect, methods of stimulating and/or expanding T cells specific for an enteric bacterial protein, comprising contacting T cells with at least one component including but not limited to, polypeptides or polynucleotides of the present invention, antigen-presenting cells that express a polynucleotide of the present invention under conditions and for a time sufficient to permit the stimulation and/or expansion of T cells. In one embodiment of the invention the T cells are CD4+ T cells. In a further embodiment, the CD4+ T cells mediate a decrease in inflammation in the colon. In another embodiment the T cells are specific for a flagellin polypeptide.

The present invention, in one aspect, also provides for populations of T cells produced according to the methods described herein. In one embodiment, said T cells produce cytokines that may include, but are not limited to, interleukin 10 (IL-10), interferon-β (IFN-β), interleukin 4 (IL-4), interleukin 12 (IL-12), transforming growth factor beta (TGFβ or interleukin 18 (IL-18). In preferred embodiments, the T cells produce IL-10 and/or TGFβ.

Within other aspects, the present invention provides pharmaceutical compositions comprising a polypeptide or polynucleotide as described above and a physiologically acceptable carrier.

Within a related aspect of the present invention, the pharmaceutical compositions, e.g., vaccine compositions, are provided for prophylactic or therapeutic applications. Such compositions generally comprise an immunogenic polypeptide or polynucleotide of the invention and an immunostimulant, such as an adjuvant.

The present invention further provides pharmaceutical compositions that comprise: (a) an antibody or antigen-binding fragment thereof that specifically binds to a polypeptide of the present invention, or a fragment thereof; and (b) a physiologically acceptable carrier.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusions proteins may comprise multiple immunogenic polypeptides or portions/variants thereof, as described herein, and may further comprise one or more polypeptide segments for facilitating the expression, purification and/or immunogenicity of the polypeptide(s).

Within further aspects, the present invention provides pharmaceutical compositions comprising: (a) T cells specific for a polypeptide as described above and (b) a pharmaceutically acceptable carrier or excipient. Illustrative T cells include T cells expressing a variety of cytokines including interleukin 10 (IL-10), interferon-β (IFN-β), interleukin 4 (IL-4), interleukin 12 (IL-12), transforming growth factor beta (TGFβ or interleukin 18 (IL-18). In preferred embodiments, the T cells produce IL-10 and/or TGFβ.

Within further aspects, the present invention provides pharmaceutical compositions comprising: (a) an antigen presenting cell that expresses a polypeptide as described above and (b) a pharmaceutically acceptable carrier or excipient. Illustrative antigen presenting cells include dendritic cells, macrophages, monocytes, fibroblasts and B cells.

Within related aspects, pharmaceutical compositions are provided that comprise: (a) T cells specific for a polypeptide as described above or an antigen presenting cell that expresses a polypeptide as described above and (b) an immunostimulant. Illustrative immunostimulants include adjuvants such as Freund's Incomplete Adjuvant; Freund's Complete Adjuvant; Merck Adjuvant 65; AS-1, AS-2; aluminum hydroxide gel; aluminum phosphate; a salt of calcium, iron or zinc; an insoluble suspension of acylated tyrosine acylated sugars; cationically or anionically derivatized polysaccharides; polyphosphazenes; biodegradable microspheres; monophosphoryl lipid A, QS21, aminoalkyl glucosaminide 4-phosphates, or quil A.

In a related aspect, the present invention provides a method of stimulating an immune response in a mammal, comprising administering to the mammal the compositions described above. In one embodiment, the immune response comprises T cells that produce a cytokine including, but not limited to, interleukin 10 (IL-10), interferon-β (IFN-β), interleukin 4 (IL-4), interleukin 12 (IL-12), transforming growth factor beta (TGFβ or interleukin 18 (IL-18). Particularly illustrative cytokines comprise IL-10 and/or TGFβ.

In a related aspect, the present invention provides a method of decreasing gastrointestinal inflammation associated with inflammatory bowel disease in a mammal, comprising administering to said mammal the compositions of the present invention.

Another aspect of the present invention provides for a method of detecting the presence of inflammatory bowel disease in a mammal comprising contacting a biological sample from the mammal, wherein said biological sample comprises antibodies, with the polypeptides described above, detecting in the sample an amount of antibody that binds to the polypeptide; and comparing the amount of bound antibody to a predetermined cut-off value and therefrom determining the presence of inflammatory bowel disease in the mammal. Illustrative biological samples include sera, stool, tissue or other material obtained by colonoscopy, ileoscopy, esophagogastroduodenoscopy (EGP), or surgery. In one particular embodiment the polypeptide comprises a flagellin polypeptide.

Another aspect of the present invention provides for a method of detecting the presence of inflammatory bowel disease in a mammal comprising contacting a biological sample from the mammal, wherein said biological sample comprises polynucleotides, with at least one oligonucleotide that is at least in part complementary to a polynucleotide described above, detecting in the sample an amount of a polynucleotide that hybridizes to said oligonucleotide; and comparing the amount of said polynucleotide that hybridizes to said oligonucleotide to a predetermined cut-off value, and therefrom determining the presence of inflammatory bowel disease in a mammal. In one embodiment, the oligonucleotide hybridizes under moderately stringent conditions. In a particular embodiment, the polymerase chain reaction is used to determine the amount of polynucleotide that hybridizes to said oligonucleotide. In another embodiment, a hybridization assay is used to determine the amount of polynucleotide that hybridizes to said oligonucleotide. Illustrative biological samples comprising polynucleotides include sera, stool, tissue or other material obtained by colonoscopy or colonic biopsy, ileoscopy, esophagogastroduodenoscopy (EGP), or surgery. In one particular embodiment, the polynucleotide encodes a flagellin protein.

Another aspect of the present invention provides for a method of stimulating and/or expanding B cells that produce antibodies specific for an enteric bacterial protein, comprising contacting B cells with the polypeptides or polynucleotides mentioned above under conditions and for a time sufficient to permit the stimulation and/or expansion of B cells. In one embodiment the B cells produce antibodies that bind to a flagellin protein. In another embodiment said antibodies are neutralizing antibodies against a flagellin protein. In another embodiment, the antibodies block the interaction between a flagellin protein and a Toll-like receptor. In one particular embodiment, the Toll-like receptor is TLR5.

Within related aspects, the present invention provides for populations of B cells generated as described above.

Within further aspects, the present invention provides a method of identifying bacterial antigens associated with inflammatory bowel disease in a mammal, comprising contacting a biological sample that comprises T cells with the polynucleotides, or polypeptides described above, or antigen-presenting cells that express a polynucleotide described herein, under conditions and for a time sufficient to permit the stimulation and/or expansion of T cells, and further, detecting in the sample the magnitude of said stimulation and/or expansion of T cells; and, comparing the magnitude of said stimulation and/or expansion to a predetermined cut-off value, and therefrom identifying bacterial antigens associated with inflammatory bowel disease in the mammal. In one embodiment, the mammal is a human. In a further embodiment the mammal is a mouse. Illustrative mouse strains are C3H/HeJ Bir, BALB/c IL-10−/−, B6 IL-10−/−, B10 IL-10−/−, MDR1a−/−, TCRα−/−, IL-2−/−, IL-2R−/−, mice with DSS (Dextransodiumsulfate) induced colitis, $G\alpha_{ai}$−/−, and CD45 RB transgenic mice. In one particular embodiment, the strain of mouse is C3H/HeJ Bir. In another embodiment, the mammal is a rat. In one particular embodiment, the rat is an HLA-B27-transgenic rat.

In certain other aspects, the present invention provides methods of monitoring the progression of inflammatory bowel disease in a mammal, comprising the steps of: (a) obtaining a biological sample from the mammal, wherein said biological sample comprises antibodies; (b) contacting the biological sample with a polypeptide described herein; (c) detecting in the sample an amount of antibody that binds to the polypeptide; and (d) repeating steps (a), (b), and (c) using a biological sample obtained from the mammal at a subsequent point in time; and (e) comparing the amount of bound antibody in step (c) to the amount of bound antibody in step (d) and therefrom monitoring the progression of inflammatory bowel disease in the mammal.

Another aspect of the present invention provides methods of identifying bacterial antigens associated with inflammatory bowel disease in a first mammal, comprising the steps of: (a) obtaining a biological sample from said first mammal wherein said biological sample comprises DNA from cecal bacteria; (b) constructing an expression library with said DNA; (c) screening said expression library with sera from either said first mammal or a second mammal with inflammatory bowel disease; thereby identifying bacterial antigens associated with inflammatory bowel disease. In one embodiment, both the first and second mammals are mice. In a related embodiment, said first mammal is a C3H/HeJ Bir mouse and said second mammal is a different strain of mouse including BALB/c IL-10−/−, B6 IL-10−/−, MDR1a−/−, or CD45 RB transgenic mice. In another related embodiment, said first mammal is a mouse and said second mammal is a human.

In certain other aspects, the present invention provides methods of monitoring the progression of inflammatory bowel disease in a mammal, comprising the steps of (a) obtaining a biological sample from said mammal, wherein said biological sample comprises polynucleotides; (b) contacting said sample with at least one oligonucleotide that is at least in part complementary to a polynucleotide described herein; (c) detecting in the sample an amount of a polynucleotide that hybridizes to said oligonucleotide; (d) repeating steps (a), (b), and (c) using a biological sample obtained from said mammal at a subsequent point in time; and (e) comparing the amount of said polynucleotide that hybridizes to said oligonucleotide in step (c) to the amount of said polynucleotide that hybridizes to said oligonucleotide in step (d); and therefrom monitoring the progression of inflammatory bowel disease in a mammal. In one embodiment, the oligonucleotide hybridizes under moderately stringent conditions. In one particular embodiment, the polymerase chain reaction is used to determine the amount of polynucleotide that hybridizes to said oligonucleotide. In another embodiment, the amount of polynucleotide that hybridizes to said oligonucleotide is determined using a hybridization assay. Illustrative biological samples are sera, stool, tissue or other material obtained by colonoscopy or colonic biopsy, ileoscopy, esophagogastroduodenoscopy (EGP), or surgery. In a related embodiment, the polynucleotide comprises a polynucleotide that encodes a flagellin protein.

Other aspects of the present invention provides diagnostic kits comprising at least one oligonucleotide as described herein. In related aspects, a diagnostic kit may comprise at least one antibody as described herein, and a detection reagent, wherein the detection reagent comprises a reporter group.

In certain aspects, the present invention provides a diagnostic kit comprising a portion of at least one or more polypeptides described herein, wherein said portion can be bound by an antibody; and a detection reagent comprising a reporter group. In a related embodiment, said portion of at least one or more polypeptides is immobilized on a solid support. Illustrative detection reagents comprise an anti-immunoglobulin, protein G, protein A, or a lectin. Illustrative reporter groups comprise radioactive groups, fluorescent groups, luminescent groups, enzymes, biotin, or dyes.

Within yet another aspect, the present invention provides a method for identifying an inflammatory bowel disease type in a patient, comprising: (a) obtaining an antibody comprising biological sample from a patient; (b) contacting the biological sample with a polypeptide of claim 2; (c) detecting in the sample an amount of antibody that binds to the polypeptide; and (d) comparing the amount of bound antibody to a predetermined value associated with and therefrom subdividing the inflammatory bowel disease type. Within one embodiment the disease type is selected from ulcerative colitis and Crohn's Disease. Within another embodiment the polypeptide comprises a flagellin polypeptide.

BRIEF DESCRIPTION OF THE SEQUENCE IDENTIFIERS

SEQ ID NO:1 is the determined cDNA sequence for 76779.

SEQ ID NO:2 is the determined cDNA sequence for 76780.

SEQ ID NO:3 is the determined cDNA sequence for 76959.

SEQ ID NO:4 is the determined cDNA sequence for 76960.

SEQ ID NO:5 is the determined cDNA sequence for 76961.

SEQ ID NO:6 is the determined cDNA sequence for 76781.

SEQ ID NO:7 is the determined cDNA sequence for 76962.

SEQ ID NO:8 is the determined cDNA sequence for 76782.

SEQ ID NO:9 is the determined cDNA sequence for 76963.

SEQ ID NO:10 is the determined cDNA sequence for 76964.

SEQ ID NO:11 is the determined cDNA sequence for 77529.

SEQ ID NO:12 is the determined cDNA sequence for 76965.

SEQ ID NO:13 is the determined cDNA sequence for 76966.

SEQ ID NO:14 is the determined cDNA sequence for 76967.

SEQ ID NO:15 is the determined cDNA sequence for 76968.

SEQ ID NO:16 is the determined cDNA sequence for 77530.

SEQ ID NO:17 is the determined cDNA sequence for 76969.

SEQ ID NO:18 is the determined cDNA sequence for 76970.

SEQ ID NO:19 is the determined cDNA sequence for 76971.

SEQ ID NO:20 is the determined cDNA sequence for 77073.

SEQ ID NO:21 is the determined cDNA sequence for 76972.

SEQ ID NO:22 is the determined cDNA sequence for 76973.

SEQ ID NO:23 is the determined cDNA sequence for 76974.

SEQ ID NO:24 is the determined cDNA sequence for 77074.

SEQ ID NO:25 is the determined cDNA sequence for 77531.

SEQ ID NO:26 is the determined cDNA sequence for 76975.

SEQ ID NO:27 is the determined cDNA sequence for 77075.

SEQ ID NO:28 is the determined cDNA sequence for 76976.

SEQ ID NO:29 is the determined cDNA sequence for 76977.

SEQ ID NO:30 is the determined cDNA sequence for 77532.

SEQ ID NO:31 is the determined cDNA sequence for 77533.

SEQ ID NO:32 is the determined cDNA sequence for 77534.

SEQ ID NO:33 is the determined cDNA sequence for 77535.

SEQ ID NO:34 is the determined cDNA sequence for 77076.

SEQ ID NO:35 is the determined cDNA sequence for 77536.

SEQ ID NO:36 is the determined cDNA sequence for 77538.

SEQ ID NO:37 is the determined cDNA sequence for 77539.

SEQ ID NO:38 is the amino acid sequence encoded by 76779.

SEQ ID NO:39 is the amino acid sequence encoded by 76780.

SEQ ID NO:40 is the amino acid sequence encoded by 76959.

SEQ ID NO:41 is the amino acid sequence encoded by 76959.

SEQ ID NO:42 is the amino acid sequence encoded by 76781.

SEQ ID NO:43 is the amino acid sequence encoded by 76782.

SEQ ID NO:44 is the amino acid sequence encoded by 76967.

SEQ ID NO:45 is the amino acid sequence encoded by 76969.

SEQ ID NO:46 is the amino acid sequence encoded by 76972.

SEQ ID NO:47 is the amino acid sequence encoded by 76974.

SEQ ID NO:48 is the amino acid sequence encoded by 76975.

SEQ ID NO:49 is the amino acid sequence encoded by 76977.

SEQ ID NO:50 is the amino acid sequence encoded by 77076.

SEQ ID NO:51 is the determined cDNA sequence for 73261.

SEQ ID NO:52 is the determined cDNA sequence for 73262.

SEQ ID NO:53 is the determined cDNA sequence for 73263.

SEQ ID NO:54 is the determined cDNA sequence for 73264.

SEQ ID NO:55 is the determined cDNA sequence for 73266.

SEQ ID NO:56 is the determined cDNA sequence for 73267.

SEQ ID NO:57 is the determined cDNA sequence for 73268.

SEQ ID NO:58 is the determined cDNA sequence for 73269.

SEQ ID NO:59 is the determined cDNA sequence for 73270.

SEQ ID NO:60 is the determined cDNA sequence for 73272.

SEQ ID NO:61 is the determined cDNA sequence for 73273.

SEQ ID NO:62 is the determined cDNA sequence for 73274.

SEQ ID NO:63 is the determined cDNA sequence for 73275.

SEQ ID NO:64 is the determined cDNA sequence for 73037.

SEQ ID NO:65 is the determined cDNA sequence for 75038.

SEQ ID NO:66 is the determined cDNA sequence for 75039.

SEQ ID NO:67 is the determined cDNA sequence for 75040.

SEQ ID NO:68 is the determined cDNA sequence for 75041.

SEQ ID NO:69 is the determined cDNA sequence for 75042.

SEQ ID NO:70 is the determined cDNA sequence for 75044.

SEQ ID NO:71 is the determined cDNA sequence for 75045.

SEQ ID NO:72 is the determined cDNA sequence for 75046.

SEQ ID NO:73 is the determined cDNA sequence for 75047.

SEQ ID NO:74 is the determined cDNA sequence for 75048.

SEQ ID NO:75 is the full-length determined cDNA sequence for 83537, also referred to as Flagellin X.

SEQ ID NO:76 is the determined cDNA sequence for the amino terminal conserved end of Flagellin X.

SEQ ID NO:77 is the determined cDNA sequence for the amino terminal conserved end plus the variable region of Flagellin X.

SEQ ID NO:78 is the determined cDNA sequence for the carboxy-terminal conserved end of Flagellin X.

SEQ ID NO:79 is the full-length amino acid sequence of Flagellin X.

SEQ ID NO:80 is the amino acid sequence of the amino terminal conserved end of Flagellin X.

SEQ ID NO:81 is the amino acid sequence of the amino terminal conserved end plus the variable region of Flagellin X.

SEQ ID NO:82 is the amino acid sequence of the carboxy-terminal conserved end of Flagellin X.

SEQ ID NO:83 is the full-length coding sequence of *Helicobacter bilis* flagellin B.

SEQ ID NO:84 is the full-length protein sequence of *Heticobacter bilis* flagellin B, encoded by the nucleotide sequence set forth in SEQ ID NO:83.

SEQ ID NO:85 is the full-length coding sequence of Cbir-1 flagellin (partial sequence set forth in SEQ ID NO:1).

SEQ ID NO:86 is the full-length protein sequence of Cbir-1 flagellin, encoded by the nucleotide sequence set forth in SEQ ID NO:85.

SEQ ID NO:87 is the determined full length cDNA sequence for clone 76963 (SEQ ID NO:9), CBir-11.

SEQ ID NO:88 is a predicted-translated protein sequence encoded by SEQ ID NO:86, a flagellin-like sequence.

SEQ ID NO:89 is a predicted translated protein sequence encoded by SEQ ID NO:86, a phosphoesterase-like sequence.

DETAILED DESCRIPTION OF THE INVENTION

The present invention is directed generally to compositions and their use in the therapy and diagnosis of IBD. As described further below, illustrative compositions of the present invention include, but are not restricted to, polypeptides, particularly immunogenic polypeptides, polynucleotides encoding such polypeptides, antibodies and other binding agents, antigen presenting cells (APCs) and immune system cells (e.g., T and B cells).

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

As used in this specification and the appended claims, the singular forms "a," "an" and "the" include plural references unless the content clearly dictates otherwise. All references cited herein are each incorporated by reference in their entirety.

Polypeptide Compositions

As used herein, the term "polypeptide" " is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Particularly illustrative polypeptides of the present invention comprise those encoded by a polynucleotide sequence set forth in any one of SEQ ID NOs:1-37, 51-78, 83, 85 and 87, or a sequence that hybridizes under moderately stringent conditions, or, alternatively, under highly stringent conditions, to a polynucleotide sequence set forth in any one of SEQ ID NOs:1-37, 51-78, 83, 85 and 87. Certain other illustrative polypeptides of the invention comprise amino acid sequences as set forth in any one of SEQ ID NOs:38-50, 79-82, 84, and 86.

The polypeptides of the present invention are sometimes herein referred to as bacterial proteins or bacterial polypeptides, as an indication that their identification has been based at least in part upon their expression in enteric bacterial samples isolated from the colon of individuals with IBD. The peptides described herein may be identified from a lesion in the colon from a patient with IBD. Accordingly, such a peptide may not be present in adjacent normal tissue. Alternatively, a peptide of the present invention may be identified from an enteric bacterial sample isolated from the colon of an individual with IBD said enteric bacteria being absent from individuals not affected with IBD. In a further embodiment, the polypeptides of the present invention may be identified by their ability to activate T cells from individuals affected with IBD. Additionally, polypeptides described herein may be identified by their reactivity with sera from IBD patients as compared to their lack of reactivity to sera from unaffected individuals.

Thus, a "bacterial polypeptide" or "bacterial protein," refers generally to a polypeptide sequence of the present invention, or a polynucleotide sequence encoding such a polypeptide, that is present in samples isolated from a substantial proportion of IBD patients, for example preferably greater than about 20%, more preferably greater than about 30%, and most preferably greater than about 50% or more of patients tested as determined using a representative assay provided herein. A bacterial polypeptide sequence of the invention, based upon its expression in enteric bacterial samples isolated from the colon of individuals with IBD, has particular utility both as a diagnostic marker as well as a therapeutic target, as further described below. In one particular embodiment of the present invention, a bacterial polypeptide or bacterial protein comprises a flagellin protein.

In certain preferred embodiments, the polypeptides of the invention are immunogenic, i.e., they react detectably within an immunoassay (such as an ELISA or T-cell stimulation assay) with antisera and/or T-cells from a patient with IBD. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology,* 3rd ed., 243-247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1-30 amino acids, preferably 5-15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotide sequences disclosed herein, or immunogenic fragments or variants thereof, or to one or more nucleic acid sequences which hybridize to one or more of these sequences under conditions of moderate to high stringency.

The present invention, in another aspect, provides polypeptide fragments comprising at least about 5, 10, 15, 20, 25, 50, or 100 contiguous amino acids, or more, including all intermediate lengths, of a polypeptide compositions set forth herein, such as those set forth in SEQ ID NOs:38-50, 79-82, 84, 86 and 88-89, or those encoded by a polynucleotide sequence set forth in a sequence of SEQ ID NOs:1-37, 51-78, 83, 85 and 87.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one preferred embodiment, the polypeptide fragments and variants provided by the present invention are immunologically reactive with an antibody and/or T-cell that reacts with a full-length polypeptide specifically set forth herein.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., 1-30 amino acids, preferably 5-15 amino acids) has been removed from the N- and/or C-terminal of the mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |

TABLE 1-continued

| Amino Acids | | | Codons | | | | | |
|---|---|---|---|---|---|---|---|---|
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUG | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr, (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Saitou, N. Nei, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a fusion polypeptide that comprises multiple polypeptides as described herein, or that comprises at least one polypeptide as described herein and an unrelated sequence, such as a known bacterial protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.*, 336:86-91, 1997).

In one preferred embodiment, the immunological fusion partner is derived from a *Mycobacterium* sp., such as a *Mycobacterium tuberculosis*-derived Ra12 fragment. Ra12 compositions and methods for their use in enhancing the expression and/or immunogenicity of heterologous polynucleotide/polypeptide sequences is described in U.S. Patent Application 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application 60/158,585; see also, Skeiky et al., *Infection and Immun.* (1999) 67:3998-4007, incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium *Haemophilus* influenza B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from *influenzae* virus, NSI (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798, 1992). Within a preferred embodiment, a repeat portion of LYTA may be incorporated into a fusion polypeptide. A repeat portion is found in the C-terminal region starting at residue 178. A particularly preferred repeat portion incorporates residues 188-305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of $CD4^+$ T-cells specific for the polypeptide.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

Polynucleotide Compositions

The present invention, in other aspects, provides polynucleotide compositions. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence.

Therefore, according to another aspect of the present invention, polynucleotide compositions are provided that comprise some or all of a polynucleotide sequence set forth in any one of SEQ ID NOs:1-37, 51-78, 83, 85 and 87, complements of a polynucleotide sequence set forth in any one of SEQ ID NOs:1-37, 51-78, 83, 85 and 87, and degenerate variants of a polynucleotide sequence set forth in any one of SEQ ID NOs:1-37, 51-78, 83, 85 and 87. In certain preferred embodiments, the polynucleotide sequences set forth herein encode immunogenic polypeptides, as described above. In other certain preferred embodiments, the polynucloetide sequences set forth herein encode IBD-associated bacterial proteins isolated as described herein from individuals affected with IBD. In other certain preferred embodiments, the polynucloetide sequences set forth herein encode flagellin proteins.

In other related embodiments, the present invention provides polynucleotide variants having substantial identity to the sequences disclosed herein in SEQ ID NOs:1-37, 51-78, 83, 85, and 87, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising or consisting of various lengths of contiguous stretches of sequence identical to or complementary to one or more of the sequences disclosed herein. For example, polynucleotides are provided by this invention that comprise or consist of at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of the disclosed sequence or at both ends of the disclosed sequence.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In certain preferred embodiments, the polynucleotides described above, e.g., polynucleotide variants, fragments and hybridizing sequences, encode polypeptides that are immunologically cross-reactive with a polypeptide sequence specifically set forth herein. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M.O. (1978) A model of evolutionary change in proteins—Matrices for detecting distant relationships. In Dayhoff, M.O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad, Sci. USA* 80:726-730.

Alternatively, optimal alignment of sequences for comparison may be conducted by the local identity algorithm of Smith and Waterman (1981) *Add APL. Math* 2:482, by the identity alignment algorithm of Needleman and Wunsch (1970) *J. Mol. Biol.* 48:443, by the search for similarity methods of Pearson and Lipman (1988) *Proc. Natl. Acad Sci. USA* 85: 2444, by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification, and/or database sequence comparison).

Therefore, in another embodiment of the invention, a mutagenesis approach, such as site-specific mutagenesis, is employed for the preparation of immunogenic variants and/or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced immunogenic activity.

In other embodiments of the present invention, the polynucleotide sequences provided herein can be advantageously used as probes or primers for nucleic acid hybridization. As such, it is contemplated that nucleic acid segments that comprise or consist of a sequence region of at least about a 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch (es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of to 25 contiguous nucleotides, or even longer where desired.

Hybridization probes may be selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202, by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

According to another embodiment of the present invention, polynucleotide compositions comprising antisense oligonucleotides are provided. Antisense oligonucleotides have been demonstrated to be effective and targeted inhibitors of protein synthesis, and, consequently, provide a therapeutic approach by which a disease can be treated by inhibiting the synthesis of proteins that contribute to the disease. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829). Further, examples of antisense inhibition have been demonstrated with the nuclear protein cyclin, the multiple drug resistance gene (MDGI1), ICAM-1, E-selectin, STK-1, striatal $GABA_A$ receptor and human EGF (Jaskulski et al., Science. 1988 Jun. 10; 240(4858):1544-6; Vasanthakumar and Ahmed, Cancer Commun. 1989; 1(4):225-32; Peris et al., Brain Res Mol Brain Res. 1998 Jun. 15; 57(2):310-20; U.S. Pat. No. 5,801,154; U.S. Pat. No. 5,789,573; U.S. Pat. No. 5,718,709 and U.S. Pat. No. 5,610,288). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683).

Therefore, in certain embodiments, the present invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein. Selection of antisense compositions specific for a given gene sequence is based upon analysis of the chosen target sequence and determination of secondary structure, $T_m$, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA, are those which are at or near the AUG translation initiation codon, and those sequences which are substantially complementary to 5' regions of the mRNA. These secondary structure analyses and target site selection considerations can be performed, for example, using v. 4 of the OLIGO primer analysis software and/or the BLASTN 2.0.5 algorithm software (Altschul et al., Nucleic Acids Res. 1997, 25(17):3389-402).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., Nucleic Acids Res. 1997 Jul. 15; 25(14):2730-6). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane.

According to another embodiment of the invention, the polynucleotide compositions described herein are used in the design and preparation of ribozyme molecules for inhibiting expression of the bacterial polypeptides and proteins of the present invention in bacterial cells. Ribozymes are RNA-protein complexes that cleave nucleic acids in a site-specific fashion. Ribozymes have specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). For example, a large number of ribozymes accelerate phosphoester transfer reactions with a high degree of specificity, often cleaving only one of several phosphoesters in an oligonucleotide substrate (Cech et al., Cell. 1981 December; 27(3 Pt 2):487-96; Michel and Westhof, J Mol Biol. 1990 Dec. 5; 216(3):585-610; Reinhold-Hurek and Shub, Nature. 1992 May 14; 357(6374):173-6). This specificity has been attributed to the requirement that the substrate bind via specific base-pairing interactions to the internal guide sequence ("IGS") of the ribozyme prior to chemical reaction.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., Proc Natl Acad Sci USA. 1992 Aug. 15; 89(16):7305-9). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. Nucleic Acids Res. 1992 Sep. 11; 20(17):4559-65. Examples of hairpin motifs are described by Hampel et al. (Eur. Pat. Appl. Publ. No. EP 0360257), Hampel and Tritz, Biochemistry 1989 Jun. 13; 28(12):4929-33; Hampel et al., Nucleic Acids Res. 1990 Jan. 25; 18(2):299-304 and U.S. Pat. No. 5,631,359. An example of the hepatitis δ virus motif is described by Perrotta and Been, Biochemistry. 1992 Dec. 1; 31(47):11843-52; an example of the RNaseP motif is described by Guerrier-Takada et al., Cell. 1983 December; 35(3 Pt 2):849-57; Neurospora VS RNA ribozyme motif is described by Collins (Saville and Collins, Cell. 1990 May 18; 61(4):685-96; Saville and Collins, Proc Natl Acad Sci USA. 1991 Oct. 1; 88(19):8826-30; Collins and Olive, Biochemistry. 1993 Mar. 23; 32(11):2795-9); and an example of the Group I intron is described in (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

Ribozymes may be designed as described in Int. Pat. Appl. Publ. No. WO 93/23569 and Int. Pat. Appl. Publ. No. WO 94/02595) and synthesized to be tested in vitro and in vivo, as described. Such ribozymes can also be optimized for delivery. While specific examples are provided, those in the art will recognize that equivalent RNA targets in other species can be utilized when necessary.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells Ribozymes expressed from such promoters have been shown to function in mammalian cells. Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In another embodiment of the invention, peptide nucleic acids (PNAs) compositions are provided. PNA is a DNA mimic in which the nucleobases are attached to a pseudopeptide backbone (Good and Nielsen, Antisense Nucleic Acid Drug Dev. 1997 7(4) 431-37). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (*Trends Biotechnol* 1997 June; 15(6):224-9). As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., *Science* 1991 Dec. 6; 254(5037):1497-500; Hanvey et al., Science. 1992 Nov. 27; 258(5087):1481-5; Hyrup and Nielsen, Bioorg Med Chem. 1996 January; 4(1):5-23). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., Bioorg Med Chem. 1995 April; 3(4):437-45). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., Bioorg Med Chem. 1995 April; 3(4):437-45; Petersen et al., J Pept Sci. 1995 May-June; 1(3):175-83; Orum et al., Biotechniques. 1995 September; 19(3):472-80; Footer et al., Biochemistry. 1996 Aug. 20; 35(33):10673-9; Griffith et al., Nucleic Acids Res. 1995 Aug. 11; 23(15):3003-8; Pardridge et al., Proc Natl Acad Sci USA. 1995 Jun. 6; 92(12):5592-6; Boffa et al., Proc Natl Acad Sci USA. 1995 Mar. 14; 92(6):1901-5; Gambacorti-Passerini et al., Blood. 1996 Aug. 15; 88(4):1411-7; Armitage et al., Proc Natl Acad Sci USA. 1997 Nov. 11; 94(23):12320-5; Seeger et al., Biotechniques. 1997 September; 23(3):512-7). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (Anal Chem. 1993 Dec. 15; 65(24):3545-9) and Jensen et al. (Biochemistry. 1997 Apr. 22; 36(16):5072-7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Polynucleotide Identification, Characterization and Expression

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references). For example, a polynucleotide may be identified, as described in more detail below, by screening a microarray of cDNAs for bacterial cDNAs present in tissue samples isolated from individuals affected with IBD as compared to samples isolated from unaffected individuals. Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 93:10614-10619, 1996 and Heller et al., *Proc. Natl. Acad Sci. USA* 94:2150-2155, 1997). Alternatively, polynucleotide compositions of the present invention may be identified by screening mouse or human cecal bacteria genomic random shear expression libraries, as described in Example 1.

Alternatively, polynucleotides may be amplified from cDNA prepared from cells expressing the bacterial proteins described herein. Many template dependent processes are available to amplify a target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

An amplified portion of a polynucleotide of the present invention may be used to isolate a full length gene from a suitable library (e.g., a bacterial cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybiidizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111-19, 1991) and walking PCR (Parker et al., *Nucl. Acids. Res.* 19:3055-60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells.

Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215-223, Horn, T. et al. (1980) *Nucl. Acids Res. Symp. Ser.* 225-232). Alternatively, the protein itself may be produced rising chemical methods to synthesize the amino acid sequence of a polypeptide, or a portion thereof. For example, peptide synthesis can be performed using various solid-phase techniques (Roberge, J. Y. et al. (1995) *Science* 269:202-204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUESCRIPT phagemid (Stratagene, La Jolla, Calif.) or pSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as pBLUESCRIFPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503-5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516-544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307-311. Alternatively, plant promoters such as the small subunit of RUBISCO or heat shock promoters may be used (Coruzzi, G. et al. (1984) *EMBO J.* 3:1671-1680; Broglie, R. et al. (1984) *Science* 224:838-843; and Winter, J. et al. (1991) *Results Probl. Cell Differ.* 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed (Engelhard, E. K. et al. (1994) *Proc. Natl. Acad Sci.* 91:3224-3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223-32) and adenine phosphoribosyltransferase (Lowy, I. et al. (1990) *Cell* 22:817-23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) *Proc. Natl. Acad Sci.* 77:3567-70); npt, which confers resistance to the aminoglycosides, neomycin and G-418 (Colbere-Garapin, F. et al (1981) *J. Mol. Biol.* 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad Sci.* 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263-281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441-453).

In addition to recombinant production methods, polypeptides of the invention, and fragments thereof, may be produced by direct peptide synthesis using solid-phase techniques (Merrifield J. (1963) *J. Am. Chem. Soc.* 85:2149-2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Antibody Compositions, Fragments Thereof and Other Binding Agents

According to another aspect, the present invention further provides binding agents, such as antibodies and antigen-binding fragments thereof, that exhibit immunological binding to a bacterial polypeptide disclosed herein, or to a portion, variant or derivative thereof. In one particular embodiment, the antibodies of the present invention bind to a Toll-like receptor. Illustrative Toll-like receptors (TLR) include, but are not limited to, TLR5. In a related embodiment, the antibodies of the present invention may bind to a flagellin protein. In another embodiment, the antibodies of the present invention are neutralizing antibodies that block the interaction between TLR5 and a flagellin protein.

An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439-473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Binding agents may be further capable of differentiating between patients with and without IBD, using the representative assays provided herein. For example, antibodies or other binding agents that bind to a bacterial protein will preferably generate a signal indicating the presence of IBD in at least about 20% of patients with the disease, more preferably at least about 30% of patients. Alternatively, or in addition, the antibody will generate a negative signal indicating the absence of the disease in at least about 90% of individuals without IBD. To determine whether a binding agent satisfies this requirement, biological samples (e.g., blood, sera, sputum, urine, feces, and/or biopsies) from patients with and without IBD (as determined using standard clinical tests) may be assayed as described herein for the presence of polypeptides that bind to the binding agent. Preferably, a statistically significant number of samples with and without the disease will be assayed. Each binding agent should satisfy the above criteria; however, those of ordinary skill in the art will recognize that binding agents may be used in combination to improve sensitivity.

Binding agents may be further capable of identifying patients at risk for developing IBD, using the representative assays provided herein. For example, antibodies or other binding agents that bind to a bacterial protein will preferably generate a signal indicating a risk for the development of IBD in at least about 20% of patients with positive family history of the disease, or patients with a defined genetic risk for developing the disease (for example, individuals positive for the NOD2 mutation), more preferably at least about 30% of said individuals. Alternatively, or in addition, the antibody will generate a negative signal indicating the absence of risk for developing disease in at least about 90% of individuals with no family history or with no defined genetic risk of developing IBD. To determine whether a binding agent satisfies this requirement, biological samples (e.g., blood, sera, sputum, urine, feces, and/or biopsies) from patients with and without risk factors for the development of IBD (as determined using standard clinical tests) may be assayed as described herein for the presence of polypeptides that bind to the binding agent. Preferably, a statistically significant number of samples from individuals with and without risk of developing the disease will be assayed. Each binding agent should satisfy the above criteria; however, those of ordinary skill in the art will recognize that binding agents may be used in combination to improve sensitivity.

Binding agents of the present invention may be further used, either alone or in combination with other diagnostic modalities, to subdivide IBD patients into categories of disease that would be susceptible or resistant to new or existing treatments. In particular, serum reactivity against the binding agents to subdivide IBD patients would be useful as a stand alone diagnostic or in combination with other known diagnostic markers and assays, such as pANCA. Such binding agents could also be used to distinquish clinical subgroups of patients with Crohn's Disease, which would be of relevance to predict the clinical course of an individual patient or predict responsivensess to particular medication. Diagnostic use may be as a stand-alone test or used in combination with other serological testing methods or in combination with standard laboratory, clinical or pathological testing or with DNA-based testing such as for NOD2 mutations.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "$F(ab')_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091-4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349:293-299; Lobuglio et al. (1989) Proc. Nat. Acad. Sci. USA 86:4220-4224; Shaw et al. (1987) J Immunol. 138:4534-4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-1536; and Jones et al. (1986) Nature 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439-473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

T Cell Compositions

The present invention, in another aspect, provides T cells specific for a bacterial polypeptide disclosed herein, or for a variant or derivative thereof. Such cells may generally be prepared in vitro or ex vivo, using standard procedures. For example, T cells may be isolated from biopsies, bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). In one particular embodiment of the present invention, T cells may be isolated from intraepithelial lymphocytes (IEL) or lamina propria lymphocyte (LPL) samples originating from colon biopsies. Individuals with skill in the art will readily recognize that there numerous methodologies for isolating IEL and LPL (for example, methods described in Christ, A. D., S. P. Colgan, S. P. Balk, R. S. Blumberg. 1997. Immunol. Lett. 58:159; Boll G, Reimann J. Scand J Immunol 1995 August; 42(2):191-201). In certain aspects, T cells may be derived from related or unrelated humans, non-human mammals, cell lines or cultures.

T cells may be stimulated with a polypeptide, polynucleotide encoding a polypeptide and/or an antigen presenting cell (APC) that expresses such a polypeptide. Such stimulation is performed under conditions and for a time sufficient to permit the generation of T cells that are specific for the polypeptide of interest. Preferably, a bacterial polypeptide or polynucleotide of the invention is present within a delivery vehicle, such as a microsphere, to facilitate the generation of specific T cells.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065-1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a bacterial polypeptide (100 ng/ml-100 μg/ml, preferably 200 ng/ml-25 μg/ml) for 3-7 days will typically result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a bacterial polypeptide, polynucleotide or polypeptide-expressing APC may be $CD4^+$ and/or $CD8^+$. Bacterial polypeptide-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a bacterial polypeptide, polynucleotide or APC can be expanded in number either in vitro or in vivo. Proliferation of such T cells in vitro may be accomplished in a variety of ways. For example, the T cells can be re-exposed to a bacterial polypeptide, or a short peptide corresponding to an immunogenic portion of such a polypeptide, with or without the addition of T cell growth factors, such as interleukin-2, and/or stimulator cells that synthesize a bacterial polypeptide. Alternatively, one or more T cells that proliferate in the presence of the bacterial polypeptide can be expanded in number by cloning. Methods for cloning cells are well known in the art, and include limiting dilution.

In certain embodiments, T cells that produce anti-inflammatory cytokines may be desirable. Such cytokines may include, but are not limited to, 10 (IL-10), interferon-γ (IFN-γ), interleukin 4 (IL-4), interleukin 12 (IL-12), transforming growth factor beta (TGFβ and interleukin 18 (IL-18). In certain embodiments, an anti-inflammatory response is mediated by CD4+ T helper cells.

T Cell Receptor Compositions

The T cell receptor (TCR) consists of 2 different, highly variable polypeptide chains, termed the T-cell receptor α and β chains, that are linked by a disulfide bond (Janeway, Travers, Walport. *Immunobiology. Fourth Ed.,* 148-159. Elsevier Science Ltd/Garland Publishing. 1999). The α/β heterodimer complexes with the invariant CD3 chains at the cell membrane. This complex recognizes specific antigenic peptides bound to MHC molecules. The enormous diversity of TCR specificities is generated much like immunoglobulin diversity, through somatic gene rearrangement. The β chain genes contain over 50 variable (V), 2 diversity (D), over 10 joining (J) segments, and 2 constant region segments (C). The α chain genes contain over 70 V segments, and over 60 J segments but no D segments, as well as one C segment. During T cell development in the thymus, the D to J gene rearrangement of the β chain occurs, followed by the V gene segment rearrangement to the DJ. This functional $VDJ_\beta$ exon is transcribed and spliced to join to a $C_\beta$. For the α chain, a $V_\alpha$ gene segment rearranges to a $J_\alpha$ gene segment to create the functional exon that is then transcribed and spliced to the $C_\alpha$. Diversity is further increased during the recombination process by the random addition of P and N-nucleotides between the V, D, and J segments of the β chain and between the V and J segments in the α chain (Janeway, Travers, Walport. *Immunobiology*. Fourth Ed., 98 and 150. Elsevier Science Ltd/Garland Publishing. 1999).

The present invention, in another aspect, provides TCRs specific for a polypeptide disclosed herein, or for a variant or derivative thereof. In accordance with the present invention, polynucleotide and amino acid sequences are provided for the V-J or V-D-J junctional regions or parts thereof for the alpha and beta chains of the T-cell receptor which recognize bacterial polypeptides described herein. In general, this aspect of the invention relates to T-cell receptors which recognize or bind bacterial polypeptides presented in the context of MHC. In a preferred embodiment the bacterial antigens recognized by the T-cell receptors comprise a polypeptide of the present invention. For example, cDNA encoding a TCR specific for a bacterial peptide can be isolated from T cells specific for a bacterial polypeptide using standard molecular biological and recombinant DNA techniques.

This invention further includes the T-cell receptors or analogs thereof having substantially the same function or activity as the T-cell receptors of this invention which recognize or bind bacterial polypeptides. Such receptors include, but are not limited to, a fragment of the receptor, or a substitution, addition or deletion mutant of a T-cell receptor provided herein. This invention also encompasses polypeptides or peptides that are substantially homologous to the T-cell receptors provided herein or that retain substantially the same activity. The term "analog" includes any protein or polypeptide having an amino acid residue sequence substantially identical to the T-cell receptors provided herein in which one or more residues, preferably no more than 5 residues, more preferably no more than 25 residues have been conservatively substituted with a functionally similar residue and which displays the functional aspects of the T-cell receptor as described herein.

The present invention further provides for suitable mammalian host cells, for example, non-specific T cells, that are transfected with a polynucleotide encoding TCRs specific for a polypeptide described herein, thereby rendering the host cell specific for the polypeptide. The α and β chains of the TCR may be contained on separate expression vectors or alternatively, on a single expression vector that also contains an internal ribosome entry site (IRES) for cap-independent translation of the gene downstream of the IRES. Said host cells expressing TCRs specific for the polypeptide may be used, for example, for adoptive immunotherapy of IBD as discussed further below.

In further aspects of the present invention, cloned TCRs specific for a polypeptide recited herein may be used in a kit for the diagnosis of IBD. For example, the nucleic acid sequence or portions thereof, of bacterial-specific TCRs can be used as probes or primers for the detection of expression of the rearranged genes encoding the specific TCR in a biological sample. Therefore, the present invention further provides for an assay for detecting messenger RNA or DNA encoding the TCR specific for a polypeptide.

Pharmaceutical Compositions

In additional embodiments, the present invention concerns formulation of one or more of the polynucleotide, polypeptide, T-cell, TCR, and/or antibody compositions disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide, antibody, TCR, and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and theraputic vaccine applications. Vaccine preparation is generally described in, for example, M. F. Powell and M. J. Newman, eds., "Vaccine Design (the subunit and adjuvant approach)," Plenum Press (NY, 1995). Generally, such compositions will comprise one or more polynucleotide and/or polypeptide compositions of the present invention in combination with one or more immunostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, *Crit. Rev. Therap. Drug Carrier Systems* 15:143-198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium. (such as *Bacillus-Calmette-Guerrin*) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; and Rich et al. (1993) Human Gene Therapy 4:461-476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(-) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al. Proc. Natl. Acad. Sci. USA (1986) 83:8122-8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866-6869 and Wagner et al. Proc. Natl. Acad. Sci. USA (1992) 89:6099-6103, can also be used for gene delivery under the invention.

Additional illustrative information on these and other known viral-based delivery systems can be found, for example, in Fisher-Hoch et al., *Proc. Natl. Acad Sci. USA* 86:317-321, 1989; Flexner et al., *Ann. N.Y. Acad Sci.* 569: 86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *Proc. Natl. Acad Sci. USA* 91:215-219, 1994; Kass-Eisler et al., *Proc. Natl. Acad Sci. USA* 90:11498-11502, 1993; Guzman et al., *Circulation* 88:2838-2848, 1993; and Guzman et al., *Cir. Res.* 73:1202-1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., *Science* 259:1745-1749, 1993 and reviewed by Cohen, *Science* 259:1691-1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, antibody, T-cell, TCR, and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an anti-inflammatory immune response (antibody or cell-mediated). Accordingly, high levels of anti-inflammatory cytokines (anti-inflammatory cytokines may include, but are not limited to, interleukin 4 (IL-4), interleukin 5 (IL-5), interleukin 10 (IL-10), and transforming growth factor beta (TGFβ would be preferred. In certain embodiments, an anti-inflammatory response would be mediated by CD4+ T helper cells. Bacterial flagellin have been suggested to act as adjunvants (McSorley et al., *J. Immunol.* 169:3914-19, 2002). Within one embodiment of the invention, the flagellin proteins disclosed herein can be used in adjuvant compositions.

Within other embodiments, the adjuvants used in conjunction with the compositions of the present invention increase lipopolysaccharide (LPS) responsiveness. Illustrative adjuvants include but are not limited to, monophosphoryl lipid A (MPL), aminoalkyl glucosaminide 4-phosphates (AGPs), including RC-512, RC-522, RC-527, RC-529, RC-544, and RC-560 (Corixa, Hamilton, Mont.) and other AGPs such as those described in pending U.S. patent application Ser. Nos. 08/853,826 and 09/074,720, the disclosures of which are incorporated herein by reference in their entireties.

Within other embodiments of the invention, the adjuvant composition is one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145-173, 1989. Alternatively, in a related embodiment, in which a preferred response is predominantly Th2-type, the level of Th2-type cytokines will increase to a greater extent than the level of Th1-type cytokines. Again, the levels of these cytokines may be readily assessed using standard assays.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol® to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula $$HO(CH_2CH_2O)_n\text{-}A\text{-}R, \qquad (I):$$

wherein, n is 1-50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4-24, most preferably 9; the R component is $C_{1-50}$, preferably $C_4$-$C_{20}$ alkyl and most preferably $C_{12}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-bacterial effects per se and/or to be immunologically compatible with the receiver (i.e., matched HLA haplotype). APCs may generally be isolated from any of a variety of biological fluids and organs, including bacterial and peribacterial tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245-251, 1998) and have been shown to be effective as a physiological adjuvant for eliciting prophylactic or therapeutic antibacterial immunity (see Timmerman and Levy, *Ann. Rev. Med.* 50:507-529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med* 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456-460, 1997. Antigen loading of dendritic cells may be achieved by incubating dendritic cells or progenitor cells with the bacterial polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems. such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

In another illustrative embodiment, calcium phosphate core particles are employed as carriers, vaccine adjuvants, or as controlled release matrices for the compositions of this invention. Exemplary calcium phosphate particles are disclosed, for example, in published patent application No. WO/0046147.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature 1997 Mar. 27; 386(6623):410-4; Hwang et al., Crit Rev Ther Drug Carrier Syst 1998; 15(3):243-84; U.S. Pat. No. 5,641,515; U.S. Pat. No. 5,580,579 and U.S. Pat. No. 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release 1998 Mar. 2; 52(1-2):81-7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July; 16(7):307-21; Takakura, Nippon Rinsho 1998 March; 56(3):691-5; Chandran et al., Indian J Exp Biol. 1997 August; 35(8):801-9; Margalit, Crit Rev Ther Drug Carrier Syst. 1995; 12(2-3):233-61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol Chem. 1990 Sep. 25; 265(27):16337-42; Muller et al., DNA Cell Biol. 1990 April; 9(3):221-9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December; 24(12):1113-28). To avoid side effects due to intracellular polymeric overloading, such ultrafine particles (sized around 0.1 μm) may be designed using polymers able to be degraded in vivo. Such particles can be made as described, for example, by Couvreur et al., Crit Rev Ther Drug Carrier Syst. 1988; 5(1):1-20; zur Muhlen et al., Eur J Pharm Biopharm. 1998 March; 45(2):149-55; Zambaux et al. J Controlled Release. 1998 Jan. 2; 50(1-3):31-40; and U.S. Pat. No. 5,145,684.

Therapeutic Methods for IBD

Immunologic approaches to IBD therapy are based on the recognition that IBD represents an "abnormal" mucosal immune response to bacteria within the lumen of the gastrointestinal tract. The precise molecular nature of the bacterial antigen(s) recognized by the immune system has not been described.

IBD immunotherapy generally focuses on inducing humoral immune responses, cellular immune responses, or both, with the goal of inducing tolerance to a particular enteric bacterial antigen, thereby leading to a decrease in inflammation in the gut. Moreover, induction of $CD4^+$ T helper cells is necessary in order to secondarily induce either antibodies or cytotoxic $CD8^+$ T cells. Polypeptide antigens that are selective or ideally specific to IBD-associated bacteria offer a powerful approach for inducing anti-inflammatory immune responses that either prevent or ameliorate an aberrant immune response to bacterial antigens associated with IBD, and are an important aspect of the present invention.

Therefore, in further aspects of the present invention, the pharmaceutical compositions described herein may be used to stimulate an immune response against bacterial antigens associated with IBD. In one embodiment of the present invention, the immune response induced comprises antibodies that block the interaction of a bacterial antigen with a host receptor. In one particular embodiment, antibodies induced by the compositions of the present invention block the interaction between flagellin and TLR5, thereby ameliorating the pro-inflammatory cascade initiated by NFKB activation. Alternatively, the compositions of the present invention would induce antibodies that stimulate responsiveness to LPS that ameliorated the hypo-responsiveness in individuals with Nod2 gene mutation associated with IBD.

In a further embodiment of the present invention, an immune response would be anti-inflammatory in nature. For example, a cellular immune response wherein the T cells produce anti-inflammatory cytokines. Anti-inflammatory cytokines may include, but are not limited to, IL-4, IL-5, IL-10, TGF-β.

Within such methods, the pharmaceutical compositions described herein are administered to a patient, typically a warm-blooded animal, preferably a human. A patient may or may not be afflicted with IBD. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against bacteria with the administration of immune response-modifying agents or immunomodulators (such as polypeptides and polynucleotides as provided herein).

Within other embodiments, immunotherapy may be passive immunotherapy, in which treatment involves the delivery of agents with established antibacterial immune reactivity (such as effector cells or antibodies) that can directly or indirectly mediate antibacterial effects and does not necessarily depend on an intact host immune system. Examples of effector cells include T cells as discussed above, T lymphocytes (such as $CD8^+$ cytotoxic T lymphocytes and $CD4^+$ T-helper lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Monoclonal antibodies may be labeled with any of a variety of labels for desired selective usages in detection, diagnostic assays or therapeutic applications (as described in U.S. Pat. Nos. 6,090,365; 6,015,542; 5,843,398; 5,595,721; and 4,708,930, hereby incorporated by reference in their entirety as if each was incorporated individually). In each case, the binding of the labelled monoclonal antibody to the determinant site of the antigen will signal detection or delivery of a particular therapeutic agent to the antigenic determinant on the non-normal cell. A further object of this invention is to provide the specific monoclonal antibody suitably labelled for achieving such desired selective usages thereof.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an appropriate anti-bacterial immune response, and is at least 10-50% above the basal (i.e., untreated) level. Alternatively, a suitable dose is an amount of a compound that, when administered as described above, is capable of decreasing inflammation in the colon associated with IBD. Such a decrease is at least 10-50% below the untreated level. Such response can be monitored by measuring the anti-bacterial antibodies in a patient or by vaccine-dependent generation of cytolytic effector cells capable of recognizing in vitro bacterial antigens identified from bacteria isolated from the patient. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 μg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., a decrease in inflammation in the gut, decrease in diarrhea, decrease in steroid requirements or requirement for other immunosuppressive therapies, decrease in anemia, or decrease in Crohn's disease activity index (CDAI)) in treated patients as compared to non-treated patients. Increases in appropriate anti-inflammatory immune responses to a bacterial protein generally correlate with an improved clinical outcome. Such immune responses may generally be evaluated using standard proliferation, cytotoxicity or cytokine assays, which may be performed using samples obtained from a patient before and after treatment.

Detection and Diagnostic Compositions, Methods and Kits

There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of an IBD-associated bacteria in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length bacterial proteins and polypeptide portions thereof to which the binding agent binds, as described above.

The solid support may be any material known to those of ordinary skill in the art to which the bacterial protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of an IBD-associated bacterial polypeptide within a sample obtained from an individual with IBD at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of IBD, the signal detected from the reporter group that remains bound to the solid support is generally compared to a signal that corresponds to a predetermined cut-off value. In one preferred embodiment, the cut-off value for the detection of an IBD-associated bacterial antigen is the average mean signal obtained when the immobilized antibody is incubated with samples from patients without IBD. In general, a sample generating a signal that is three standard deviations above the predetermined cut-off value is considered positive for IBD-associated bacterial antigens. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for an IBD-associated bacteria.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of an IBD-associated bacterial antigen. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 μg, and more preferably from about 50 ng to about 500 ng. Such tests can typically be performed with a very small amount of biological sample.

Of course, numerous other assay protocols exist that are suitable for use with the bacterial proteins or binding agents of the present invention. The above descriptions are intended to be exemplary only. For example, it will be apparent to those of ordinary skill in the art that the above protocols may be readily modified to use bacterial polypeptides to detect antibodies that bind to such polypeptides in a biological sample. The detection of such bacterial protein specific antibodies may correlate with the presence of an IBD-associated antigen.

IBD-associated bacteria may also, or alternatively, be detected based on the presence of T cells that specifically react with a bacterial protein in a biological sample. Within certain methods, a biological sample comprising $CD4^+$ and/or $CD8^+$ T cells isolated from a patient is incubated with a bacterial polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). In one particular embodiment of the present invention, T cells may be isolated from intraepithelial lymphocytes (IEL) or lamina propria lymphocyte (LPL) samples originating from colon biopsies. T cells may be incubated in vitro for 2-9 days (typically 4 days) at 37 □C with polypeptide (e.g., 5-25 μg/ml). It may be desirable to incubate another aliquot of a T cell sample in the absence of bacterial polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of IBD-associated bacteria in the patient.

As noted above, IBD may also, or alternatively, be detected based on the level of mRNA encoding a bacterial protein in a biological sample. For example, at least two oligonucleotide primers may be employed in a polymerase chain reaction (PCR) based assay to amplify a portion of a bacterial cDNA derived from a biological sample, wherein at least one of the oligonucleotide primers is specific for (i.e., hybridizes to) a polynucleotide encoding the bacterial protein. The amplified cDNA is then separated and detected using techniques well known in the art, such as gel electrophoresis.

Similarly, oligonucleotide probes that specifically hybridize to a polynucleotide encoding a bacterial protein may be used in a hybridization assay to detect the presence of polynucleotide encoding the bacterial protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a bacterial protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10-40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, N Y, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of IBD. In this embodiment, assays as described above for the diagnosis of IBD may be performed over time, and the change in the level of reactive polypeptide(s) or polynucleotide(s) evaluated. For example, the assays may be performed every 24-72 hours for a period of 6 months to 1 year, and thereafter performed as needed. In general, IBD is progressing in those patients in whom the level of polypeptide or polynucleotide detected increases over time. In contrast, IBD is not progressing when the level of reactive polypeptide or polynucleotide either remains constant or decreases with time.

In a further embodiment, the compositions described herein may be used to monitor the level of antibodies specific for and/or T cell responsiveness to an IBD-associated bacterial protein as a measure of IBD progression. In general, IBD is progressing in those patients in whom the level of antibodies that bind to a polypeptide or encoded by a polynucleotide described herein, that are detected increases over time. In contrast, IBD is not progressing when the level of reactive antibodies either remains constant or decreases with time.

Certain in vivo diagnostic assays may be performed directly on a lesion in the colon. One such assay involves contacting cells from a lesion with a binding agent. The bound binding agent may then be detected directly or indirectly via a reporter group. Such binding agents may also be used in histological applications. Alternatively, polynucleotide probes may be used within such applications.

As noted above, to improve sensitivity, multiple bacterial proteins may be assayed within a given sample. It will be apparent that binding agents specific for different proteins, antibodies, or T cells specific thereto provided herein may be combined within a single assay. Further, multiple primers or probes may be used concurrently. The selection of bacterial proteins may be based on routine experiments to determine combinations that results in optimal sensitivity. In addition, or alternatively, assays for bacterial proteins, antibodies, or T cells specific thereto, provided herein may be combined with assays for other known bacterial antigens or genetic markers such as the NOD2 mutation.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a bacterial protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a bacterial protein in a biological sample. Such kits generally comprise at least one oligonucleotide probe or primer, as described above, that hybridizes to a polynucleotide encoding a bacterial protein. Such an oligonucleotide may be used, for example, within a PCR or hybridization assay. Additional components that may be present within such kits include a second oligonucleotide and/or a diagnostic reagent or container to facilitate the detection of a polynucleotide encoding a bacterial protein.

In an alternative embodiment, a kit may be designed to detect the level of antibodies specific for an IBD-associated bacterial protein in a biological sample.

The following Examples are offered by way of illustration and not by way of limitation.

EXAMPLES

Example 1

Identification of IBD-Associated Bacterial Antigens from a Mouse Cecal Bacteria Genomic Random Shear Expression Library A mouse cecal bacteria genomic random shear expression library was constructed by sonicating C3H/HeJ Bir mouse cecal bacteria genomic DNA to produce fragment sizes of approximately 0.1 to 5.0 kbp. 14 μg of sonicated DNA was treated with DNA polymerase I, Klenow fragment, for 30 minutes followed by Pfu polymerase for 30 minutes to produce blunt ended fragments. EcoRI adaptors were then ligated to the fragments and then adaptors were phosphorylated with *E. coli* polynucleotide kinase. Fragments were next fractionated with a Sephacryl S400 column and finally ligated to a Lambda ZAP Express (Stratagene) vector. Ligated vector was then packaged with Gigapack III Gold packaging extract (Stratagene) and the unamplified library was plated with host *E. coli* XL-1 Blue MRF' cells on LB agarose plates at a concentration of 25,000 plaque forming units (PFU) per plate for 15 plates. After incubation at 42'C for 4 hours, nitrocellulose filters, soaked in 10 mM IPTG, were added and the plates which were incubated at 37° C. over night. Filters were removed and washed 3× with PBS containing 0.1% Tween 20 (PBST), blocked for 1 hour with 1% BSA in PBST, washed 3× with PBST and then incubated overnight at 4'C in serum, preadsorbed with *E. coli* proteins, from C3H/HeJ Bir mice with inflammatory bowel disease. After washing 3× with PBST, filters were incubated in a goat anti-mouse IgG, IgA, IgM secondary antibody conjugated with alkaline phosphatase for 1 hour at room temperature. Filters were finally washed 3× with PBST, 2× with alkaline phosphatase buffer and developed with BCIP/NBT. Positive clones were purified using the same technique; phagemid was excised; and resulting plasmid DNA was sequenced and searched against the GenBank databases. Those sequences that showed some degree of similarity to known sequences in the database are listed in Table 2. Those sequences that showed no significant similarity to known sequences in the database are shown in Table 3.

TABLE 2

BACTERIAL SEQUENCES THAT SHOWED SOME DEGREE OF SIMILARITY TO KNOWN SEQUENCES IN THE DATABASE

| cDNA SEQ ID | PRO SEQ ID | Clone Name | Clone ID | Insert kbp | Blastn | Blastx |
|---|---|---|---|---|---|---|
| 1 | 38 | Cbir-1 | 76779 | 1.3 | No match | (73%) flagellin A protein/ (48%) FlaB [*Butyrivibrio fibrisolvens*] (AF026812) |
| 2 | 39 | Cbir-2 | 76780 | 0.4 | No match | (73%) 3-isopropylmalate dehydrogenase VC2491-*Vibrio cholerae* (group O1 strain N16961) |
| 3 | 40, 41 | Cbir-3 | 76959 | 0.8 | No match | (53%) motility protein A-*Termotoga maritima* (strainMSB8) |
| 5 | | Cbir-5 | 76961 | 1.2 | No match | (44%) methyl-accepting chemotaxis protein [*Bacillus halodurans*] (AP001520) |
| 6 | 42 | Cbir-6 | 76781 | 1.0 | No match | (56%) ribosomal protein L6 (BL10) |
| 7 | | Cbir-8 | 76962 | 3.0 | No match | (60%) acetohydroxy acid synthase large chain-*Brevibacterium flavum* |
| 10 | | Cbir-12 | 76964 | 2.0 | (82%) Same as Blastx | (58%) phosphoenolpyruvate carboxykinase VC2738-*Vibrio cholerae* (group O1 strain N16961) |
| 12 | | Cbir-14 | 76965 | 1.7 | No match | (49%) gap regulator [*Staphylococcus aureus*] (AJ133520) |
| 13 | | Cbir-15 | 76966 | 1.0 | (82%) Same as Blastx | (72%) flagellin A protein/ FlaB (*Butyrivibrio fibrisolvens*) (AF026812) |
| 14 | 44 | Cbir-16 | 76967 | 1.2 | No match | (58%) ribosomal protein L6 (BL10) |
| 15 | | Cbir-18 | 76968 | 0.8 | No match | (69%) flagellin - *Roseburia cecicola* (65%) flagellin A protein/ (63%) FlaB [*Butyrivibrio fibrisolvens*] (AF026812) |
| 16 | | Cbir-19 | 77530 | 1.6 | No match | (51%) ABC-type transport protein-*Synechocystis* sp. (strain PCC6803) |
| 17 | 45 | Cbir-20 | 76969 | 2.0 | No match | (68%) FlaB [*Butyrivibrio fibrisolvens*] (AF026812) |
| 18 | | Cbir-23 | 76970 | 0.8 | (80%) Same as Blastx | (84%) elongation factor-Tu [*Porphyromonas gingivalis*] (AB035462) |
| 23 | 47 | Cbir-32 | 76974 | 65 bp | No match | probably amidohydrolase *Campylobacter jenjuni* (strain NCTC 11168) |
| 24 | | Cbir-36 | 77074 | 1.6 | (87%) *Bacillus subtilis* complete genome | (83%) elongation factor TU-I (*Streptomyces ramocissimus*) |
| 26 | 48 | Cbir-39 | 76975 | 0.6 | No match | (70%) *Thermotoga maritima* (strainMSB8) (55%) flagellin A protein/ (56%) FlaB [*Butyrivibrio fibrisolvens*] (AF026812) |
| 27 | | Cbir-40 | 77075 | 0.7 | No match | (54%) flagellin-*Thermotoga maritima* (strain MSB8)/ (58%) flagellin (*Bacillus halodurans*) (AP001512) |
| 29 | 49 | Cbir-44 | 76977 | 1.0 | No match | (45%) flagellin-*Thermotoga maritima* (strainMSB8)/ (57%) flagellin (*Bacillus halodurans*) (AP001512) |
| 31 | | Cbir-46 | 77533 | 2.2 | No match | (AL512975) |
| 32 | | Cbir-49 | 77534 | 0.9 | No match | (59%) flagellin-*Roseburia cecicola* (56%) flagellin A protein/ (58%) FlaB (*Butyrivibrio fibriosolvens*) (AF026812) |

TABLE 2-continued

BACTERIAL SEQUENCES THAT SHOWED SOME DEGREE OF SIMILARITY TO KNOWN SEQUENCES IN THE DATABASE

| cDNA SEQ ID | PRO SEQ ID | Clone Name | Clone ID | Insert kbp | Blastn | Blastx |
|---|---|---|---|---|---|---|
| 35 | | Cbir-62 | 77536 | 0.6 | No match | hemolysin secretion protein precursor-*Helecobacter pylori* (strain 26695)/ methyl-accepting chemotaxis protein (*Helecobacter pylori*) |
| 36 | | Cbir-73 | 77538 | 2.0 | No match | elongation factor - TS |
| 37 | | Cbir-78 | 77539 | 1.0 | No match | (62%) flagellin-*Roseburia cecicola* (M20983) (57%) flagellin A protein/ (59%) FlaB (*Butyrivibrio fibrisolvens*) |
| 51 | | CB1-T2 | 73261 | 150 | No match | 36% *Streptomyces* Arabinosidase Secreted |
| 54 | | CB1-T5 | 73264 | 1050 | No match | 33% *Arabidopsis* ClpC protease |
| 55 | | CB1-T7 | 73266 | 650 | No match | 54% *S. cerevisiae* Acetyltransferase |
| 56 | | CB1-T8 | 73267 | 350 | No match | 28% *Bacillus subtilis* Unknown |
| 58 | | CB1-T10 | 73269 | 150 | No match | ? 40% *Deinococcus* ABC transporter |
| 59 | | CB1-T11 | 73270 | 1700 | No match | 52% *Borrelia burgdorferi* Fructose-6-p 1-phosphotransferase |
| 60 | | CB1-T13 | 73272 | 250 | No match | 56% *Vibrio*/*Clostridium* alcohol dehydrogenase |
| 61 | | CB1-T14 | 73273 | 260 | No match | ? 53% *Bacteroides* surface Ag BspA |
| 62 | | CB1-T15 | 73274 | 1000 | No match | 61% *Clostridium* prolyl tRNA synthetase |
| 64 | | CB3-T1 | 75037 | 1.7 | ? 88% *strepto-myces* | 65% *Bacillus subtilis* oligopeptide transport ATP-bind pro OPPF |
| 67 | | CB3-T4 | 75040 | ?>600 | No match | 36% *E. coli*/Staph Hypothetical 14.8 kDa membrane protein |
| 70 | | CB3-T9 | 75044 | 300 | No match | 91% *Helicobacter pylolri* 2,3,4,5-tetrahydropyridine-2-carboxylaten-succinyltransferase |
| 72 | | CB3-T12 | 75046 | 1700 | No match | 52% *Thermotoga*/ *Archaeoglobus*/ *Halobacterium* conserved prot. |
| 74 | | CB3-T14 | 75048 | 1300 | No match | 29% *Streptomyces* heat shock |

TABLE 3

BACTERIAL SEQUENCES THAT SHOWED NO SIGNIFICANT SIMILARITY TO KNOWN SEQUENCES IN THE DATABASE

| CDNA SEQ ID | PRO SEQ ID | Clone Name | Clone ID | Insert kbp | Blastn | Blastx |
|---|---|---|---|---|---|---|
| 4 | | Cbir-4 | 76960 | 2.1 | No match | No match |
| 8 | 43 | Cbir-9 | 76782 | 0.6 | No match | No match |
| 9 | | Cbir-11 | 76963 | 1.5 | No match | No match |
| 11 | | Cbir-13 | 77529 | 1.5 | No match | No match |
| 19 | | Cbir-24 | 76971 | 2.3 | No match | No match |
| 20 | | Cbir-26 | 77073 | 1.2 | No match | No match |
| 21 | 46 | Cbir-27 | 76972 | 0.5 | No match | No match |
| 22 | | Cbir-30 | 76973 | 0.7 | No match | No match |
| 25 | | Cbir-37 | 77531 | 2.5 | No match | No match |
| 28 | | Cbir-41 | 76976 | 1.2 | No match | No match |

TABLE 3-continued

BACTERIAL SEQUENCES THAT SHOWED NO SIGNIFICANT SIMILARITY TO KNOWN SEQUENCES IN THE DATABASE

| CDNA SEQ ID | PRO SEQ ID | Clone Name | Clone ID | Insert kbp | Blastn | Blastx |
|---|---|---|---|---|---|---|
| 30 | | Cbir-45 | 77532 | 1.2 | No match | No match |
| 33 | | Cbir-50 | 77535 | 0.7 | No match | No match |
| 34 | 50 | Cbir-61 | 77076 | 0.5 | No match | No match |
| 52 | | CB1-T3 | 73262 | 600 | No match | No match |
| 53 | | CB1-T4 | 73263 | 250 | No match | No match |
| 57 | | CB1-T9 | 73268 | 250 | No match | No match |
| 63 | | CB1-T16 | 73275 | 400 | No match | No match |
| 65 | | CB3-T2 | 75038 | 500 | No match | No match |
| 66 | | CB3-T3 | 75039 | 500 | No match | No match |
| 68 | | CB3-T5 | 75041 | 400 | No match | No match |

TABLE 3-continued

| BACTERIAL SEQUENCES THAT SHOWED NO SIGNIFICANT SIMILARITY TO KNOWN SEQUENCES IN THE DATABASE | | | | | | |
|---|---|---|---|---|---|---|
| CDNA SEQ ID | PRO SEQ ID | Clone Name | Clone ID | Insert kbp | Blastn | Blastx |
| 69 | | CB3-T6 | 75042 | 600 | No match | No match |
| 71 | | CB3-T10 | 75045 | ?>500 | No match | No match |
| 73 | | CB3-T13 | 75047 | 700 | No match | No match |

Example 2

Cloning and Expression of Flagellin X

A novel flagellin was cloned by PCR amplification from total cecal bacterium genomic DNA obtained from C3H/HeJ Bir mice. Oligonucleotide primers were developed with sequence from the amino terminus of clone Cbir-1 (SEQ ID NO:1) and with a consensus sequence derived from the carboxy terminus of three flagellin sequences that are most closely related the Cbir-1 sequence. A six histidine tag and a Nde I endonuclease cleavage site were added to the amino primer for cloning and for purification of recombinant protein and a Hind II cloning site was added to the carboxy-terminal primer. The full-length Flagellin X cDNA sequence (SEQ ID NO:75) was expressed as a pET17b (Novagen, Madison, Wis.) construct and resulting recombinant protein was purified with a Ni-NTA affinity column (Qiagen, Valencia, Calif.). The full length amino acid sequence of Flagellin X is represented in SEQ ID NO:79. Both Western blot analysis and ELISA assays demonstrated that this recombinant flagellin protein was reactive with antibody from mice with IBD.

Three truncated forms of Flagellin X were constructed and used in expression studies. The following truncations were cloned using PCR primers developed from the flagellin X sequence:

i. the amino terminal conserved end of the molecule (cDNA sequence:SEQ ID NO:76, amino acid sequence: SEQ ID NO:80)

ii. the amino terminal conserved end plus the variable portion of the molecule (cDNA sequence: SEQ ID NO:77, amino acid sequence: SEQ ID NO:81)

iii. and the carboxy-terminal conserved portion (cDNA sequence: SEQ ID NO:78, amino acid sequence: SEQ ID NO:82)

A six histidine tag and cloning sites were added to all constructs for cloning and expression with the pET17b vector. The constructs were expressed in *E. coli* and recombinant protein analyzed by Western blot and ELISA. Western blot and ELISA assays with amino terminal and carboxy terminal recombinant protein demonstrated that the greatest antibody reactivity was to the conserved amino terminus. These recombinant proteins have utility in the diagnosis, therapy, and vaccine development for IBD.

Example 3

Identification of the Full-Length Nucleotide and Polypeptide Sequence of *Heucobacter Bilis* Flagelin B This example describes the identification of the full-length *H. bilis* flagellin B nucleotide and polypeptide sequence. The recombinant DNA and protein sequences have utility, for example, in the diagnosis, therapy, and vaccine development for IBD.

Infection with *Helicobacter* spp, including *H. bilis*, has been reported to cause IBD in immunodeficient mice. Thus *Helicobacter* spp and specific *Helicobacter* proteins are useful tools for investigating microbial-induced IBD. *Helicobacter* spp, especially *H. pylori*, have also been implicated in human IBD. As shown in Examples 1 and 2 herein, bacterial flagellin are believed to be associated with IBD in the mouse model. Described herein are the nucleotide and polypeptide sequences for *H. bilis* flagellin B (FlaB). This sequence was amplified using standard techniques from *H. bilis* total genomic DNA using oligonucleotide primers derived from the *H. mustelae* flagellin B sequence. The full-length nucleotide sequence (coding sequence) of the *H. bilis* flagellin B is set forth in SEQ ID NO:83. The amino acid sequence encoded by this nucleotide is set forth in SEQ ID NO:84. This polypeptide showed homology to *H. mustelae* and *H. pylori* flagellin B proteins. The amino terminal conserved region of the *H. bilis* flagillin B protein includes amino acid residues 1 to 154 of SEQ ID NO:84, and the corresponding nucleotides that encode this region from SEQ ID NO:83. The carboxy-terminal conserved portion includes amino acid residues 365 to 514 of SEQ ID NO:84, and the corresponding nucleotides that encode this region from SEQ ID NO:83. In summary, these sequences represent attractive therapeutic and diagnostic targets for IBD.

Example 4

Identification of the Full-Length Nucleotide and Protein Sequence of CBIR-1 Flagelin This example describes the full-length sequencing of the Cbir-1 flagellin clone (partial sequence set forth in SEQ ID NO:1). This clone was originally obtained by serologic expression screening a mouse cecal bacterium library with serum from mice with IBD (see Example 1 and Table 2). The recombinant DNA and protein sequences have utility, for example, in the diagnosis, therapy, and vaccine development for IBD.

The Cbir-1 clone is a partial bacterial flagellin sequence (amino end plus variable region) that was shown to be highly reactive with the mouse serum used to screen the bacterial library. Recombinant protein derived from this clone and a recombinant representing the amino terminus of this cloned sequence were also highly reactive with diseased mouse (IgG2a) and human serum and also potentially contain a T cell epitope. These data indicate that this protein is immunogenic in mouse and in human. Described herein are the full-length CBir-1 flagellin nucleotide (SEQ ID NO:85) and protein (SEQ ID NO:86) sequences. The nucleotide sequence was obtained by standard PCR amplification techniques from total genomic mouse cecal bacterial DNA with a primer specific for Clone CBir-1 sequence and a second primer derived from the conserved carboxy end of related flagellin sequences. Polypeptide alignments confirmed that the protein is related to other flagellin proteins. The amino terminal conserved region of the CBir-1 protein includes amino acid residues 1 to 147 of SEQ ID NO:86, and the corresponding nucleotides that encode this region from SEQ ID NO:85. The amino terminal conserved end plus the variable portion of the molecule includes amino acid residues 1 to 418 of SEQ ID NO:86 and the corresponding nucleotides that encode this region from SEQ ID NO:85. The carboxy-terminal conserved portion includes amino acid residues 361 to 493 of SEQ ID NO:86, and the corresponding nucleotides that encode this region from SEQ ID NO:85. Thus, in summary, these sequences represent attractive therapeutic and diagnostic targets for IBD.

FIG. 1 shows a schematic of flagellin clones with percent similarity to related flagellin B from the rumen anaerobe, *Butyrivibrio fibrisolvens*. (A) Structure of *B. fibrisolvens* flagellin A showing conserved amino and carboxyl regions and the hyper-variable central domain. (B) Mapping of the predicted amino acid sequences from the flagellin expression clones (1-12) in relation to the *B. fibrisolvens* sequence. Percentage range (41-84%) indicates the similarity in $NH_2$-conserved sequence between the clone and *B. fibrisolvens* sequences. (C) Diagram of the full-length amino acid sequence of mouse cecal bacteria flagellins cBir-1 and Flax indicating the similarity of the three domains with the respective *B. fibrisolvens* domains. (D, E) Schematics of recombinant flagellin proteins and fragments for cBir-1 (D) and Flax (E) that have been expressed and purified in *E. coli* by 6-histidine tag affinity to NiNTA columns (Qiagen Corp.).

Example 5

Peptide Priming of T-Helper Lines

Generation of $CD4^+$ T helper lines and identification of peptide epitopes derived from bacterial-specific antigens that are capable of being recognized by $CD4^+$ T cells in the context of HLA class II molecules, is carried out as follows:

Fifteen-mer peptides overlapping by 10 amino acids, derived from a bacterial-specific antigen, are generated using standard procedures. Dendritic cells (DC) are derived from PBMC of a normal donor using GM-CSF and IL-4 by standard protocols. $CD4^+$ T cells are generated from the same donor as the DC using MACS beads (Miltenyi Biotec, Auburn, Calif.) and negative selection. DC are pulsed overnight with pools of the 15-mer peptides, with each peptide at a final concentration of 0.25 μg/ml. Pulsed DC are washed and plated at $1\times10^4$ cells/well of 96-well V-bottom plates and purified $CD4^+$ T cells are added at $1\times10^5$/well. Cultures are supplemented with 60 ng/ml IL-6 and 10 ng/ml IL-12 and incubated at 37° C. Cultures are restimulated as above on a weekly basis using DC generated and pulsed as above as antigen presenting cells, supplemented with 5 ng/ml IL-7 and 10 U/ml IL-2. Following 4 in vitro stimulation cycles, resulting $CD4^+$ T cell lines (each line corresponding to one well) are tested for specific proliferation and cytokine production in response to the stimulating pools of peptide with an irrelevant pool of peptides used as a control.

Example 6

Generation of Bacterial-Specific CTL Lines Using in Vitro Whole-Gene Priming

Using in vitro whole-gene priming with bacterial antigen-vaccinia infected DC (see, for example, Yee et al, *The Journal of Immunology,* 157(9):4079-86, 1996), human CTL lines are derived that specifically recognize autologous fibroblasts transduced with a specific bacterial antigen, as determined by interferon-γ ELISPOT analysis. Specifically, dendritic cells (DC) are differentiated from monocyte cultures derived from PBMC of normal human donors by growing for five days in RPMI medium containing 10% human serum, 50 ng/ml human GM-CSF and 30 ng/ml human IL-4. Following culture, DC are infected overnight with bacterial antigen-recombinant vaccinia virus at a multiplicity of infection (M.O.I) of five, and matured overnight by the addition of 3 μg/ml CD40 ligand. Virus is then inactivated by UV irradiation. CD8+ T cells are isolated using a magnetic bead system, and priming cultures are initiated using standard culture techniques. Cultures are restimulated every 7-10 days using autologous primary fibroblasts retrovirally transduced with previously identified bacterial antigens. Following four stimulation cycles, CD8+ T cell lines are identified that specifically produce interferon-γ when stimulated with bacterial antigen-transduced autologous fibroblasts. Using a panel of HLA-mismatched B-LCL lines transduced with a vector expressing a bacterial antigen, and measuring interferon-γ production by the CTL lines in an ELISPOT assay, the HLA restriction of the CTL lines is determined.

Example 7

Generation and Characterization of Anti-Bacterial Antigen Monoclonal Antibodies

Mouse monoclonal antibodies are raised against *E. coli* derived bacterial antigen proteins as follows: Mice are immunized with Complete Freund's Adjuvant (CPA) containing 50 μg recombinant bacterial protein, followed by a subsequent intraperitoneal boost with Incomplete Freund's Adjuvant (IFA) containing 10 μg recombinant protein. Three days prior to removal of the spleens, the mice are immunized intravenously with approximately 50 μg of soluble recombinant protein. The spleen of a mouse with a positive titer to the bacterial antigen is removed, and a single-cell suspension made and used for fusion to SP2/O myeloma cells to generate B cell hybridomas. The supernatants from the hybrid clones are tested by ELISA for specificity to recombinant bacterial protein, and epitope mapped using peptides that spanned the entire bacterial protein sequence. The mAbs are also tested by flow cytometry for their ability to detect bacterial protein on the surface of cells stably transfected with the cDNA encoding the bacterial protein.

Example 8

Synthesis of Polypeptides

Polypeptides are synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence is attached to the amino terminus of the peptide to provide a method of conjugation, binding to an immobilized surface, or labeling of the peptide. Cleavage of the peptides from the solid support is carried out using the following cleavage mixture: trifluoroacetic acid:ethanedithiol:thioanisole:water:phenol (40:1:2:2:3). After cleaving for 2 hours, the peptides are precipitated in cold methyl-t-butyl-ether. The peptide pellets are then dissolved in water containing 0.1% trifluoroacetic acid (TFA) and lyophilized prior to purification by C18 reverse phase HPLC. A gradient of 0%-60% acetonitrile (containing 0.1% TFA) in water (containing 0.1% TFA) is used to elute the peptides. Following lyophilization of the pure fractions, the peptides are characterized using electrospray or other types of mass spectrometry and by amino acid analysis.

Example 9

Figure 2A:
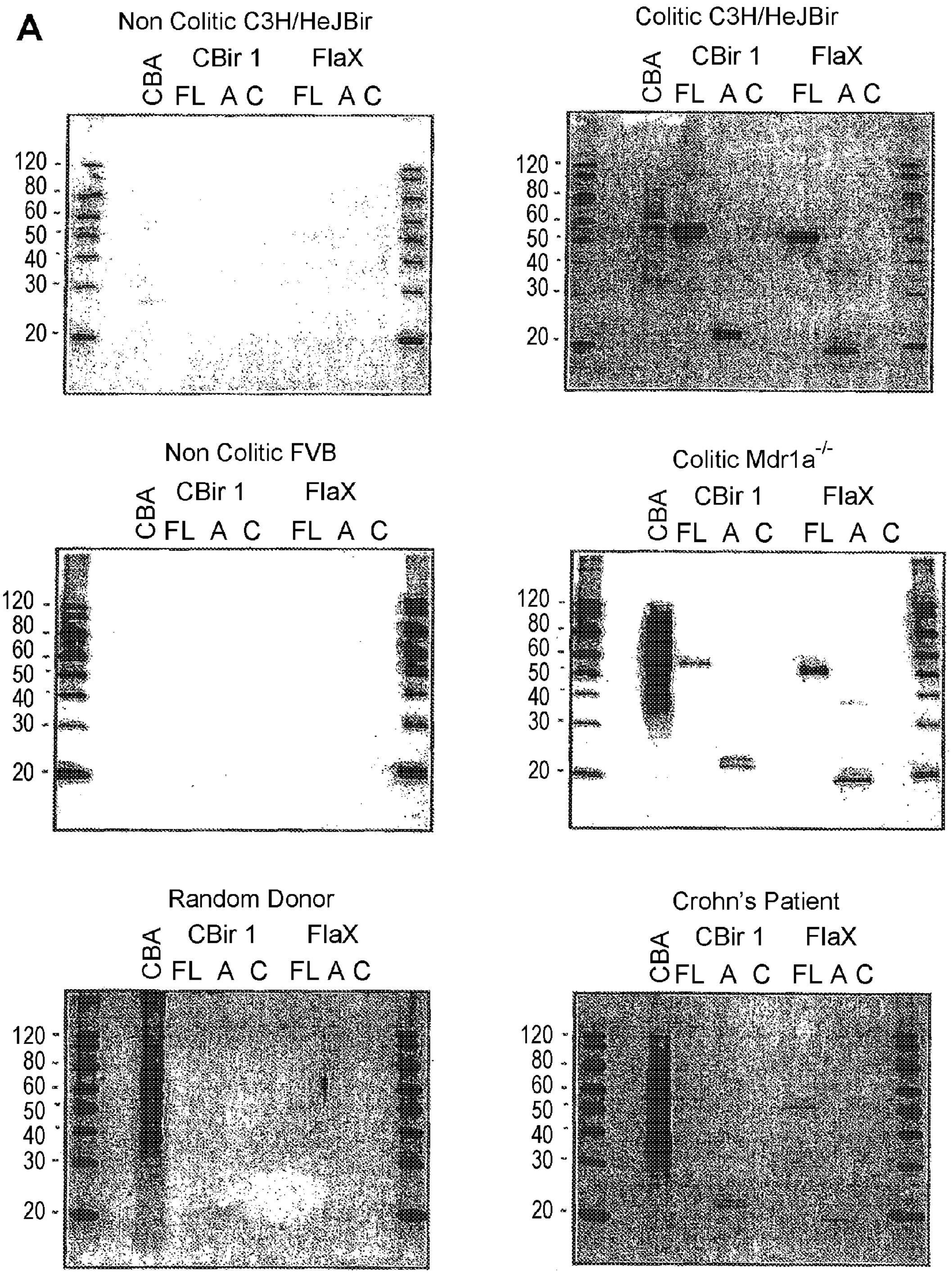
FIG. 2*a* shows Western Blot analysis of serum antibody response to recombinant flagellins cBir-1 and $Fla^X$ and fragments.

Flagellin-Reactive Antibody in Serum from Colitic Mice and its Relationship to Pathology Serum antibody response to recombinant flagellins cBir-1 and $Fla^X$ and fragments were determined by Western blot analysis. One hundred micrograms of full length protein (FL) as well as the amino conserved region (A) and the conserved carboxyl region (C) fragments were subjected to SDS-PAGE separation, transfered to membrane and subjected to serum from non-colitic (pool of 2) and colitic C3H/HeJBir (pool of 5) mice. A second experiment was performed using 20 ng recombinant protein and serum from non-colitic FVB (pool of 5) and colitic $Mdr1a^{-/-}$ (pool of 5) mice. Human samples were used in a third experiment. Random human blood donor and a Crohn's patient with severe disease were run against 50 ng of recombinant protein. The results of these Western Blot analyses are shown in FIG. 2*a*. Mouse cecal bacteria antigens (CBA) was used as a control.

Figure 2B:
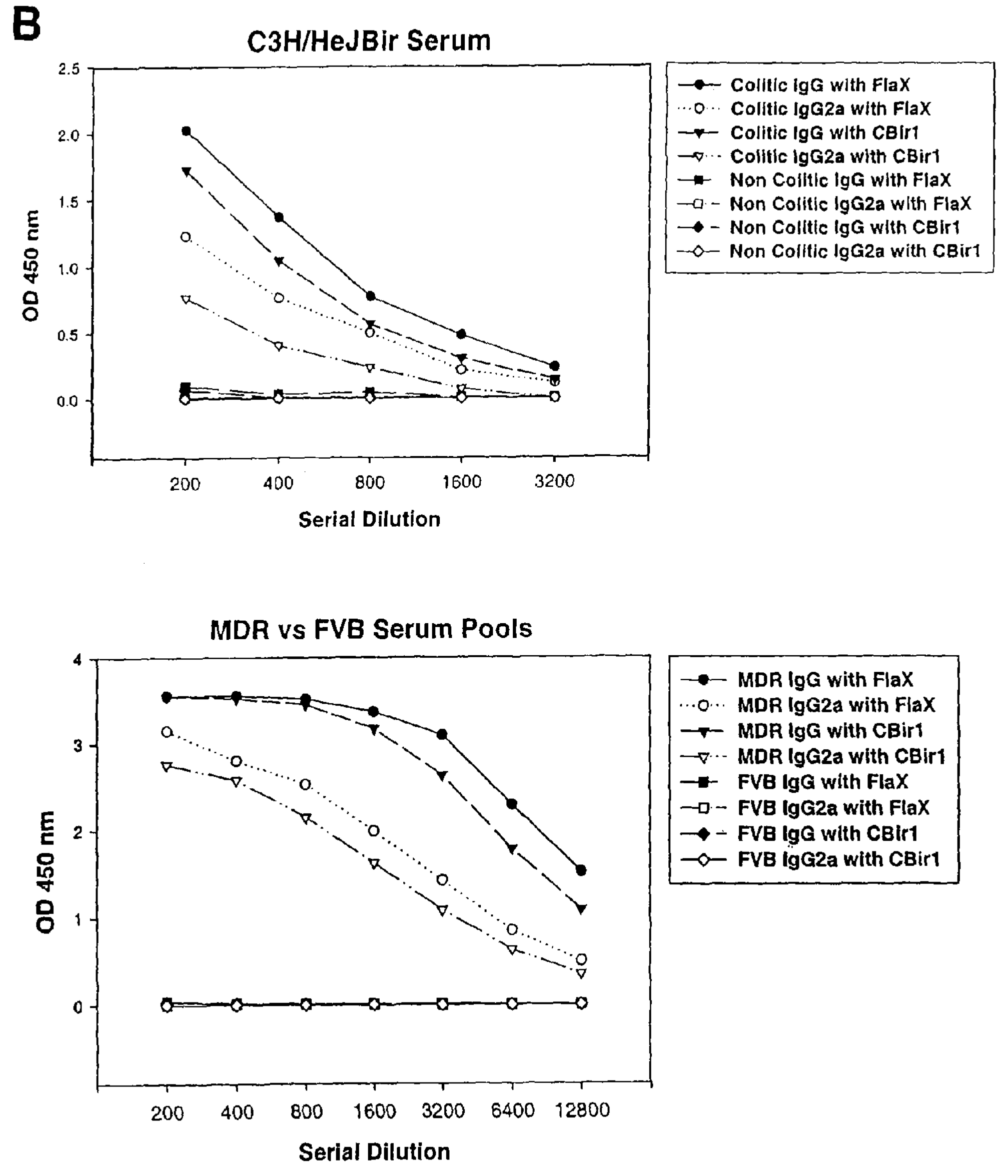
FIG. 2*b* shows titration of serum anti-flagellin antibody against recombinant flagellins cBir-1 and $Fla^X$.

FIG. 2*b* shows titration of serum anti-flagellin antibody against recombinant flagellins cBir-1 and FlaX with secondary antibodies specific for mouse IgG and IgG2a antibodies. Serum from colitic mice (pool of 5) versus non-colitic C3H/HeJBir mice (pool of 2) was used in the upper panel and serum from colitic MDR mice (pool of 5) versus non-colitic FVB (pool of 5) mice was used in the lower panel.

Figure 2C:
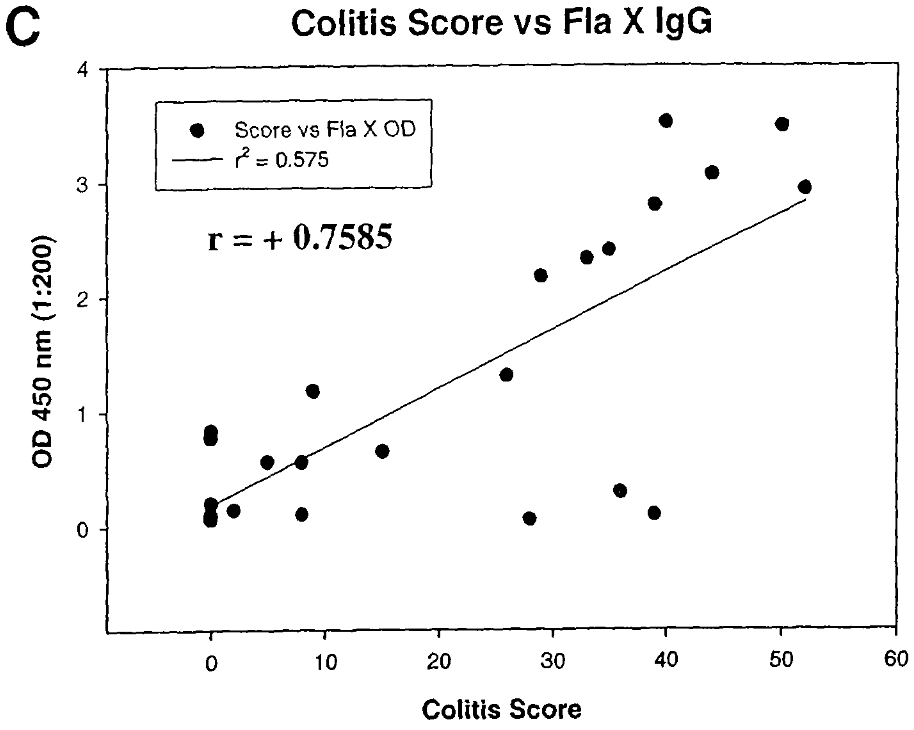
FIG. 2*c* shows the correlation of colitis score with serum anti-$Fla^X$.

FIG. 2*c* shows the correlation of colitis score with serum anti-Flax antibody at a dilution of 1:200 (r=+0.7585). Correlations were also determined for mouse age versus colitis score (r=+0.3716), and mouse age versus anti-flagellin OD 450 at a 1:200 dilution (r=+0.3253). Colitis scores were based on the following scale: No disease (0-2); mild disease (3-15); moderate disease (16-35); and severe disease (≥36).

Figure 2D:
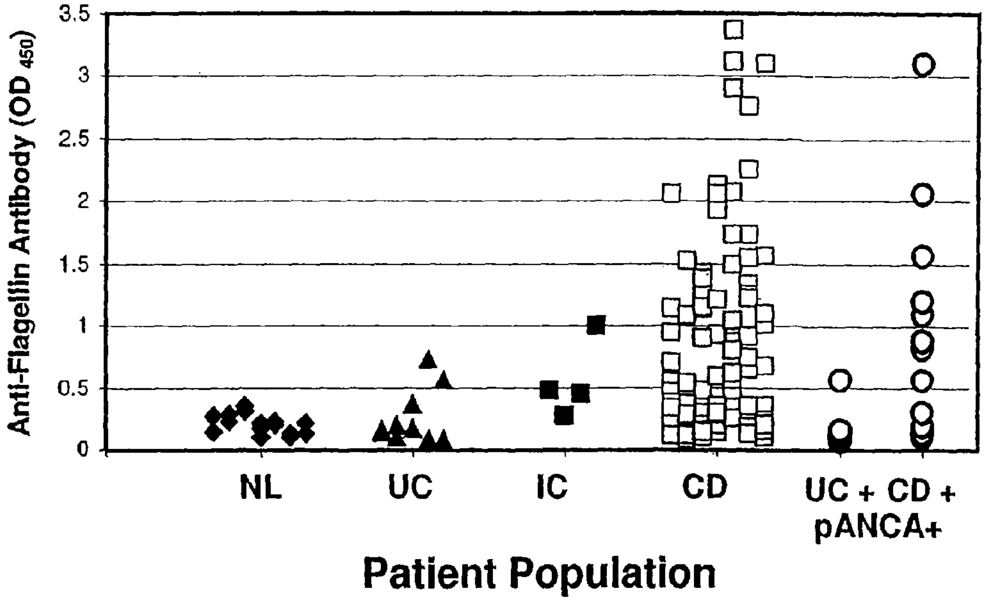
FIG. 2*d* shows association of anti-flagellin antibody with human inflammatory bowel diseases. NL is negative population, UC is ulcerative colitis positive, IC is inflammatory control, CD is Crohn's Disease positive and UC+ and CD+ pANCA+ are ulcerative colitis pANCA positive and Crohn's Disease pANCA positive.

Similar antibody reactivity to recombinant CBir1 and Fla-X were seen in human Crohn's disease patient sera. As above, anti-flagellin antibodies measured using ELISA in a panel of human serum samples from about 150 donors with well characterized human inflammatory bowel diseases, ulcerative colitis and Crohn's Disease, as well as healthy controls patients (Inflammatory Bowel Disease Center, Cedars-Sinai Medical Center, Los Angles, Calif.). A significantly higher level of serum anti-flagellin antibody was seen in Crohn's disease patients than in normal controls, infection controls and ulcerative colitis patients. A significantly higher serum antibody response was seen in pANCA-positive Crohn's disease patients than in pANCA-positive ulcerative colitis patients. These results confirm that the antigens disclosed herein are useful for subdividing IBD patients into categories of disease and would prove useful in clinical diagnosis of IBD, especially Crohn's Disease, FIG. 2*d*.

Example 10

Figure 3A:
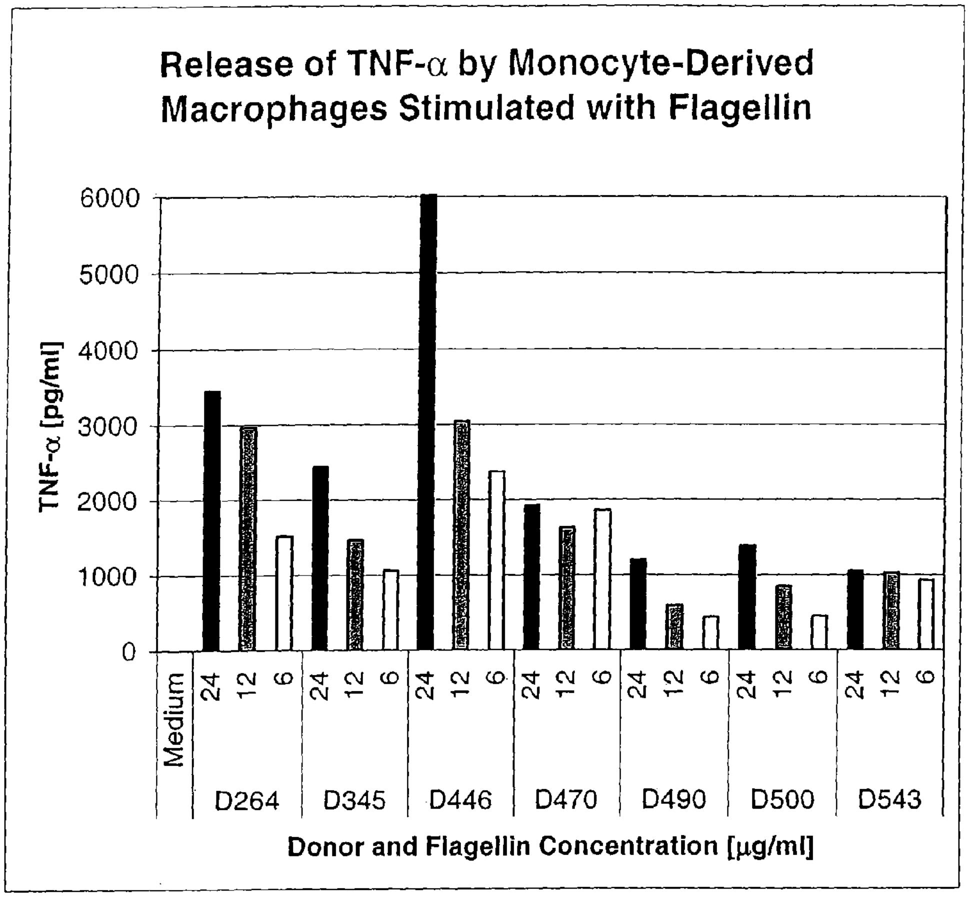
FIGS. 3*a* and *b* show cytokine release by donors stimulated with flagellin.
Figure 3B:
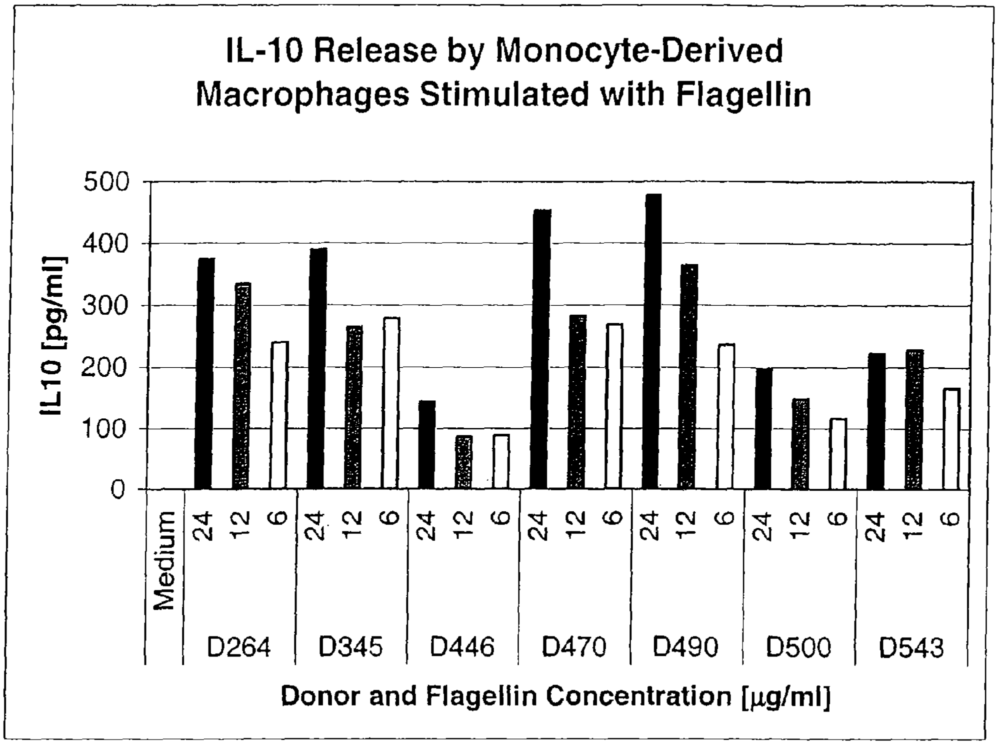

Flagellin-Stimulated Human Monocyte-Derived Macrophages Release Interleukin 10 and Tumor-Necrosis-Factor Human monocyte-derived macrophages from seven healthy donors were cultivated in vitro for five days and then stimulated with full-length Flagellin X (SEQ ID NO:79) at 6, 12 or 24 μg/ml. Release of cytokines IL10 and TNF-α was detected in the culture supernatant by ELISA. Cytokine release following stimulation with Flagellin X was dose-dependent, see FIG. 3.

Example 11

Flagellin Proteins in Combination with Cholera Toxin Adjuvant as a Vaccine for IBD Bacterial flagellin protein, FlaX, was used in conjuction with a known adjuvant, cholera toxin (CT) to prevent the on-set of severe colitis in mice that are genetically prone to the disease. MDR1a mutant mice (MDR1aKO mice) develop severe, chronic inflammation in the colon as they advance in age. 5-6 week old MDR1a knock out female mice from Taconic Farms were either left untreated or given 8 μg FlaX or 8 μg Mtb+10 μg cholera toxin (List Biologics) in a 200 μl volume of PBS by oral gavage. Mice were thus treated on day 1 and day 14 of the experiment. Mice were sacrificed 4 weeks after the last dose, and their large intestines (cecum/colon/rectum) were fixed in 10% neutral-buffered formalin (Sigma), sectioned onto slides, and stained with hematoxylin and eosin (H&E). The sections were examined in a blinded fashion and scored for disease severity.

Scores ranged from 0 (for no changes seen anywhere) to 64 (most severe inflammation and epithelial changes seen through the entire large intestine) arbitrary units. Typically, mild disease scores as 1-15, moderate disease as 16-35, and severe disease as >35. The mean score for untreated mice (n=4) was 23.50 with a standard deviation of 17.37. The mean score for mice given control protein plus CT (n=5) was 25.40 with a standard deviation of 18.43. The mean score for mice given FlaX plus CT (n=5) was 6.80 with a standard deviation off 4.38. The mean scores of the mice treated with control protein vs treated with FlaX were significantly different (Mann-Whitney nonparametric test, p=0.0159). Thus treatment of MDR1aKO mice with FlaX plus CT resulted in less severe disease.

Example 12

Identification of the Full-Length Nucleotide and Protein Sequence of CBIR-11 Flagellin The full length cDNA sequence of Clone ID 76963, Cbir-11 flagellin clone (SEQ ID NO:9) was identified. The nucleotide sequence of SEQ ID NO:87 is the determined cDNA sequence for clone CBir-11. SEQ ID NO:88 provides a predicted translated flagellin-like sequence protein sequence encoded by SEQ ID NO:87. A second predicted translated sequence encoded by SEQ ID NO:87 is provided in SEQ ID NO:89, which is a phosphoesterase-like protein sequence.

Example 13

Creation of Cbir-11 Flagellin Responsive $Cd4^+$ T Cells $CD4^+$ T cells were isolated from mesenteric lymph node cells (MLN) from colitic $mdr1a^{-/-}$, C3H/HeJBir, C3H/HeJ.$IL\text{-}10^{-/-}$ by BD™ IMAG anti-mouse CD4 beads according to manufacturer's instructions (BD Biosciences Pharmingen, San Deigo, Calif.). Briefly, MLN cells were labeled with anti-CD4 beads ands then placed within the magnetic field of the BD Imagnet. The unlabeled cells in suspension were removed and the cells binding the beads were washed and used in the CD4+ T cell culture. More than 99% of the cells were CD4+ by FACS analysis.

T cell reactivity to Cbir1 was determined by stimulation assay as follows, $1.1\times10^5$ T cells were incubated in duplicate in the presence of $4\times10^5$ antigen-pulsed and irradiated APCs (prepared according to Cong et al., *J. Exp. Med.* 187:855-64, 1998). APCs were treated with 1 to 100 μg/ml CBir1 for 18 hours. On day 3 of culture, 0.5 μCi [$^3$H]-thymidine was added and the cells harvested 16 hours post post. T cells responded to Cbir1. Non-specific activation via TLR5 or TLR4 activation was excluded by the lack of stimulation by Cbir1 or Fla-X on ovalbumin-specific proliferation of $CD4^+$ T cells from DO11.10 ovalbumin-specific TCR transgenic animals.

A $CD4^+$ T cell line reactive to CBir1 was generated by biolating $CD4^+$ T cells from MLN cells from C3H/HeJBir mice as described above followed by culture with splenic antigen presenting cells (APC) that were pulsed with CBir1 (100 mg/ml) overnight. The cells were restimulated every 10-14 days. The T cell line was responsive to CBir1 but not to Fla-X or a variety of other microbial, food and epithelial antigens.

To determine if this T cell line could induce mucosal inflammation, it was adoptively transferred into C3H/HeJ-scid/scid recipients and quantitative histopathologic scoring performed 8 weeks post-transfer showed that this CBir1-specific $CD4^+$ T cell like induced colitis in all recipients of an intensity that was similar to or greater than that induced by CBA-specific $CD4^+$ T cell lines, where as none of the recipients given these anti-CD3-activated C3H/HeJBir $CD4^+$ T cells developed disease.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed:

1. An isolated antibody, or antigen-binding fragment thereof, that specifically binds to a polypeptide comprising the sequence of SEQ ID NO:86.

2. The antibody according to claim 1 wherein said antibody is a monoclonal antibody.

3. The antibody according to claim 1 wherein said antibody is a humanized antibody.

4. The antibody according to claim 1 wherein said antibody is a neutralizing antibody against a flagellin protein.

5. The antibody according to claim 1 further comprising a label.

6. The antibody according to claim 1 further comprising a therapeutic agent coupled to the antibody.

7. The antibody according to claim 6, wherein the therapeutic agent is a radionuclide, differentiation inducer, drug, or toxin.

8. A composition comprising the antibody according to claim 1 and a pharmaceutically acceptable carrier.

9. The composition according to claim 8, further comprising an immunostimulant.

10. The composition according to claim 9, wherein the immunostimulant is an adjuvant selected from the group consisting of Freund's Incomplete Adjuvant, Freund's Complete Adjuvant, Merck Adjuvant 65, AS-1, AS-2, aluminum hydroxide gel, aluminum phosphate, a salt of calcium, iron or zinc, an insoluble suspension of acylated tyrosine acylated sugars, or anionically derivatized polysaccharides, polyphosphazenes, biodegradable microspheres, monophosphoryl lipid A, QS21, aminoalkyl glucosaminide 4-phosphates, and quil A.

11. A kit comprising the antibody according to claim 1 and a detection reagent, wherein the detection reagent comprises a reporter group.

12. The kit according to claim 11, wherein the detection agent comprises an anti-immunoglobulin, protein G, protein A, or a lectin.

13. The kit according to claim 11, wherein the reporter group is selected from the group consisting of radioactive groups, fluorescent groups, luminescent groups, enzymes, biotin, and dyes.

* * * * *

SEQUENCE LISTING

```
<160> NUMBER OF SEQ ID NOS: 90

<210> SEQ ID NO 1
<211> LENGTH: 1268
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 76779 Cbir-1

<400> SEQUENCE: 1

ggaggtatta ttatggtagt acagcacaat ttacatgcaa tgaactctaa cagaatgtta     60

ggcatcacac agaagacagc atctaagtct acagaaaagt tatcttcagg ttacgcaatc    120

aaccgcgcag cagacaacgc agcaggtctt gctatttctg agaagatgag aaagcagatc    180

agaggactta cacaggcttc tacaaatgct gaggacggca tcagctctgt acagacagca    240

gaaggcgctt tgacagaagt gcatgatatg cttcagagaa tgaacgagct ggcaattcag    300

gcagcaaacg gcacaaactc agaagatgac cgctcataca ttcaggacga aattgaccag    360

ctgacacagg aaatcgatcg tgttgctgag acaacaaagt tcaatgagac atatctcttg    420

aagggtgaca caaagaacgt tgacgctatg gactatacat atagctataa ggcagttaca    480

acgaatactg tagcaagagc ttcggtttta gcagcagaga acacagctac aggtatgtca    540

gttagtattt catttgctgc aaacagcggc aaggttactg cagctgactc taacaacctt    600

gcaaaggcta tcagagatca gggcttcaca atcacaacat ctacccagaa tggtaaggtt    660

gtttacggtc ttgagctgaa cggaagcgat gcaaaggcaa actatacagt ttcaacagta    720

agtatggaag ctggtacatt caagatcctg aattctaata agcaggttgt tgcatctgta    780

acaatatcta caacagctag ctttaaaaag gtatctggta tgtcacagat cgttacggcg    840

tactctgtat cagcagctta tgcgacgggt gatgtatact ctctctatga cgcagacgga    900

aatgcaattt cagcaaacaa gctggataag tactttacgg caggcggcgc tacagaggca    960

ggcggaatag ctactacact ttcagcaaac tctggtgtgc ctaaggttta tgacgtactc   1020

ggaaaagagg tttctgcagt aagcattgca agtactttag taacagcagt taaggataag   1080

acggctgcat tgaagatgaa cttccatgta ggtgctgacg gaacagataa caacaagatt   1140

aagatcaaca ttgaggctat gacagctaag agtcttggag ttaacggtct gaaggtgagc   1200
```

ggttcgagcg gaacaaatgc tacaaatgct atcgagataa tcgctggcgc tatcaagaag 1260
gtttctac 1268

<210> SEQ ID NO 2
<211> LENGTH: 336
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 76780 Cbir-2

<400> SEQUENCE: 2
gcgcaggaaa aaagttacca gcgtggacaa ggcaaatgtg ctggattcct caaggctttg 60
gcggaaagtt gtagaagaag tcggcaaaag agtacccgga cgtggcattg gagcatatgc 120
tggtagataa ctgtgccatg cagctagtaa aagacccaag gcagtttgac gtgatcctga 180
cagaaaatat gtttggcgat attttgtccg atgaagcaag catggtgaca ggctccattg 240
ggatgctttc ctccgccagc ttaaacgata ccaaatttgg gctgtatgaa ccaagcggcg 300
gttctgcgcc ggatattgcc gggaaaggga ttgcca 336

<210> SEQ ID NO 3
<211> LENGTH: 658
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 76959 Cbir-3

<400> SEQUENCE: 3
ggcccccgcc ttcggcatgg tgggcaccct ggtgggcctg atcaacatgc tgaaggccat 60
ggacatcgag accgttggcg gcaacctggg ccccgctatg gccaccgctc tggtcaccac 120
cctctatggt tgcgtgctgg cccacatgat cttcggcccc atcgccaccc agctgcgcca 180
gcgggacgag gaagagaccc tctgcaagct gatcatcgtg gaggggctca tgtccatcca 240
ggccggcgcc aaccccaagt tcctccggga gaagctgctc accttcgtca cccagaaaca 300
gcgtggcgag aacggcggca agaagggcaa gtaagagctg cggggccgcg tccccaccgc 360
tctgcggtat gaactgaggt gaaacaccat ggcaagcatc aagaaaaaga gctccggcgg 420
cggcggcgcc aactggatgg acacatacgg cgacatggtc accctgctgc tgtgtttctt 480
cgtcctgcct gtattccatg tccacgatcg actcggagaa gtggaagatg atcggtccag 540
agcttcaata agaacgcagt cgtcagcgac gatcagcccc ccggaccgga cggcactgaa 600
agcagcacgg gcggcatgaa tctgcctttg acccaggaca tgcaggccgc catggatc 658

<210> SEQ ID NO 4
<211> LENGTH: 644
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 76960 Cbir-4

<400> SEQUENCE: 4
cttgggaagt atttaaaagc gcaggcattg ctggaaaagc tgcgctatta tgcggagaaa 60
tgcgggcgca cctatatccg catggaagtg tgcctcctta gcgccgtagc gaaataccga 120
acaggcgggg aatggaaggg ggaatttttc ccgatgctga gagaagcctg cggatatcat 180

```
tttatccgcc ttgtcagcga ggaaggggcg gcggcgcagg aactgtttgc ggcggcggga    240

aagagtcttc tggaaaagga agtaatggat aaggcatggc tgtccaggct catggaggaa    300

acagggaagg tggcggtgcg ctacctggcg tatttaaaag gccggcttgc cgaagcgccg    360

gatttctgtg aggcggcatt atccatcctg cgcctgcagg cggaaggaaa gagcgcatca    420

atgaagcttg gagttttttt tgttcggcta ttttttggcg tcggtaagct ttacgttttt    480

gaaagtcagc acagagaaag gagaggtagg cagcggagta taagacatgc ggaagcaaat    540

gaaccaaatg gaggtagaaa catgacgtta tttcaatgaa cagttgttgg aagcaggtgt    600

tctttcggac atcagacaag aagatggaac cctaagatgg ctcc                     644
```

```
<210> SEQ ID NO 5
<211> LENGTH: 685
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 76961 Cbir-5

<400> SEQUENCE: 5

aatgaaactt atcaaaaaca atctctccat cacacaaatg cttgttgaaa catcatctca     60

tcttgatagc aacactaaaa atattgccaa aatttcacag gataacaccg agctaggcga    120

aaggagtgtg aatatcattg agcaaaacat cacccttca aatgcaacaa aagaatcttt    180

agaagatgtg cttaatacga tgcagcaaac tcaagcactc ataagctcta tcaacgaaga    240

aatcacaaaa gacgcacaaa aagaagatga aaatatgcaa aagattctct ctcttgctaa    300

tgaggcaaaa aatattcaaa gtgtacttgt aactattacc gacatagcag accaaacaaa    360

cctcttagca cttaatgcag ctattgaagc agcgagagct ggggagcacg gacgaggctt    420

tgctgtggtg gctgatgaag tgagaaaact agcggagcgc acacagcatt ccattacccg    480

agacaggtag cattatccaa tctgtcttgc agtctattga tgaagtatca agtgatatgg    540

gaaaccagtg ccaaatcaat gaataatctt tcaagcaggg tgaagtgatg ttggcaatat    600

acaatctctt gcccactcgt gcaagaaacc aatgcaaaat cattgcaaag gctagaggga    660

gccccaatgg cgaatgaaaa tacca                                          685
```

```
<210> SEQ ID NO 6
<211> LENGTH: 929
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 76781 Cbir-6

<400> SEQUENCE: 6

atcatttcta cgaaccaggg tgtcatcaca gacaaagaag caagaaagct cggcgtaggc     60

ggagaagtac tggcatttgt gtggtaggca ctggcactga acacttagcg aagccaagcg    120

ttccgcgcag gctgaggtta gtgtgaaggc cgttctcaga gcgaagcgaa gagaacttcc    180

ttgctaggga acacttagcg aagccaagcg ttccgcgtag gctgaggtta gtgtgaaggc    240

cgttctcaga gcgaagcgaa gagaacttcc ttgctaggga acacttagcg aagccaagcg    300

ttccgcgcag gctgaggttg gtgtgaaggc cgttctcaga gcgaagcgaa gagaacttcc    360

ttagaggaaa caccatcgtc actagactcg aaagaaactc gccaagtgat cacagcaact    420
```

```
gaaaacagag caggcgaaag gttctgctcc gagaatttaa gttaaggagg atatggcaat    480

gtcacgtatc ggaagactgc caatcgcgat tccggcagga gtaactgtgg aaatcgcaga    540

gaataatgta gtgaccgtaa aaggtccaaa gggaactctg tctcgggagc ttcctgttga    600

aatggaaatt aagaaagacg gcgagacaat cgtcgttaca agaccgaatg atttgaagaa    660

gatgaaatcc cttcacggcc ttaccagaac actgattaac aacatggtta tcggcgttac    720

agaaggatat aagaaagttc ttgaagtaaa cggtgttggt tatagagcag caaaatcagg    780

aaacaaatta acacttagcc ttggatattc ccatccggta gagatgatcg acccggaagg    840

cgttgagacg gttctcgagg gacagaacaa gattaccgtt cagggtatcg acaaggaaaa    900

ggttggacag tatgcagccg agatcagag                                      929


<210> SEQ ID NO 7
<211> LENGTH: 652
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 76962 Cbir-8

<400> SEQUENCE: 7

gcatcaaaag catcgctaat tgccgctcct gctggaacca tagggaaaac tttatcatct     60

tcttcaatca cgcattcaat tactactggt ttctttaatg caatggcttt ctcaatcgca    120

ggcgcaacct cctcacgctt ggtaacccgg attgcctcac agcctaaacc ctctgaaacc    180

tttacaaaat cgaccttatc cgtaagaatg gtctgtgaat accgtttacc ataaaataaa    240

gtctgccact ggcgcaccat acccaaaaca tgattattta tcacaatctg gataattgga    300

atattatagc ggcttgcagt tgccaactca ttcaaattca tccgaaaaca cccgtcacct    360

gcaatattca cacatatttt atctggtctt ccaacctttg caccgataca tgctccaaga    420

ccatatccca ttgtaccaag acctcccgaa gttaagaaag tacggggttc tgtataccta    480

taaaactgtg ctgcccacat ttgatgctgg cctacccgct caatttttgg ttgcctatgt    540

agctcagggt agaagcactt cttggtaagg gaagaagtcg cggggttcaa aatcccgcca    600

tcggctttta agtaaaaaac ccccgggagg ggcttatttg cattaatccc cg            652


<210> SEQ ID NO 8
<211> LENGTH: 497
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 76782 Cbir-9

<400> SEQUENCE: 8

cttcgctcgg atggcttcat cctcgaccgc gtcacaaatg ggccctggtg gtctactact     60

gctggttctg ctacggacgg tcacctcttg aatacgtacc cgacgaatat ctcccctcag    120

gataaccgtt cccgcgggtt cggttttgcc gttcgctgtg tggtacggga ggggtggagg    180

ctaaatctgc ttcctacgcg tcgctgggcg tttgcgtggc ggtacggcat ttttcttagc    240

agccccgcgc gtagccggac tagacactcc cgttgcgggt ttccctgcgc ccccccgtgt    300

tgttcgagcg gtttttgtag ctcctcttgc tgccgctcta ctattgcttc tcgtagccgt    360

acttctagtt gtttttctac ttgatgccct agcgctttcg gcgatttgct tctcgattcg    420

tgcagtaatg ctagcgagcg cctcggtgtc acccattgcc tcataaatcg ccaaaatttg    480
```

```
ccgcaaagta tttgtac                                                497

<210> SEQ ID NO 9
<211> LENGTH: 327
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 76963 Cbir-11

<400> SEQUENCE: 9

gtgtgtggtc cacggcgcgg ccttcaccgg cggtgagcgc acggaccagg tgctggcgga     60

cttcaccgcc ccggaggacg gtcttctcca catcctctgc ctccacggcg acgtcttcag    120

ccaggacagc gtctacggcc ccatcacccg gccccagatc gcccgcagcg gcgcggatta    180

cctggccctg ggccacgtcc accagtgcag cggcatccag cgccaggggg acaccccctg    240

ggcctacccc ggctgtcccg agggccgggg gttcgacgag ctgggggaca agggtgtgct    300

ggcggggacg gtggatcggg gcggggc                                     327

<210> SEQ ID NO 10
<211> LENGTH: 621
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 76964 Cbir-12

<400> SEQUENCE: 10

attgagatac cattggccga gtgattgcgg cttataggga taaacaaaaa cgtgtctgag     60

atgttactta taaagtgctg ttgtgcctgc aggtgtcatt tctcgaacct ttattgttaa    120

atataataaa taaggaaaaa tttctttaat aatacgtcat ataccgcaaa attttagtaa    180

ctttgcactc gggaaaaaac gtgtttttta gaaatcaaaa tttatcaact cccaataaat    240

aacaaggtca tttactacaa tgagcacaat tgaagaaatc aagaaagccc gtgtagccga    300

catcaagaag aatcttgaaa gctacggcat cgacggcaca actgaaatcg tgtacaaccc    360

tacctatgag cagctctttg ctgaagagac actccccttg ctcgaaggat atgaaaaggg    420

tgttgccact gagcttgacg ctgtcaatgt tatgaccggc gtatataccg gccgttcacc    480

caaggacaaa ttcatcgtac tcgacgaaaa ctcaaaggac accgtatggt gggacaaccg    540

aagaatacaa gaacgacaac aagcccgctt ccgaaagagg catggaaggc ttgcaaggaa    600

cttgcagtga aaggaacctc a                                           621

<210> SEQ ID NO 11
<211> LENGTH: 625
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 77529 Cbir-13

<400> SEQUENCE: 11

acggtacggg caagcgggat cgcgacttta ggatctgcaa gtcccaaagc ctttgccgct     60

ttcagcgcgt cctttcctac agactgtgcg gctgtagcag gacggctacg catcatctca    120

atttcgttat gaatctgagc gcgctgctcg ccggcgcgta cggtcagttg ggcaagtctg    180
```

```
cgcgcgactt cgtcatttgc ctgcattatc ggcctccttt gtctgaaccg aaggaaatag    240

agcagataaa aaaagaaatg agggaagcgg gcattaaata aaagaatgtg accgattcgg    300

acaccgaaaa aacaagaaag agaggattta aaaatggcag gatttgacct taatagtttg    360

ctgaatggaa agagcaaagg ggcagcagga cagaagcagg aaacggcggt agcagggcag    420

gggccggcag aggggcagga aagcagtttt gaggttgtaa tgcttgatgt agaggactta    480

atgccaagca aggataattt ctacacaacc gagggaataa acgagttggc ggacgctatc    540

gagttgtcgg gcggtatcga gcagaattta attgtaaagc cgggaagcac acggaaagta    600

tgaggttatc gcaggacacc gcgga                                          625
```

<210> SEQ ID NO 12
<211> LENGTH: 542
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 76965 Cbir-14

<400> SEQUENCE: 12

```
gatcgctgcc tgtttgactc ctgatattgg tcttcaacgt gagcttctct ttgtgcctgc     60

acgaggagga ctaggtgaac ggatggagat ccaggcaaat aacgtgtgtg ctcggatggc    120

tcgacggact ggtgggaaaa gccgttcgct ctatgtgccc gagcaagtaa gcgagagtac    180

gtatcgtcca ttgttaaaag aacctgctgt tcaagaggtc gtcaatttga tcggtcaaag    240

taatgctgtg atccacagca tcggaacagc aatgcatatg gcacatcgac gttcgatggc    300

gccagaagtg atcgcaatgc taaataagaa aaaagcggtc ggtgaagcat ttggttactt    360

ttttgatgaa aaagggcaga tcgtgtatcg gatctcacgt atcgggatcc agttagaaga    420

cctccttcta tggaatgtgt aattgcccgt cgctggtggc acttcaaaag ctaaagcgat    480

ccgtctctta catgaaacac ccttctaaac aaacattgtc tgatcacaga ccaaaggaac    540

ca                                                                   542
```

<210> SEQ ID NO 13
<211> LENGTH: 585
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 76966 Cbir-15

<400> SEQUENCE: 13

```
gggctgcgga ttattaaacc ggggagatat aagagtggat gccgaaaaat ggaatcttta     60

atttccggtc atagatgaaa aaaattgaat atagaaatag aagatgttaa gggtgacgaa    120

aggattcgtc gagaactatg acactgtcat agtcagccaa cacaaggagg taattttatg    180

gtagtacagc acaatcttac agcaatgaac tcaaacagaa tgttaggaat cacaacagga    240

agtttagcaa aatcagcaga aaaactgtct tcaggatata aggtaaaccg cgcagcagat    300

gatgcagcag gacttgcaat ttcagaaaag atgagaaagc agattagagg tcttacacag    360

gcttcaacca acgcagaaga tggtattagc gcagtacaga cggctgaggg tgcattgact    420

gaagttcatg atatgttaca acgtatgaat gagttggcag taaaagctgc aaacggtcaa    480

tgtctctttc tgacagacag accattccaa gatgaagtga cacagcttct cacagaagtt    540

gcccgtgtag cagaaacttc caaatttcac cgaaatttat tcttg                    585
```

<210> SEQ ID NO 14
<211> LENGTH: 916
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 76967 Cbir-16

<400> SEQUENCE: 14

```
gtagaagatg gaacgtttaa gaccattcac atcacattaa aatatggtgc agataagaac     60

gaaaaagtaa tttccggcct taagagaatc tccaaaccgg gtctccgcgt atacgcaaac    120

agcgaagaga tgccgaaggt actgggcgga ctcggaattg caatcgtatc tacaaataaa    180

ggtgttgtta ccgacaaaga agcaagaaag ctcggcgtag gcggagaagt tctttgcttt    240

gtgtggtgac cggaagcact tggtgaatcc aagcgtaagc gagagatgaa cttagtgcga    300

ggtcgttctt tgagcttagc gatgcattga atacttggcg aggtattatc gagcctagta    360

tgaaagcaga tattccgaac gaagagagga atatcttcga cagagcttag cgaaaagaac    420

agataaactg aaaacagagc agactcaagc ctctgctccg aaaatttaag ttaggaggac    480

aaaggtatgt cacgtatagg aagactgccg atcgcagtcc ctgcaggtgt aactgtagag    540

attgctgagc ataatgtagt gaccgtaaaa ggtccgaagg gaactctcgt aagagaactc    600

ccggttgaaa tggaaatcaa gcaggaaggc gaagaaattg ttgtcaccag gccaaacgac    660

ttaaagagga tgaaatccct tcacggcctg acacgtacac tgatcaacaa catggtaatc    720

ggtgtcagcc agggttatga aaaggttctg gaagtaaacg gtgttggtta cagagcagcg    780

aagtccggca acaagctgac cctcagcctt ggatattcac atcctgttga gatggttgat    840

ccggaaggga tcgagacagt tctggaaggc cagaacaaga tcacggtaaa agggatcgac    900

aaagaaaaag ttggcc                                                    916
```

<210> SEQ ID NO 15
<211> LENGTH: 625
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 76968 Cbir-18

<400> SEQUENCE: 15

```
aatgaatgca aacagaaact tggggatgac cacaaccgca caggcaaaat ctacggagaa     60

gctttcttct ggttaccgga tcaaccgcgc ggcggacgat gcggcgggcc tttcgatttc    120

cgagaagatg cgcagccaga tccgcggcct gaagcaggct tccaccaatg cgcaggacgg    180

catttccctg attcagactg cagagggtgc gttaaatgag cagcattcga ttttacagag    240

aatgcgcgag ctgtccgttc aggcggcaaa cggtgtggag acggacgacg accgtgaggc    300

agtcaacaac gagatcagcc agctccagtc cgagctgaca aggatttccg agacgaccga    360

gttcaacacg atgaagctgc tcgacggaag cctttccggg acagccggat cgtccaccgg    420

ctcaggcccg aagttcggcg tggtagatgc aaccttagac ggcgcgcttg tgacgtcgaa    480

tgttgcaggt gtcaaggtag ctacagcttg ctacgacaag tacaaaagcc ggacagggag    540

actgccatct gggacgcaac ccggaaagac cttgacattg aatctttctc gtgcccgaat    600

tcaaaaaagc tttttcgaag aagta                                          625
```

<210> SEQ ID NO 16
<211> LENGTH: 603
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 77530 Cbir-19

<400> SEQUENCE: 16
aggccatctg aaaatcggac acaatgtgaa aatcggatat ttcgcccaga atcaggctca 60
gcttctcgac ggcgaactta ccgtttttga caccatcgac agggtggctg tcggagatgt 120
ccgcacaaaa atacgcgaca tcctcggcgc attcatgttt ggcggagagg cgtcggacaa 180
aaaggtgaag gtgctctcgg ggggcgaaaa gactcgcctt gcgatgataa aacttctgct 240
tgagccggtg aacctgctta ttttggacga accgaccaac cacctcgaca tgaagacaaa 300
ggatatactc aagcaagcga taaaggactt caacggcacg gtgatagttg taagccacga 360
ccgcgaattt cttgacggac ttgttgaaaa ggtatatgag ttccggtggt ggggctgtgc 420
gtgaaaacct tggcggaatc tacgatttcc ttgaacgcaa gcgccttgct tcattgacgg 480
agttggagcc gaaatgcacc ccgggccaaa gatgacaaaa ctcctccccg gcgaagcgag 540
aacactcagc ccgcccacgg actcgcaacc tttaagctac cgccgaggcc cgcgaacccc 600
gac 603

<210> SEQ ID NO 17
<211> LENGTH: 548
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 76969 Cbir-20

<400> SEQUENCE: 17
gtctatatga ttattcaaca taatatagcg gcgattaact cttatcgtaa cttaggcgta 60
aaccagagcg gactgaacaa aaacttagag aaactgtcat ctggttacaa aatcaaccgt 120
gcaggcgatg atgcagcagg tctggctatt tccgagagca tgcgttctca gattaacggc 180
ttaaaccagg gcggactgaa caaaaactta gagaaactgt catctggtta caaaatcaac 240
cgtgcaggcg atgatgcagc aggtctggct atttccgaga gcatgcgttc tcagattaac 300
ggcttaaacc aggcagtaaa caacgcaaag gatgccatcg gtttgattca gacggcagaa 360
ggtgctctga ccagggattc ggcgtatccg tttccagcgg tatgctgcag gattccatcg 420
ctgatacgaa acggattgaa tacacaagag ttgaataaat gaatagagca gcgttgacgg 480
gttgtgcccg tcaacgctgc tttgtccata ggcagttcga ttttgccggt acgcattgcc 540
aaataaac 548

<210> SEQ ID NO 18
<211> LENGTH: 535
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 76970 Cbir-23

<400> SEQUENCE: 18
agctacgttg agtaccagac tgcaaatcgt cactatgcac acgttgactg cccgggccac 60
gccgactatg tgaagaacat ggtaactggt gcagctcaga tggacggtgc aatccttgtt 120
tgtgctgcaa ctgacggtcc tatgcctcag acacgtgagc acatcctcct cgcccgtcag 180
gtgaacgttc caagaatcgt tgttttcatg aacaaggttg accttgttga cgatcctgag 240
atgcttgacc tcgtagagat ggagctccgt gacctccttt cattctacaa cttcgacggt 300
gacaatgctc cggtaatccg tggctctgca cttggtgcac tcaatggtga ccctcagtgg 360
gaggataagg ttatggaact catggcagct gttgacgagt atattccgct tcctccacgt 420
gacaacgaga agccattcct tatgccaatc gaggacatct tctctatcac agggcgtggt 480
actgtagcaa ctggacgtat cgagacccgg gatcattcac cgtaggtgat gaagg 535

<210> SEQ ID NO 19
<211> LENGTH: 505
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 76971 Cbir-24

<400> SEQUENCE: 19
aggaaatcca atggtgccgg gactgggtat ctcagtatga gaattacgcc atgtatcgga 60
aatacgggct gggagcggta attctgaaag agggggagcc ggtgtccggc gcgtcctcct 120
ataccggtta tatcggcggc attgagatcg aaattgatac cagagaggac tgccgcagaa 180
agggcctggc ctatatatgc gccgccagac tgattttgga atgtctggac cggggctggt 240
atccaagctg ggacgcgcaa aatctgtggt cggtggcgct ggccgggaag ctgggatatc 300
attttgaccg ggaatatacg gcatatatgc gggtcaggta ggggaaaggg aacgtaaaat 360
caagtaccgc gagatttgag agaacataaa aaataacagg aggttccgat agatgaaagt 420
tttaatgctt gaacggcagc cccgtgcca acgggaatac atacgcgctt ctgccggtga 480
aaatggaaaa aaatttttga acagc 505

<210> SEQ ID NO 20
<211> LENGTH: 532
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 77073 Cbir-26

<400> SEQUENCE: 20
gtaaggtaat tctgttaaaa ttgactgggg cgtgtttgga atgtttttttg gcagatacca 60 aacgcgccct aagcaagaca ggggaatgga atatgagcgt acaggataaa atagaacatg 120
tattaaaatg catacacctg ctgttttcca aaagccagcc ttacggggac agcaatacaa 180
agattattgt ggataaaaaa gccgtttttg aactgctgga acagttaaac cttgcagttt 240
atgaggctat ggaccattat gaggttacca cccgtaagca tgagattgca gagcggcgct 300
gcgagaaacg gggcgaggaa atcatccaga aggccagcaa gcacgcggac gacatctatg 360
ccgcttccat tatgtatacc gacgatgcca tcaaccggat ttgctatatt atggatgacg 420
cccatcaggc tgtccaaaat attttccgta agatgaacgt agagatggaa aaacccctcg 480
tgccgaattc ggccgaagga gtggggttgg taatcgacgc aaagccgacc ca 532

<210> SEQ ID NO 21

```
<211> LENGTH: 467
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 76972 Cbir-27

<400> SEQUENCE: 21

cttacacaag agcctgccga aatcttaaat cacacctact aatatacaat gcgtgaggat     60

attgtgatgg caatggagga actggagctt acgccgcagc aggcaaaggc actcttgaaa    120

tctccctgtc cgcttgatga tgtgtataag gaatttaagg acagagaggt cgagcatatg    180

gatacgattc gtgattccat tgaaacgaga gcagatcagg ttatcaagcg ggaaaacgca    240

agggaaagca ggtgatccta tgccgtatat cccaccggag gtgattgaac aggcaaggca    300

aattgatttg ctctcatata tgaaagcctt tgagccgaat gagctggtca ggatttccgg    360

caacaactac accacccgca ctcacgacag cttaaagatt tcaaacggta aatggatgtg    420

gtggtcgcag cgaatcggcg ggtataacgc ccttgattat ctcataa                  467


<210> SEQ ID NO 22
<211> LENGTH: 701
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 76973 Cbir-30

<400> SEQUENCE: 22

cttttggcac tttttttgat gcaacataaa atttttatcc aggagaatgc ttaatgaaaa     60

accaaaaaca aaccataaaa tgctcagaat gtaaccattg cagcggcttg cgtcgtcccg    120

gcaacacaag cacgagcttc acctgctccc accctgacca ggggtatatc caggactatt    180

tccgtgaaaa aaggatgaac aagatgcctg gtttccttgg atacggggca agatattcgg    240

aggccgtccc tatcaagaca gctcccgcct ggtgccctga aaaaagggcg gcaaaacaaa    300

aacgaaacgg gcaatgaccg ctttagaaac aaccggggag aggcagttta tgctgtttct    360

cctctttttc attccactct atctgcataa aaaactcaca tacagaatat gaaattgaat    420

tttgcacata attctgttat aataatacac aaataggcga ttgcgaaaca agttcgcaat    480

attaattcca acagggaaaa attcggtcat gtcggatttt aaggaggtgg atatgagtaa    540

tcggatttta agacatgaaa ataaagcaga tagggacatc tgcctgcgaa atggcatggt    600

ggtatgtgaa ggtatgcaat cagagggttt agactgcgga tatatttgat gcttgggcag    660

tttggtcagc cgcttattac cagtgataag ctgggtaatc c                        701


<210> SEQ ID NO 23
<211> LENGTH: 68
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 76974 Cbir-32

<400> SEQUENCE: 23

catgggggtt ttccaacacg ccgttttcca ccatgtcctt ggcgcccagc aacttttcct     60

cggcgggc                                                              68
```

```
<210> SEQ ID NO 24
<211> LENGTH: 572
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 77074 Cbir-36

<400> SEQUENCE: 24

tgattatcga atataatcat aaatagctga ttttagtttt tatcaataag acagcccata     60

tgggcagaaa attaaggagg acgttttaaa atggctaaag ctaaatttga gagaaacaaa    120

ccacattgca atattggaac cattggtcac gttgaccatg gtaaaacaac tttaacagca    180

gctatcacaa aagttttatc tgagagggtt gcaggaaacg aagctactga ctttgaaaac    240

attgacaagg ctccagagga aagggaaagg ggtatcacaa tctctaccgc acacgttgag    300

tacgagacag acaacaggca ttatgcacac gttgactgcc caggccatgc tgactatgta    360

aagaacatga tcactggcgc tgcacagatg gacggcgcta tccttggtag tgggctgcta    420

cagaccgggc ggttatgggc ttcaagacaa aaaagaacct tattcccttt cttgtccccg    480

tccagggtaa ggggccggtt tccctttaat tattccggtt ggaattttcc attggaaacc    540

caaaatggtg gaaccattgg gggtttggga cc                                  572


<210> SEQ ID NO 25
<211> LENGTH: 442
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 77531 Cbir-37

<400> SEQUENCE: 25

cttttatcac gacttccatg ggcgaacgtg gtgacgtcac cgtggaggaa gtacggtccc     60

tcctggagaa ccacttctcc ggtggactgt cgcgcactgt caccgttgag gacatccagc    120

gggcggtgga ggaatattac aaggtaagcc atagcgatct cgtcggcccg gctcgcagcc    180

gcaccatcgt gcatccccgt catatcgccg tgtacctctg ccgtcagatg cttgatatgc    240

cccagggcga tatcgggaag aagttcaacc gggaccactc gaccgttatc cactccactc    300

gaaccgttga ggcgatgctc gaggacaaca tggaggttca gagcgacgtg gagaggctca    360

tgaagatcat tcgggaatcc taagtgaaaa actgggggat tgtagggttt atcattataa    420

ttatggcggg taccgtttat gg                                             442


<210> SEQ ID NO 26
<211> LENGTH: 566
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 76975 Cbir-39

<400> SEQUENCE: 26

gagataatac caagaaacgg cagggaaacg gaaaacaggg gagctatatg agaatacagc     60

ataatatctc ggcaattaat tcccaaagaa atattatgac aacggatcga gcattatcta    120

agaatctgga gaagctaagt tccggataca ggattaaccg cgcgggggac gacgcggcgg    180

gccttgccat atcggaggct atgcggaacc agattaccgc gatgaatcag gggcatgagg    240
```

```
aatgtgcagg acggaatttc cctggtgcag acggtagaag gcgccctgac agaagtccat    300

accatgctca accgcatgaa gggcatggcg gtgcaggccg ccaacgggac atacacggaa    360

tcagaacggg ccatgttaaa ctcagagatg gaagagctaa aggcagagat tacacgtatt    420

ggtgaatcca caacgttcag cggggtaccg ctctttacga acggtgggat taagaggaac    480

gtcacgctga cctcctatta cggctgcacg ctggatctat ccagaggcga agtccacgtt    540

aattattccg gcagtgtggg cagagc                                         566
```

<210> SEQ ID NO 27
<211> LENGTH: 577
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 77075 Cbir-40

<400> SEQUENCE: 27

```
tattcaaaat gtgcagagaa gggaagatga aaaatgaaga taaacacaaa tattgcagcg     60

atcaaagcga gtggacactt gaaccggaca gaggataaga tcactacaag cctggagaga    120

ctttcttccg gataccggat aaataaggcg gcagatgatg cggcgggaat ggcgatttcc    180

cagaaaatgc atgcgcagat tcgcggatta cagcgtgctt ccagaaatgg tgcggatggt    240

atttccttta tccagaccgc agagggcgcc cttatcgaag tagaaaatat gctgcagaga    300

tgccgtgagc tttctgtgca ggcggctaac cagggtgtga ccatgttgga agataaagag    360

gcgatccaga aagagatcga ttctctgatg gaagagattg accgtctttc aactgatacg    420

gaatttaaca cgaaaagtat tctggatggt tcctgctgtc gtcagacatc ttctaataat    480

attggagtga aggttgtttc catgacagac tcggtgggaa atgacaaaat attggaatgg    540

ctttggacca ggtggccacg aagaccattt tttccat                             577
```

<210> SEQ ID NO 28
<211> LENGTH: 361
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 76976 Cbir-41

<400> SEQUENCE: 28

```
ggaggggctg aaggaggtgg cccaggggat cgccgcggcg gagcagcggc ggacggtgta     60

taccgtggcc cagggggaca ccctgtgggg ggtggccggg cggtacggcg tgaccataga    120

ggcgctgctg cgggccaatc cggccatcaa gaaccccaac ctgatccggg tgggacagca    180

ggtggtggtg ccggtatgac agtgcggctc ttgacggtgg acggccggca gtttgagctg    240

ccggtgaccc tccggtggcg tatcctgcgt accggcggcg tgccctgcga cgagatggag    300

gcggtgtgcc tctacgatgg gaagctgggg gcaatcctgc ccctgtgcca ccggttcgcc    360

c                                                                    361
```

<210> SEQ ID NO 29
<211> LENGTH: 596
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 76977 Cbir-44

<400> SEQUENCE: 29
gcagcagaaa gactttcgtc cggttacaga gtcaaccgtg cagcagatga tgcggcagca 60
atggcgattt ctgagaaaaa acgggcacag atacgagggc ttgcccgcgc ttcaaaaaat 120
gcacaggatg ggattagttt tgtacagact ggagatggag ccatgagcca gattggggca 180
atgctccacc gaatgcggga gctcacggtc caggcgttga atgacggggt ctacgaacca 240
gctgaccggg cggcgctgca gatggagttt gatcagctgc agggtgagat tgaccgggtg 300
aacgaccaga cagaatttaa taaaaaacct gtatttgaac attatacaga caatttttca 360
ttgcttgagg gaaaccgggt ttggagccag gatcagatcc ataccatcga tagcagcaat 420
tcctctctca cggtgaaata tattgcggtg gagccagacg ggacagaggt agaaaaagaa 480
aagacactta cgattcctga ggggacatat accacccggg aattgatgga tgaaatggat 540
aatgtggtgt cagcgctggg agatgaggcg gatggactgt atctggaata tagtgg 596

<210> SEQ ID NO 30
<211> LENGTH: 389
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 77532 Cbir-45

<400> SEQUENCE: 30
aaccgaagcc ggtctggaag tctatggcca cactctatgc tggcatgaac agcagaccgt 60
gaagtggctg aactctctaa tcaaggataa ggagcttgag gtggatccta acgagaaggt 120
ggaaaaagag gattatgtta tggattattc tactgtttca tcttacaatt tctgggctcc 180
cgatgaagtt aagccaaaca ttacgataaa tgagggttgc tttgaacttg taaacgcagc 240
tgctactgac aattggaaga tccaatatca tgttgccgac ggacttccga ttgaaaaagg 300
aaaatcgtac aggcttaaag tgatggcccg tggtaccggt gaaggtacga tggaaggtaa 360
agtcggtgat tggggaggcg gatcaaatg 389

<210> SEQ ID NO 31
<211> LENGTH: 592
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 77533 Cbir-46

<400> SEQUENCE: 31
agaaacatgg gtcttcttca tggaagactc gctagaccca cactctcttg tgccactgca 60
tgatgactga ttagaatgag agccatggtt agcagcctcg tgccggaaaa caacacttaa 120 catacettag atttacgcga tcatgaaaac aaaacgactt ttactcggtg acgaggcgtt 180
tgcattaggt gcaatcaatg ccggtctgtc aggcgcatat gcatatcccg gcacaccgtc 240
cactgaaata atggagtatg tgcagacaaa tcctgtggca aaggagcgag gtatacattc 300
ccattggtca tcaaacgaga agacagcaat ggaagaagct ctcggcatgt cattctgcgg 360
taagcgtaca ttcacgtcaa tgaagcatgt gggtctgaat gtagccgccg atcctttcgt 420
caattctgca atgacgggag cgaacggcgg tcttcttgtc gtggcggcag atgatcccgg 480
aatgcattcg tcgcaaaatg agcaggattc gcgtttttat gctgattttg cgatgattcc 540
cgcacttgag ccttcagatc agcaaggagg cttatgatat ggcgcgtgcg gg 592

<210> SEQ ID NO 32
<211> LENGTH: 483
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 77534 Cbir-49
<220> FEATURE:
<221> NAME/KEY: modified_base
<222> LOCATION: (362)
<223> OTHER INFORMATION: n = g, a, c or t

<400> SEQUENCE: 32
ggggcttgcg acgaccacgt cgaagtcgaa ccagttctcc ttctggatct tctccaccca 60
ttctgtattg gtatcattga gagattgaat cgttaattcg gtcatgcggt gaagaatatc 120
atgtgcttca tttaaagcac catctcccgt ctgtacccag gagatgccat cctcgacatt 180
cttgcttccc tggtttagcc ctcgaatcat atagcgcatt ttttcagaaa tggcaagtcc 240
tgcggtatca tcagcagctt tgttgatacg atagccagag gaaagcttct cgacagactt 300
ttgtttctta ttggtgttga tattcagttg atttgccgta tttaaggcag atagattagt 360
gntgacaatt aacatattta gcccctcttt ctaaaataat catgttattg caaatccatc 420
gccaatatta taaatttttg agtttcccca ttttgcacat aaaagcgcga tggggtcgct 480
ccc 483

<210> SEQ ID NO 33
<211> LENGTH: 214
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 77535 Cbir-50

<400> SEQUENCE: 33
gcttcaagaa aattttataa attttttaag aaaaaataga tttgcccaca atgcccacgg 60
agtatgtggt attatggtat tgtcgaaaga caagggaaga gaggtattta gatactcctt 120
ttataagcac tcaaactggc gatagaaaaa gcatctcaaa agggtgcttt ttctgttgta 180
gagaaacagg tgggaaggtg gtgtcgcggc tcat 214

<210> SEQ ID NO 34
<211> LENGTH: 375
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 77076 Cbir-61

<400> SEQUENCE: 34
tatacggaga gcttgtccag gcttttacgg tttgccggaa accgcatgga agcggtgggg 60
ctataccaga tgatacttca ggttttgtgg ctgattctgc tgtttgcagg gatcagcctg 120
ctctttggcc gcgtggcagg aatcgtgacc ggaagtgttc tggcggtttc tttctggatg 180
atggagacca ttcttgtaat ttggcccgga aacttctata tgctgcattt tactatagcg 240
cttatgttct taggatacgt cagataccgg atcaaaaaag ggggatggcc ctcaaacgat 300
tttggccggc tgtgcctggc tgccatcggt ttttatgtgg gcgttctctg catttgggat 360
attctggggg gcata 375

<210> SEQ ID NO 35
<211> LENGTH: 481
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 77536 Cbir-62

<400> SEQUENCE: 35
attgcaatcg tgatgaaccg tacgtgtggt aagctcacgt ttcgaagatg ttgtgtatta 60
ctctattctg ccacttaaga ttctcaccga tacaagcacg ggcacaaatc tctttgaagt 120
ctatacaaaa agccttaaag aagggattac aggcactcaa gaatcgttgc aaaatgttct 180
taaagaatct ggcgaagtag cagaatattc tacaaatgcg gcacaatcag ctgatgatgg 240
cttagatatg agtaaaaagg cattagaaga aattgaagtt ttgtatgaaa aaatgcaaat 300
cgcttctgat ttggtggatt cactcacaca aagaagcaat gaaattacaa gcgtaatctc 360
gcttattgat gatattgcgg aacaaacaaa cctccttgcg ctcaatgcag ctattgaagc 420
accgagagct ggggagcacg gacgaggctt tgccgtgggc gctgatgagg tgcgaaaact 480
c 481

<210> SEQ ID NO 36
<211> LENGTH: 503
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 77538 Cbir-73

<400> SEQUENCE: 36
agctgttgat ggcgacatgg acaaagctat tgatttcttg cgtgaaaaag gtatggcaaa 60
ggctgctaag aagagcgacc gtgttgctgc tgaaggttta gctgatgttg aagttgtagg 120
gaacatagct gcagttgttg aaatcaacgc tgaaacagac tttgttgctc aaaaccaaca 180
attcaaggac cttgtaaaac gtgttgcagg tttgatcgca gaaaataaac cagctgactt 240
agaagctgct ttggctatca agactgacaa aggtacgatc aacgaagaaa tcatcgaagc 300
tacacaagtt atcggtgaaa agatcacatt gcgtcgtttt gaattagttg aaaaagctga 360
caatgaaaac ttcggtgctt acctacacat gggtggtaag atcgccgttt taactgtggt 420
tgaaggtgct gatgaagtgg ctgctaaaga cgttgcaatg cacgttgcag ctatcaatcc 480
taagtacgtg aaccgcgacc aag 503

<210> SEQ ID NO 37
<211> LENGTH: 587
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 77539 Cbir-78

<400> SEQUENCE: 37
cagtgtttct ccggataatc cctttttccc attctctatt tcggataaaa aatttactga 60
aatgtcaacg ctttccgcaa attcggcctg cgtaaaatca ttcaggatcc gcagctgccg 120

```
aatccgttgc ccaatttcgg ttttgttaag agtatctttc ataggttcct ccagaaaagc    180

ggctgcttgt aacagtgggg aaactacagg actgttacgg ccaaattgcc atgattatgg    240

aatgtttgtg ttgctattag tttattttac caatccttaa aaaatagaaa acaaataaaa    300

gattgaatta attctctatt agcgataaaa tataaactaa aagtgacgat atacataata    360

agactggata gggaggagtg gttggaatgg tgattgcaaa taatctattg tcccagttca    420

cagcaaggca gttaaatata aatagcggta agaaagaaaa agcggcagag aaactttctt    480

ccggctaccg cattaacagg gcgtcagata atgcggcggg cttaaaaatt tcggaaaaaa    540

tgcgtatgca gatccgcggg cttatgccgg ggcgcacaaa ataccca                  587


<210> SEQ ID NO 38
<211> LENGTH: 422
<212> TYPE: PRT
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 76779 Cbir-1

<400> SEQUENCE: 38

Gly Gly Ile Ile Met Val Val Gln His Asn Leu His Ala Met Asn Ser
1               5                   10                  15

Asn Arg Met Leu Gly Ile Thr Gln Lys Thr Ala Ser Lys Ser Thr Glu
            20                  25                  30

Lys Leu Ser Ser Gly Tyr Ala Ile Asn Arg Ala Ala Asp Asn Ala Ala
        35                  40                  45

Gly Leu Ala Ile Ser Glu Lys Met Arg Lys Gln Ile Arg Gly Leu Thr
    50                  55                  60

Gln Ala Ser Thr Asn Ala Glu Asp Gly Ile Ser Ser Val Gln Thr Ala
65                  70                  75                  80

Glu Gly Ala Leu Thr Glu Val His Asp Met Leu Gln Arg Met Asn Glu
                85                  90                  95

Leu Ala Ile Gln Ala Ala Asn Gly Thr Asn Ser Glu Asp Asp Arg Ser
            100                 105                 110

Tyr Ile Gln Asp Glu Ile Asp Gln Leu Thr Gln Glu Ile Asp Arg Val
        115                 120                 125

Ala Glu Thr Thr Lys Phe Asn Glu Thr Tyr Leu Leu Lys Gly Asp Thr
    130                 135                 140

Lys Asn Val Asp Ala Met Asp Tyr Thr Tyr Ser Tyr Lys Ala Val Thr
145                 150                 155                 160

Thr Asn Thr Val Ala Arg Ala Ser Val Leu Ala Ala Glu Asn Thr Ala
                165                 170                 175

Thr Gly Met Ser Val Ser Ile Ser Phe Ala Ala Asn Ser Gly Lys Val
            180                 185                 190

Thr Ala Ala Asp Ser Asn Asn Leu Ala Lys Ala Ile Arg Asp Gln Gly
        195                 200                 205

Phe Thr Ile Thr Thr Ser Thr Gln Asn Gly Lys Val Val Tyr Gly Leu
    210                 215                 220

Glu Leu Asn Gly Ser Asp Ala Lys Ala Asn Tyr Thr Val Ser Thr Val
225                 230                 235                 240

Ser Met Glu Ala Gly Thr Phe Lys Ile Leu Asn Ser Asn Lys Gln Val
                245                 250                 255

Val Ala Ser Val Thr Ile Ser Thr Thr Ala Ser Phe Lys Lys Val Ser
            260                 265                 270
```

Gly Met Ser Gln Ile Val Thr Ala Tyr Ser Val Ser Ala Ala Tyr Ala
275 280 285

Thr Gly Asp Val Tyr Ser Leu Tyr Asp Ala Asp Gly Asn Ala Ile Ser
290 295 300

Ala Asn Lys Leu Asp Lys Tyr Phe Thr Ala Gly Gly Ala Thr Glu Ala
305 310 315 320

Gly Gly Ile Ala Thr Thr Leu Ser Ala Asn Ser Gly Val Pro Lys Val
325 330 335

Tyr Asp Val Leu Gly Lys Glu Val Ser Ala Val Ser Ile Ala Ser Thr
340 345 350

Leu Val Thr Ala Val Lys Asp Lys Thr Ala Ala Leu Lys Met Asn Phe
355 360 365

His Val Gly Ala Asp Gly Thr Asp Asn Asn Lys Ile Lys Ile Asn Ile
370 375 380

Glu Ala Met Thr Ala Lys Ser Leu Gly Val Asn Gly Leu Lys Val Ser
385 390 395 400

Gly Ser Ser Gly Thr Asn Ala Thr Asn Ala Ile Glu Ile Ile Ala Gly
405 410 415

Ala Ile Lys Lys Val Ser
420

<210> SEQ ID NO 39
<211> LENGTH: 73
<212> TYPE: PRT
<213> ORGANISM: Unknown
<220> FEATURE:
<223> OTHER INFORMATION: Description of Unknown Sequence:C3H/HeJ Bir mouse cecal bacteria genomic DNA random shear expression library clone 76780 Cbir-2

<400> SEQUENCE: 39

Met Leu Val Asp Asn Cys Ala Met Gln Leu Val Lys Asp Pro Arg Gln
5 10 15

Phe Asp Val Ile Leu Thr Glu Asn Met Phe Gly Asp Ile Leu Ser Asp
20 25 30

Glu Ala Ser Met Val Thr Gly Ser Ile Gly Met Leu Ser Ser Ala Ser
35 40 45

Leu Asn Asp Thr Lys Phe Gly Leu Tyr Glu Pro Ser Gly Gly Ser Ala
50 55 60

Pro Asp Ile Ala Gly Lys Gly Ile Ala
65 70

<210> SEQ ID NO 40
<211> LENGTH: 105
<212> TYPE: PRT
<213> ORGANISM: Unknown
<220> FEATURE:
<223> OTHER INFORMATION: Description of Unknown Sequence:C3H/HeJ Bir mouse cecal bacteria genomic DNA random shear expression library clone 76959 Cbir-3

<400> SEQUENCE: 40

Met Val Gly Thr Leu Val Gly Leu Ile Asn Met Leu Lys Ala Met Asp
5 10 15

Ile Glu Thr Val Gly Gly Asn Leu Gly Pro Ala Met Ala Thr Ala Leu
20 25 30

Val Thr Thr Leu Tyr Gly Cys Val Leu Ala His Met Ile Phe Gly Pro
35 40 45

Ile Ala Thr Gln Leu Arg Gln Arg Asp Glu Glu Glu Thr Leu Cys Lys

-continued

```
     50                  55                  60

Leu Ile Ile Val Glu Gly Leu Met Ser Ile Gln Ala Gly Ala Asn Pro
 65                  70                  75                  80

Lys Phe Leu Arg Glu Lys Leu Leu Thr Phe Val Thr Gln Lys Gln Arg
                 85                  90                  95

Gly Glu Asn Gly Gly Lys Lys Gly Lys
            100                 105


<210> SEQ ID NO 41
<211> LENGTH: 76
<212> TYPE: PRT
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 76959 Cbir-3

<400> SEQUENCE: 41

Met Ala Ser Ile Lys Lys Lys Ser Ser Gly Gly Gly Gly Ala Asn Trp
                  5                  10                  15

Met Asp Thr Tyr Gly Asp Met Val Thr Leu Leu Leu Cys Phe Phe Val
             20                  25                  30

Leu Pro Val Phe His Val His Asp Arg Leu Gly Glu Val Glu Asp Asp
         35                  40                  45

Arg Ser Arg Ala Ser Ile Arg Thr Gln Ser Ser Ala Thr Ile Ser Pro
     50                  55                  60

Pro Asp Arg Thr Ala Leu Lys Ala Ala Arg Ala Ala
 65                  70                  75


<210> SEQ ID NO 42
<211> LENGTH: 152
<212> TYPE: PRT
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 76781 Cbir-6

<400> SEQUENCE: 42

Met Ala Met Ser Arg Ile Gly Arg Leu Pro Ile Ala Ile Pro Ala Gly
                  5                  10                  15

Val Thr Val Glu Ile Ala Glu Asn Asn Val Val Thr Val Lys Gly Pro
             20                  25                  30

Lys Gly Thr Leu Ser Arg Glu Leu Pro Val Glu Met Glu Ile Lys Lys
         35                  40                  45

Asp Gly Glu Thr Ile Val Val Thr Arg Pro Asn Asp Leu Lys Lys Met
     50                  55                  60

Lys Ser Leu His Gly Leu Thr Arg Thr Leu Ile Asn Asn Met Val Ile
 65                  70                  75                  80

Gly Val Thr Glu Gly Tyr Lys Lys Val Leu Glu Val Asn Gly Val Gly
                 85                  90                  95

Tyr Arg Ala Ala Lys Ser Gly Asn Lys Leu Thr Leu Ser Leu Gly Tyr
            100                 105                 110

Ser His Pro Val Glu Met Ile Asp Pro Glu Gly Val Glu Thr Val Leu
        115                 120                 125

Glu Gly Gln Asn Lys Ile Thr Val Gln Gly Ile Asp Lys Glu Lys Val
    130                 135                 140

Gly Gln Tyr Ala Ala Glu Ile Arg
145                 150
```

<210> SEQ ID NO 43
<211> LENGTH: 127
<212> TYPE: PRT
<213> ORGANISM: Unknown
<220> FEATURE:
<223> OTHER INFORMATION: Description of Unknown Sequence:C3H/HeJ Bir mouse cecal bacteria genomic DNA random shear expression library clone 76782 Cbir-9

<400> SEQUENCE: 43

```
Leu Arg Ser Asp Gly Phe Ile Leu Asp Arg Val Thr Asn Gly Pro Trp
                5                   10                  15

Trp Ser Thr Thr Ala Gly Ser Ala Thr Asp Gly His Leu Leu Asn Thr
            20                  25                  30

Tyr Pro Thr Asn Ile Ser Pro Gln Asp Asn Arg Ser Arg Gly Phe Gly
        35                  40                  45

Phe Ala Val Arg Cys Val Val Arg Glu Gly Trp Arg Leu Asn Leu Leu
    50                  55                  60

Pro Thr Arg Arg Trp Ala Phe Ala Trp Arg Tyr Gly Ile Phe Leu Ser
65                  70                  75                  80

Ser Pro Ala Arg Ser Arg Thr Arg His Ser Arg Cys Gly Phe Pro Cys
                85                  90                  95

Ala Pro Pro Cys Cys Ser Ser Gly Phe Cys Ser Ser Ser Cys Cys Arg
            100                 105                 110

Ser Thr Ile Ala Ser Arg Ser Arg Thr Ser Ser Cys Phe Ser Thr
        115                 120                 125
```

<210> SEQ ID NO 44
<211> LENGTH: 143
<212> TYPE: PRT
<213> ORGANISM: Unknown
<220> FEATURE:
<223> OTHER INFORMATION: Description of Unknown Sequence:C3H/HeJ Bir mouse cecal bacteria genomic DNA random shear expression library clone 76967 Cbir-16

<400> SEQUENCE: 44

```
Met Ser Arg Ile Gly Arg Leu Pro Ile Ala Val Pro Ala Gly Val Thr
                5                   10                  15

Val Glu Ile Ala Glu His Asn Val Val Thr Val Lys Gly Pro Lys Gly
            20                  25                  30

Thr Leu Val Arg Glu Leu Pro Val Glu Met Glu Ile Lys Gln Glu Gly
        35                  40                  45

Glu Glu Ile Val Val Thr Arg Pro Asn Asp Leu Lys Arg Met Lys Ser
    50                  55                  60

Leu His Gly Leu Thr Arg Thr Leu Ile Asn Asn Met Val Ile Gly Val
65                  70                  75                  80

Ser Gln Gly Tyr Glu Lys Val Leu Glu Val Asn Gly Val Gly Tyr Arg
                85                  90                  95

Ala Ala Lys Ser Gly Asn Lys Leu Thr Leu Ser Leu Gly Tyr Ser His
            100                 105                 110

Pro Val Glu Met Val Asp Pro Glu Gly Ile Glu Thr Val Leu Glu Gly
        115                 120                 125

Gln Asn Lys Ile Thr Val Lys Gly Ile Asp Lys Glu Lys Val Gly
    130                 135                 140
```

<210> SEQ ID NO 45
<211> LENGTH: 153

<212> TYPE: PRT
<213> ORGANISM: Unknown
<220> FEATURE:
<223> OTHER INFORMATION: Description of Unknown Sequence:C3H/HeJ Bir mouse cecal bacteria genomic DNA random shear expression library clone 76969 Cbir-20

<400> SEQUENCE: 45

```
Val Tyr Met Ile Ile Gln His Asn Ile Ala Ala Ile Asn Ser Tyr Arg
                  5                  10                  15

Asn Leu Gly Val Asn Gln Ser Gly Leu Asn Lys Asn Leu Glu Lys Leu
             20                  25                  30

Ser Ser Gly Tyr Lys Ile Asn Arg Ala Gly Asp Asp Ala Ala Gly Leu
         35                  40                  45

Ala Ile Ser Glu Ser Met Arg Ser Gln Ile Asn Gly Leu Asn Gln Gly
     50                  55                  60

Gly Leu Asn Lys Asn Leu Glu Lys Leu Ser Ser Gly Tyr Lys Ile Asn
 65                  70                  75                  80

Arg Ala Gly Asp Asp Ala Ala Gly Leu Ala Ile Ser Glu Ser Met Arg
                 85                  90                  95

Ser Gln Ile Asn Gly Leu Asn Gln Ala Val Asn Asn Ala Lys Asp Ala
            100                 105                 110

Ile Gly Leu Ile Gln Thr Ala Glu Gly Ala Leu Thr Arg Asp Ser Ala
        115                 120                 125

Tyr Pro Phe Pro Ala Val Cys Cys Arg Ile Pro Ser Leu Ile Arg Asn
    130                 135                 140

Gly Leu Asn Thr Gln Glu Leu Asn Lys
145                 150
```

<210> SEQ ID NO 46
<211> LENGTH: 110
<212> TYPE: PRT
<213> ORGANISM: Unknown
<220> FEATURE:
<223> OTHER INFORMATION: Description of Unknown Sequence:C3H/HeJ Bir mouse cecal bacteria genomic DNA random shear expression library clone 76972 Cbir-27

<400> SEQUENCE: 46

```
Met Met Cys Ile Arg Asn Leu Arg Thr Glu Arg Ser Ser Ile Trp Ile
                  5                  10                  15

Arg Phe Val Ile Pro Leu Lys Arg Glu Gln Ile Arg Leu Ser Ser Gly
             20                  25                  30

Lys Thr Gln Gly Lys Ala Gly Asp Pro Met Pro Tyr Ile Pro Pro Glu
         35                  40                  45

Val Ile Glu Gln Ala Arg Gln Ile Asp Leu Leu Ser Tyr Met Lys Ala
     50                  55                  60

Phe Glu Pro Asn Glu Leu Val Arg Ile Ser Gly Asn Asn Tyr Thr Thr
 65                  70                  75                  80

Arg Thr His Asp Ser Leu Lys Ile Ser Asn Gly Lys Trp Met Trp Trp
                 85                  90                  95

Ser Gln Arg Ile Gly Gly Tyr Asn Ala Leu Asp Tyr Leu Ile
            100                 105                 110
```

<210> SEQ ID NO 47
<211> LENGTH: 22
<212> TYPE: PRT
<213> ORGANISM: Unknown
<220> FEATURE:
<223> OTHER INFORMATION: Description of Unknown Sequence:C3H/HeJ Bir mouse cecal bacteria genomic DNA random shear expression library
clone 76974 Cbir-32

<400> SEQUENCE: 47

Met Gly Val Phe Gln His Ala Val Phe His His Val Leu Gly Ala Gln
5 10 15

Gln Leu Phe Leu Gly Gly
20

<210> SEQ ID NO 48
<211> LENGTH: 140
<212> TYPE: PRT
<213> ORGANISM: Unknown
<220> FEATURE:
<223> OTHER INFORMATION: Description of Unknown Sequence:C3H/HeJ Bir
mouse cecal bacteria genomic DNA random shear expression library
clone 76975 Cbir-39

<400> SEQUENCE: 48

Asp Asn Thr Lys Lys Arg Gln Gly Asn Gly Lys Gln Gly Ser Tyr Met
5 10 15

Arg Ile Gln His Asn Ile Ser Ala Ile Asn Ser Gln Arg Asn Ile Met
20 25 30

Thr Thr Asp Arg Ala Leu Ser Lys Asn Leu Glu Lys Leu Ser Ser Gly
35 40 45

Tyr Arg Ile Asn Arg Ala Gly Asp Asp Ala Ala Gly Leu Ala Ile Ser
50 55 60

Glu Ala Met Arg Asn Gln Ile Thr Ala Met Asn Gln Gly His Glu Glu
65 70 75 80

Cys Ala Gly Arg Asn Phe Pro Gly Ala Asp Gly Arg Arg Arg Pro Asp
85 90 95

Arg Ser Pro Tyr His Ala Gln Pro His Glu Gly His Gly Gly Ala Gly
100 105 110

Arg Gln Arg Asp Ile His Gly Ile Arg Thr Gly His Val Lys Leu Arg
115 120 125

Asp Gly Arg Ala Lys Gly Arg Asp Tyr Thr Tyr Trp
130 135 140

<210> SEQ ID NO 49
<211> LENGTH: 198
<212> TYPE: PRT
<213> ORGANISM: Unknown
<220> FEATURE:
<223> OTHER INFORMATION: Description of Unknown Sequence:C3H/HeJ Bir
mouse cecal bacteria genomic DNA random shear expression library
clone 76977 Cbir-44

<400> SEQUENCE: 49

Ala Ala Glu Arg Leu Ser Ser Gly Tyr Arg Val Asn Arg Ala Ala Asp
5 10 15

Asp Ala Ala Ala Met Ala Ile Ser Glu Lys Lys Arg Ala Gln Ile Arg
20 25 30

Gly Leu Ala Arg Ala Ser Lys Asn Ala Gln Asp Gly Ile Ser Phe Val
35 40 45

Gln Thr Gly Asp Gly Ala Met Ser Gln Ile Gly Ala Met Leu His Arg
50 55 60

Met Arg Glu Leu Thr Val Gln Ala Leu Asn Asp Gly Val Tyr Glu Pro
65 70 75 80

Ala Asp Arg Ala Ala Leu Gln Met Glu Phe Asp Gln Leu Gln Gly Glu
85 90 95

```
Ile Asp Arg Val Asn Asp Gln Thr Glu Phe Asn Lys Lys Pro Val Phe
            100                 105                 110

Glu His Tyr Thr Asp Asn Phe Ser Leu Leu Glu Gly Asn Arg Val Trp
        115                 120                 125

Ser Gln Asp Gln Ile His Thr Ile Asp Ser Ser Asn Ser Ser Leu Thr
    130                 135                 140

Val Lys Tyr Ile Ala Val Glu Pro Asp Gly Thr Glu Val Glu Lys Glu
145                 150                 155                 160

Lys Thr Leu Thr Ile Pro Glu Gly Thr Tyr Thr Thr Arg Glu Leu Met
                165                 170                 175

Asp Glu Met Asp Asn Val Val Ser Ala Leu Gly Asp Glu Ala Asp Gly
            180                 185                 190

Leu Tyr Leu Glu Tyr Ser
        195


<210> SEQ ID NO 50
<211> LENGTH: 115
<212> TYPE: PRT
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 77076 Cbir-61

<400> SEQUENCE: 50

Met Glu Ala Val Gly Leu Tyr Gln Met Ile Leu Gln Val Leu Trp Leu
                5                   10                  15

Ile Leu Leu Phe Ala Gly Ile Ser Leu Leu Phe Gly Arg Val Ala Gly
            20                  25                  30

Ile Val Thr Gly Ser Val Leu Ala Val Ser Phe Trp Met Met Glu Thr
        35                  40                  45

Ile Leu Val Ile Trp Pro Gly Asn Phe Tyr Met Leu His Phe Thr Ile
    50                  55                  60

Ala Leu Met Phe Leu Gly Tyr Val Arg Tyr Arg Ile Lys Lys Gly Gly
65                  70                  75                  80

Trp Pro Ser Asn Asp Phe Gly Arg Leu Cys Leu Ala Ala Ile Gly Phe
                85                  90                  95

Tyr Val Gly Val Leu Cys Ile Trp Asp Ile Leu Gly Gly Ile Pro Arg
            100                 105                 110

Ala Glu Phe
        115


<210> SEQ ID NO 51
<211> LENGTH: 132
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 73261 CB1-T2

<400> SEQUENCE: 51

gttcccatga tctcaaaaca ttctttatat tccatcaggc ggcttccgca tttctccagt      60

tcttcataaa gctgctggat ctgcggtttt ttctttccct taccgcaaac aaactccatt     120

ccttccccta cc                                                         132


<210> SEQ ID NO 52
<211> LENGTH: 511
```

<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 73262 CB1-T3

<400> SEQUENCE: 52

```
cctggcagag cacgccgcac gccataaccg ggagcggcat cgcattcaaa tcctccgcca     60

actggaaata ctccatataa ccaagcccca gcgtcatcat ataaccccag acattaaaat    120

tttccctgcg tttctcgacg atatccaccg aatccttcca atcataaaca ttatcccaga    180

tataggaacc ttccgagata cagccgccag gaaagcgaag gaaagtagga tgcagctctc    240

tcattgtctc tacaaggtcg cggcgcagac ggtaattcgg attcctaaga taatttttat    300

gggcgctcgc gctgccctcc tcctcaccaa atccccagac atgttccggg aacatcgaaa    360

ccatatcgat ggatatactg ccggaaaaag ccaattctaa ctgcccgaaa cactccttct    420

ctgccgtaag taccaccgct tgtttttccc cgtatttctt ccagtcgccg gatatggaaa    480

tttttccac attgctgacc gccgcccccg a                                   511
```

<210> SEQ ID NO 53
<211> LENGTH: 213
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 73263 CB1-T4
<220> FEATURE:
<221> NAME/KEY: modified_base
<222> LOCATION: (1)..(213)
<223> OTHER INFORMATION: n = g, a, c or t

<400> SEQUENCE: 53

```
atcgggaaaa agaaatactt tttatggatt tgcgacagat aggaagtaca tatgaaaaga     60

gtaccctttt ccgtatttct gcccgcccgg tcggtcagaa atggcttgtt gggaagtgtc    120

ccaaaccctc tatgagaacg gaaaggagcg aaaacccatg aacggacgca aaaggacggn    180

acaggtcaaa ttctatgnga cagangaaga aac                                213
```

<210> SEQ ID NO 54
<211> LENGTH: 511
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 73264 CB1-T5

<400> SEQUENCE: 54

```
gtacaggttc tcggtctcga ccccgcagtg ggccagaagc cgggaggccc cgttgccctt     60

ggtgcgcagc aggcccagga gcagatgctc ggagttcacc gcgttctggc ccagccggcg    120

gctctcctcc accgcgccct ggatggctga gcagcagttg ggcgtaagtc cctgaaagct    180

ggactgggcg ggcactcccg tccccacccg ctgggcgatg gcggagcgca gggcctggct    240

gtccgccccc gcccggcgca gggccatggc ggcggggctg aactcctggc cggccagccc    300

aagcagaaga tgctcgctga atagccaaat aaaaccatat cactaatgtt atacaatctt    360

cctgaaaaac agccattact gcatgtaatc aatctccctt ttgcttttgt ttcaatatga    420

agcgggtttt cccacaatat ctgcattaaa taagataaat taccctcccc atatattctc    480
```

tgatcggttc gtgtttttaa tatatattca c 511

<210> SEQ ID NO 55
<211> LENGTH: 511
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 73266 CB1-T7

<400> SEQUENCE: 55
cctacaggcc aggacatgac ggcttgcgcg agctttacct gaattgccgc cgccttgtat 60
atgcctacaa taatctccat cctgacaaga ttggggaaag ggacgacctg attcgaagga 120
ttctcggcaa atgcggcgag cgtgtggcag tggagccgcc ctttcattgt gattatggcg 180
ttcatattga agttggcgac aatttttttg ccaacttcaa ttgcgtaatc ctggatgttg 240
ccagggtcat gatcggcaaa aatgtcatgt ttgcgcccaa tgtgggaatt tatgcggctg 300
gccatcctgt tcattggcaa agccgcaatt cgggctatga atatggtcgg gaaatcagga 360
ttggcgacaa tgtctggctt ggcgggaatg ttatcgtcaa tcccgggata aatataggca 420
ataatgttgt tgtaggctcg ggcagcgttg ttaccaggga tatcccggac aatatgctgg 480
cagcgggtaa tccctgcagg gttttgcgcg a 511

<210> SEQ ID NO 56
<211> LENGTH: 279
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 73267 CB1-T8

<400> SEQUENCE: 56
gataattatg aggaggcctt ggacagtgta gaggaagtca agcgttccct tctggtagcg 60
ttggtggacc gcaaggtgag caaatatttc tccgagcggg acagcattat taagaaaata 120
gaaaaagaca aatattttgt ggcatttaag caaaaatatc tggacgagct gattgaggac 180
aagtttagta tccttgagga cgtcaagact gttaaagtgg gaaatgagat ggcagtcacc 240
ttgagcattg gggtgggcgt cagcgggaac agttatacc 279

<210> SEQ ID NO 57
<211> LENGTH: 234
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 73268 CB1-T9

<400> SEQUENCE: 57
cacttacgaa gatgtggtac tgccgcctct atggcatcat aatattacag tatttgatgc 60
ctagagcatg tctgaaaatt cattcccgcc atcttcacgc cccactttgc gatttatttg 120
gctctcattc ggtcaacgta gctcactacg cctaccacat gatctacttt cgaaaaaaca 180
accttaaata accttacatt tcaccagtct atttttctgg cgaaatgtgt ggtc 234

<210> SEQ ID NO 58
<211> LENGTH: 164
<212> TYPE: DNA
<213> ORGANISM: Unknown

<220> FEATURE:
<223> OTHER INFORMATION: Description of Unknown Sequence:C3H/HeJ Bir mouse cecal bacteria genomic DNA random shear expression library clone 73269 CB1-T10

<400> SEQUENCE: 58
acattgcgaa atacaatctc acctttcggc tggaccaact cctgcgcgtc cggctcatca 60
aaaatctcta tatcagcatc cataatctgc aagaaccgct caatgccagt gattccgcgc 120
tgaaactgct ctgcaaactc aataatcctg cggattgtcg caac 164

<210> SEQ ID NO 59
<211> LENGTH: 511
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 73270 CB1-T11
<220> FEATURE:
<221> NAME/KEY: modified_base
<222> LOCATION: (403)
<223> OTHER INFORMATION: n = g, a, c or t

<400> SEQUENCE: 59
gagaaaaaat tttctttgaa ccggaaaaaa caaaggtcgc cattgtgaca tgcggcggtt 60
tgtgtccggg gctcaacgat gtgatccgtt ccattgtcat ggaattatgg catggatacg 120
gcgtgcggga cattatcggc attccttacg gcttggaggg gtttatccct aaaaaatacg 180
gacataagct tattgagctg acccctgatg ctgtttcaac aatttatatg ttgggcggaa 240
caattttagg ttcttcacgc ggagcgcaga attttgacga aatagcggat tttttgaatg 300
agaaagggat taatttgctt ttcgtgcttg gcggcgacgg taccatgaaa gccgcaaagg 360
ctatttcaac agcggtgaaa gagcatggtt tgaccctgtc ggntatcggt attcctaaaa 420
ctattgataa tgacatcaat tttgtggagc agtctttcgg gttcgccacc gctgttgacg 480
aggcgacaaa agccattgcg gcggcgcata c 511

<210> SEQ ID NO 60
<211> LENGTH: 208
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 73272 CB1-T13
<220> FEATURE:
<221> NAME/KEY: modified_base
<222> LOCATION: (1)..(208)
<223> OTHER INFORMATION: n = g, a, c or t

<400> SEQUENCE: 60
actcggcgta ccgggccatg gtatgggggt actggtactg ggagaaggtg cccatcttgg 60
gcgggcactc cgcgctgttg tattccacca ccagggagat cagcagtgcg ttggctacgc 120
cgtggggcag gtggtggaac gcgcccagat tgngggccat ggagtggcat acncccatca 180
accaattngc aaaggccatg ccagccag 208

<210> SEQ ID NO 61
<211> LENGTH: 275
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 73273 CB1-T14

<400> SEQUENCE: 61
agcgtggaaa tcccatccag tgtgaaatgg atattggatt ctgcctttttc aagatgcagc 60 agcttaacaa gcgtggcaat tcccccaagc gtgacaggga tagcttataa tgctttctta 120
ggctgcagcg acaacctcgt aatcgttgga actcctggtt cagaagcaga gaaatatgca 180
caacagaaca acattacatt taaatttctt gattccgttc aggacatatc cgaagcatct 240
ataaccttgg agagggcaag ctacacctat gacgc 275

<210> SEQ ID NO 62
<211> LENGTH: 357
<212> TYPE: DNA
<213> ORGANISM: Unknown
<220> FEATURE:
<223> OTHER INFORMATION: Description of Unknown Sequence:C3H/HeJ Bir
mouse cecal bacteria genomic DNA random shear expression library
clone 73274 CB1-T15

<400> SEQUENCE: 62
cctgtttctt taaacatggc gtccagccgt ttctgaatat tctcccagat ggcatagccg 60
ttgggccgga taatcataca tccctttata ttggaatact ccaccagctc cgccttgcgc 120
accacatccg tataccactg cgcgaaatcc tcgttcatcg acgtaatcgc ctcaaccaac 180
ttcttttcct ttgccataat aacctccatt caaatttgca gcttccgttc caggcacttc 240
tgaaccggga gaattttcag tcattcaaat ctctgtaaat cctgccgggg gttttacggt 300
ccgctgctgt tttatgatag ttccgcggtt tccttcccat tgccgcacgc acttcgc 357

<210> SEQ ID NO 63
<211> LENGTH: 376
<212> TYPE: DNA
<213> ORGANISM: Unknown
<220> FEATURE:
<223> OTHER INFORMATION: Description of Unknown Sequence:C3H/HeJ Bir
mouse cecal bacteria genomic DNA random shear expression library
clone 73275 CB1-T16

<400> SEQUENCE: 63
tatacgtcca aagacagtat tgacattctg gagaagttct ttccggacga taaggaagcc 60
agggaagaaa aataagtagc tataagatat ttttaggtga tcaggccgga ttggaggaaa 120
tatatgataa cattgaccga gaatgaaaag aggatggtat ttcagctgga aggctgcaac 180
agatatgatg cgatacagga gattgctgtg ttctgccagt atacccgtga ccatgacaaa 240
aggaacattg ccgaaaatct gttaaagaaa cttcgtgaac tctcagaaaa tgactgtagg 300
gagctgattt gtgatattca gaaaaattat aatctgcctc ggaaagcaaa gactgttgga 360
gagatgattg ctgtgc 376

<210> SEQ ID NO 64
<211> LENGTH: 626
<212> TYPE: DNA
<213> ORGANISM: Homo sapiens

<400> SEQUENCE: 64
tgtagatctc ctccgccgcg cacagctcca ccagccggcc caggtacatc acccccacca 60
cgtcggagac atagcgcacc atggacaggt cgtgggcgat gaacagatag gccagccccc 120
gctcctgctg gtagtcccgg aggaggttga ccacctgggc ctggatggac acatccagag 180
cggagatggg ctcgtcgcag atgaccagat cgggctggag gatcagcgcc cgggcgatgc 240

-continued ccacccgctg gcgctggccg ccggagaact cgtgggcgta gcgcccggcg tgctccgccg 300
tcagccccac ccgctccagc atggggtaga cgtagtcgtt ggcctcctgc ttggtcttga 360
ccacatggtg ggccagcagg ggctcggcga tgatgtcccg gacggtcatc cgggcattga 420
gggaggcgta ggggtcctgg aagatcatct gcatcttgcg gcgccggggc tggagctcct 480
tttgggacat gcgggtgatg tcctcgccgt ccagcacgat cttcccggcg gtggggtcgt 540
acatgcggat gatagaccgg gcgcagctgg acttgccgca gcccgactcg cccaccaggc 600
ccagggtctc cccccggcgg atggag 626

<210> SEQ ID NO 65
<211> LENGTH: 457
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 75038 CB3-T2

<400> SEQUENCE: 65
tcagactttc agaatctcct gttttgccat attcccggtt atcgtcagtc aacgatgccg 60
ccgcatcgcc tctttccccc ttgcaggctg aaaaatattc gctctgacag cctgcttact 120
ggccggattg agcgccagag gaaatcagga cacaaaaaag cagtgaaaaa attttcacag 180
aaaatttgca cgtacttttt caaattttcc acatccgttt tttcactgct ttttgatacc 240
ttaatcctgc atgagaacaa tagtatattg ataaatttaa ggctggtact gctgttccag 300
aatctgttcc acattttccg ccgtaacaat gcgatagggg agactcacat agatgtcatc 360
caccagcgct atatcctccg gcagctctgt gccctgcccc agagaatacg caatttccag 420
aatactgtgc gcctgtccgg gagcgtcgtt cagcact 457

<210> SEQ ID NO 66
<211> LENGTH: 364
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 75039 CB3-T3

<400> SEQUENCE: 66
cggcataggc gagttttgtt tggaattaca ttcgggcaag tctgcggaca agtcggaaat 60
tataagaaat atagaaacca cgctttcgct caccgccgaa aacgacgggg aagagtttat 120
aaatgctggc gcgagaatac gcgaaacgcg cgaggcgctg cacgcgcccc ttgcggcttt 180
gcataaaaag cgtaggctgg gcgtttccgt ttacgagggg atagtttact atttgcaaaa 240
taaatccgcg cccgagcttt taaatataga aactactttc tacgattctt taaccaaaca 300
aaagttagag gattacgaaa atatgcttat taccgctcaa gcggcggcaa aggagtgcgg 360
cgcc 364

<210> SEQ ID NO 67
<211> LENGTH: 616
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 75040 CB3-T4

<400> SEQUENCE: 67
ggttcctgct gcttgcagca ttcctcttcg cgagatcctc ccctcgcacg cacgcatggc 60
tgtgctccac gaaggtgtac cggcgctacg tcgccgcgtt caagcaagcc ggaggcattc 120
cgctttccac gaagatccgg atagtcggcg tctcgtacgc catgatgggc gtcagcgcgc 180
tggtcgtcca gaagccgctg gtgtgggcgg tcctggggtg cgtggccgtc ttcctcctgt 240
atctgatggc cgtccgcatt ccgaccatcg agcagaagcg tgtcgatcga gcccgggcag 300
aagacgtggc ctgagtcacg gcaagccacc aagagcgccg gcgccgcagc catggcgcac 360
atggctcacc agaaggtcga agccatggag gcgacgagac cccccgccta gtgcggcggg 420
agcagctatc agaaccgtgt cggagctggg cggtagaccg catcttcgac gagccgctgg 480
ccacgatgct gcctgcctct catcatggcc aagcttcgct tcaagcatgc tgagcgcctg 540
ttttctcgca ccggacattt cgaaacgcgc tggatgcaag gatgcaacca aagacgacac 600
gaacgtgaaa catacg 616

<210> SEQ ID NO 68
<211> LENGTH: 369
<212> TYPE: DNA
<213> ORGANISM: Unknown
<220> FEATURE:
<223> OTHER INFORMATION: Description of Unknown Sequence:C3H/HeJ Bir
mouse cecal bacteria genomic DNA random shear expression library
clone 75041 CB3-T5

<400> SEQUENCE: 68
gctgtataaa aacggcgtgc ttgcggaaaa gaagcccgta agcttttaca gcgggctgaa 60
cgtggttacg ctgccgcttt acaccgatga ggagggcacc ttcgattacg agttgaaggt 120
tgaggcggcg gagccggacg gagatttttc gccgcataac aacgtttgct attttacgca 180
gaaggtgacc aacgagcgca aggtgctgtt tttgggcggc tctgccgcgg atttggcggc 240
gggcaaaaga atttacggcg agaaggacgt aagctatata agcgacgtga agcaggtgcc 300
cgtgacggtg gaggatatgt gcggctatga cgaaattgtt ttaagcaact tcgacgtgcg 360
cacggtaag 369

<210> SEQ ID NO 69
<211> LENGTH: 604
<212> TYPE: DNA
<213> ORGANISM: Unknown
<220> FEATURE:
<223> OTHER INFORMATION: Description of Unknown Sequence:C3H/HeJ Bir
mouse cecal bacteria genomic DNA random shear expression library
clone 75042 CB3-T6

<400> SEQUENCE: 69
ggcctatgga gccgatgggg tctattggga aagggaaagc aaggacggtt ccgtgaaaaa 60
ggttggggaa cgctgccaga cctgtgcgga acggaaatat caggacggtt ctgatgaaaa 120
tgtttccttt aaggcggcag cccatatttc cccggaagca gcaggcagcg cagtgcgcgc 180
ccatgaaggg gagcatgtgt ccaatgccta tacaaaggcg gcaaagaatg atgggaaggt 240
tgtgtcagca tccgtcagca tccatacttc tgtctgcccg gaatgtggca ggacgtatgt 300
atcgggggga accacatcca cccggattaa atacccggct gacccttatg aaaagagcaa 360
aaaggtgctt ggggaggaag aagccaaagg gaaaaatatt gattatgcag cttaatttaa 420
ggaggtaaga atgatgaaga aattcagaac gaaaataacg gcaatgatgt gcatgatgtt 480
ctgccttgtg gcggcagggg tgctcttaac ccctaatacg gcatttgcga agaaaattac 540

```
ccgggacagc caggccgaat ccatggcaag gaaaaaagta aaaggcggga ctgtcgtaga    600

aatc                                                                 604


<210> SEQ ID NO 70
<211> LENGTH: 282
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 75044 CB3-T9

<400> SEQUENCE: 70

ggccacaata caaccatcac ccagactaat tcccgtagaa ctatttacac ccaaaaggca     60

atttttgccg atactaattg gctcactatt tccgccactt aaaacaccaa gtatgctagc    120

cccaccgccg acatcgctcc cctcacctac gacaacacta gagctaatgc gcccttcatt    180

catacaagca cccattgcac cagcattgaa attcacataa cttgctccgg gcatttgtgt    240

ataaccacct ttgccaagat acgctccaaa acgggttttt cc                       282


<210> SEQ ID NO 71
<211> LENGTH: 544
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 75045 CB3-T10

<400> SEQUENCE: 71

ggatttattc ctttttatac ttttgtggct tccaaatttt gaaatatacg tattttgaaa     60

ttattaagaa aatataaata catttttttg aaatttttat ttaaaaatat attgacattt    120

agaaataaat attttataat acagttacct taatcaatct actttatcag cttcgcattt    180

tactgtctgg aggtaagctt gagcaacggt acaattgcga tttatgattc agaagcagac    240

tatgctttaa aacttgcaga atattttcgc ctgaaaaatg gattaaacta ttctgtctcg    300

gtattcaccg attataattc ccttaagaat tatttatctg aaaatgatat tgatatactt    360

ttaatttctg aagaattttg tatgtatata gaagaattac agaatgtatc caatctgttt    420

atccttacag atggaaatat agatgctgcg ctaaagcagt atgcatccct atacaaatat    480

cagccagccg ataggatgct tcgggatatc atgtcctgtt atgcactctc ttcttccaga    540

gaaa                                                                 544


<210> SEQ ID NO 72
<211> LENGTH: 664
<212> TYPE: DNA
<213> ORGANISM: Unknown
<220> FEATURE:
<223> OTHER INFORMATION: Description of Unknown Sequence:C3H/HeJ Bir
      mouse cecal bacteria genomic DNA random shear expression library
      clone 75046 CB3-T12

<400> SEQUENCE: 72

gatactatat cttgtatact caaagcttat tgcgacagcc cctaggctga cctgttacat     60

acaagcaaca ggtcatacgc cacttgtgca gcatacttcc tctgcacggg tctatgcata    120

aaatcaaaat cgagtaggag atatttcttc ccctactcgc cgccggattc tccatttact    180

taaatcgtac agctgttccg tatgccataa cttcggctgc gccttgcatt accgcagccg    240
```

aagcataacg cacatttaaa accgcatctg caccaagctg ctctgcttcc tcaaccatcc 300
gctttgttgc aagcgccctc gcttcattca tcatatccgt atacgctttt aactcgccgc 360
caacaagcgt tttaaaactt tgtgtaatat ctttaccaaa gtttttactt tgaattgtac 420
tgccctttac caaaccaagc atttctgttt cttttcctga tatataatca gtatttacta 480
agatcatctt cttccccact ccttatttca ttcattcttt ccacaagcac atatacaaca 540
acgccgatta gcgcaagtgg tatcactcca aacaaaattt tcgttatcaa caacactgac 600
atactaaaac atatcgccgc ataaaaacaa aaataaatca ctggaataat agaaatcaca 660
attg 664

<210> SEQ ID NO 73
<211> LENGTH: 613
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 75047 CB3-T13

<400> SEQUENCE: 73
ggccaggccc gttataggga atatctccat gaatctcata atccggataa tgaaccgcat 60
attcttttaa aatttcaatg gccttgtccg cataggcctg ctctcctgta gccagccaaa 120
tcactgccat agagaatgcc ccttcataat tccccccatt gatcagtccc caccaggcac 180
tgtcataggg ttctcctgta aataccttt tacaggaagg gcatctgtgt ttatggggac 240
tgtttctgtc aaaatcaagc tttaccgagc agtccggaca atagtaataa agcgtccagt 300
tggcgatccc cctttcggga accattatct caccattaaa gatctcatct acttcctttt 360
ttagccgctt aattgtggca ggataacggc tgcttctctc tctcagatgt tttctctctt 420
catccgtaaa ctgaatcatt ttccttctcc ccttttatca caatttttcc tgtttctgat 480
acagccaaag agcccctttc ctttaaacgc tgtccggctt caaagtttct ttaaactctg 540
taggcgtaca cccgtagaac tttttaaagc tgctggaaaa ataccgctga ttgtcatacc 600
cgcagcgttc tgc 613

<210> SEQ ID NO 74
<211> LENGTH: 514
<212> TYPE: DNA
<213> ORGANISM: Unknown
<220> FEATURE:
<223> OTHER INFORMATION: Description of Unknown Sequence:C3H/HeJ Bir mouse cecal bacteria genomic DNA random shear expression library clone 75048 CB3-T14

<400> SEQUENCE: 74
ttcatcactt aatgaataaa gcactggcag gtccattgga aggaaacggc gtatctctgt 60
tttacagtca aattggtgta atgccttgtt ggcaacactt gaaagatatt ccatacgctg 120
gtattcatat ggctgtaatt cttctaatac aaagtccatg ctttcttcct ggaatggcgc 180
aagcggaagt gaatacatat gtgcaagttt ccttatcagt tcttcatcat atacataccc 240
tgcacatatt aaaagccttc cctgtgccat atataaaggc cttaactggt taaatcttga 300
gactgagcca atccagtctg cttcacccac tttctttaaa agctctcctg tgtaagtgcc 360
ctcgcttgtt tcaaatggca gataatctat aaacaagtgg aaaagcctgt catcccatac 420
tgacattgat ttaataagct tgtttttatc tgtaataacc tctctgtctg caagcatttc 480
ccccctgtca gtcattctgc aataatccaa atca 514

<210> SEQ ID NO 75
<211> LENGTH: 1377
<212> TYPE: DNA
<213> ORGANISM: Unknown
<220> FEATURE:
<223> OTHER INFORMATION: Description of Unknown Sequence:full-length CBir-1 Flagellin X clone 83537 cDNA from C3H/HeJ Bir mouse cecal bacteria genomic DNA random shear expression library PCR amplification

<400> SEQUENCE: 75

```
gtagtacagc acaatcttag agcaatgaat tctaacagaa tgttaggcat cacacaggga     60
tctttaaaca aatctacaga gaagctctca tcaggctaca aggtaaacag ggcagcagat    120
gatgcagcgg gtctttcaat ttccgagaaa atgagaaaac agatcagagg actgtcacag    180
gcatctttga atgctgagga tggtatcagt gcagtgcaga ccgcagaggg cgcattgaca    240
gaagttcatg acatgttgca gagaatgaac gagctggcag taaaggctgc aaacggcaca    300
aactctacat cagaccgtca gacaattcag gacgaggtag accagctcct cacagaaatc    360
gaccgtgtcg cagagaccac caaattcaat gagctgtata cattgaaggg tgatgaggac    420
aaggtgacaa gatatctttc agcacatgac gcaggtatag aaggaacctt gacacagggc    480
gctacaaacg cgacattttc aatggaccag ttaaagtttg gcgacaccat catgatcgca    540
ggcagagagt accatatcag cggaaccaag gcagagcagg cagcaatcat tacggcttct    600
gtgaagattg gacagcaggt tacgattgat ggaatcatgt atacctgttc atcagtaagc    660
aatgctgaca aatttgaact gaaaagtgag gatttgattg caaaactcga cacttcaagc    720
ctgagtatta tgtcagtgaa tggcaagacc tactacggcg caggcatcac agatgacagg    780
actgttgtaa gttcaattgg tgcatacaag ctgattcaga aggagctcgg actggcaagc    840
agcattggtg cagacggcgc aacacaggct tcggtaaatg ccggagtaga tggcaagact    900
ttgatgaagc cgagttttga gggcaaatgg gtatttagta tcgacaaggg aagcgttcag    960
gtacgcgagg acattgattt cagcctccat gtaggtgcag atgccgacat gaacaacaag   1020
attgcggtga agatcggagc gcttgacacg aagggacttg gtatccaagg actgaatgta   1080
aaggatacga caggcgcagc agcgacctac gcgattgatt cgattgcgga cgcagtggca   1140
agaatttctg cgcagcgctc tttactcggt gcagtgcaga accggttaga gcacacgatc   1200
aacaacttgg ataacgttgt agagaacaca accgccgcag agagccagat ccgtgataca   1260
gacatggcga cagagatggt gaagtactct aataacaacg tacttgcaca ggcaggccag   1320
tcaatgttag cacagtctaa tcaggcaaat cagggtgtac ttcagctctt acagtaa      1377
```

<210> SEQ ID NO 76
<211> LENGTH: 450
<212> TYPE: DNA
<213> ORGANISM: Unknown
<220> FEATURE:
<223> OTHER INFORMATION: Description of Unknown Sequence:clone CBir-1 truncated Flagellin X amino terminal conserved end from C3H/HeJ Bir mouse cecal bacteria genomic DNA random shear expression library PCR amplification

<400> SEQUENCE: 76

```
gtagtacagc acaatcttag agcaatgaat tctaacagaa tgttaggcat cacacaggga     60
tctttaaaca aatcgacaga gaagctatca tcaggctaca aggtaaacag ggcagcagat    120
gatgcagcgg gtctttcaat ttccgagaaa atgagaaaac agatcagagg actgtcacag    180
```

gcatctttga atgctgagga tggtatcagt gcagtgcaga ccgcagaggg cgcattgaca 240
gaagttcatg acatgttgca gagaatgaac gagctggcag taaaggctgc aaacggcaca 300
aactctacat cagaccgtca gacaattcag gacgaggtag accagctcct cacagaaatc 360
gaccgtgtcg cagagaccac caaattcaat gagctgtata cattgaaggg tgatgaggac 420
aaggtgacaa gatatctttc agcacattaa 450

<210> SEQ ID NO 77
<211> LENGTH: 990
<212> TYPE: DNA
<213> ORGANISM: Unknown
<220> FEATURE:
<223> OTHER INFORMATION: Description of Unknown Sequence:clone CBir-1 truncated Flagellin X amino terminal conserved end plus variable portion from C3H/HeJ Bir mouse cecal bacteria genomic DNA random shear expression library PCR amplification

<400> SEQUENCE: 77
gtagtacagc acaatcttag agcaatgaat tctaacagaa tgttaggcat cacacaggga 60
tctttaaaca aatctacaga gaagctctca tcaggctaca aggtaaacag ggcagcagat 120
gatgcagcgg gtctttcaat ttccgagaaa atgagaaaac agatcagagg actgtcacag 180
gcatctttga atgctgagga tggtatcagt gcagtgcaga ccgcagaggg cgcattgaca 240
gaagttcatg acatgttgca gagaatgaac gagctggcag taaaggctgc aaacggcaca 300
aactctacat cagaccgtca gacaattcag gacgaggtag accagctcct cacagaaatc 360
gaccgtgtcg cagagaccac caaattcaat gagctgtata cattgaaggg tgatgaggac 420
aaggtgacaa gatatctttc agcacatgac gcaggtatag aaggaacctt gacacagggc 480
gctacaaacg cgacattttc aatggaccag ttaaagtttg gcgacaccat catgatcgca 540
ggcagagagt accatatcag cggaaccaag gcagagcagg cagcaatcat tacggcttct 600
gtgaagattg gacagcaggt tacgattgat ggaatcatgt atacctgttc atcagtaagc 660
aatgctgaca aatttgaact gaaaagtgag gatttgattg caaaactcga cacttcaagc 720
ctgagtatta tgtcagtgaa tggcaagacc tactacggcg caggcatcac agatgacagg 780
actgttgtaa gttcaattgg tgcatacaag ctgattcaga aggagctcgg actggcaagc 840
agcattggtg cagacggcgc aacacaggct tcggtaaatg ccggagtaga tggcaagact 900
ttgatgaagc cgagttttga gggcaaatgg gtatttagta tcgacaaggg aagcgttcag 960
gtacgcgagg acattgattt cagcctctaa 990

<210> SEQ ID NO 78
<211> LENGTH: 399
<212> TYPE: DNA
<213> ORGANISM: Unknown
<220> FEATURE:
<223> OTHER INFORMATION: Description of Unknown Sequence:clone CBir-1 truncated Flagellin X carboxy-terminal conserved end from C3H/HeJ Bir mouse cecal bacteria genomic DNA random shear expression library PCR amplification

<400> SEQUENCE: 78
ttcagcctcc atgtaggtgc agatgccgac atgaacaaca agattgcggt gaagatcgga 60
gcgcttgaca cgaagggact tggtatccaa ggactgaatg taaaggatac gacaggcgca 120
gcagcgacct acgcgattga ttcgattgcg gacgcagtgg caagaatttc tgcgcagcgc 180
tctttactcg gtgcagtgca gaaccggtta gagcacacga tcaacaactt ggataacgtt 240
gtagagaaca caaccgccgc agagagccag atccgtgata cagacatggc gacagagatg 300
gtgaagtact ctaataacaa cgtacttgca caggcaggcc agtcaatgtt agcacagtct 360
aatcaggcaa atcagggtgt acttcagctc ttacagtaa 399

<210> SEQ ID NO 79
<211> LENGTH: 458
<212> TYPE: PRT
<213> ORGANISM: Unknown
<220> FEATURE:
<223> OTHER INFORMATION: Description of Unknown Sequence:full-length CBir-1 Flagellin X from C3H/HeJ Bir mouse cecal bacteria genomic DNA random shear expression library PCR amplification

<400> SEQUENCE: 79

Val Val Gln His Asn Leu Arg Ala Met Asn Ser Asn Arg Met Leu Gly
5 10 15

Ile Thr Gln Gly Ser Leu Asn Lys Ser Thr Glu Lys Leu Ser Ser Gly
20 25 30

Tyr Lys Val Asn Arg Ala Ala Asp Asp Ala Ala Gly Leu Ser Ile Ser
35 40 45

Glu Lys Met Arg Lys Gln Ile Arg Gly Leu Ser Gln Ala Ser Leu Asn
50 55 60

Ala Glu Asp Gly Ile Ser Ala Val Gln Thr Ala Glu Gly Ala Leu Thr
65 70 75 80

Glu Val His Asp Met Leu Gln Arg Met Asn Glu Leu Ala Val Lys Ala
85 90 95

Ala Asn Gly Thr Asn Ser Thr Ser Asp Arg Gln Thr Ile Gln Asp Glu
100 105 110

Val Asp Gln Leu Leu Thr Glu Ile Asp Arg Val Ala Glu Thr Thr Lys
115 120 125

Phe Asn Glu Leu Tyr Thr Leu Lys Gly Asp Glu Asp Lys Val Thr Arg
130 135 140

Tyr Leu Ser Ala His Asp Ala Gly Ile Glu Gly Thr Leu Thr Gln Gly
145 150 155 160

Ala Thr Asn Ala Thr Phe Ser Met Asp Gln Leu Lys Phe Gly Asp Thr
165 170 175

Ile Met Ile Ala Gly Arg Glu Tyr His Ile Ser Gly Thr Lys Ala Glu
180 185 190

Gln Ala Ala Ile Ile Thr Ala Ser Val Lys Ile Gly Gln Gln Val Thr
195 200 205

Ile Asp Gly Ile Met Tyr Thr Cys Ser Ser Val Ser Asn Ala Asp Lys
210 215 220

Phe Glu Leu Lys Ser Glu Asp Leu Ile Ala Lys Leu Asp Thr Ser Ser
225 230 235 240

Leu Ser Ile Met Ser Val Asn Gly Lys Thr Tyr Tyr Gly Ala Gly Ile
245 250 255

Thr Asp Asp Arg Thr Val Val Ser Ser Ile Gly Ala Tyr Lys Leu Ile
260 265 270

Gln Lys Glu Leu Gly Leu Ala Ser Ser Ile Gly Ala Asp Gly Ala Thr
275 280 285

Gln Ala Ser Val Asn Ala Gly Val Asp Gly Lys Thr Leu Met Lys Pro
290 295 300

Ser Phe Glu Gly Lys Trp Val Phe Ser Ile Asp Lys Gly Ser Val Gln
305 310 315 320

Val Arg Glu Asp Ile Asp Phe Ser Leu His Val Gly Ala Asp Ala Asp
325 330 335

Met Asn Asn Lys Ile Ala Val Lys Ile Gly Ala Leu Asp Thr Lys Gly
340 345 350

Leu Gly Ile Gln Gly Leu Asn Val Lys Asp Thr Thr Gly Ala Ala Ala
355 360 365

Thr Tyr Ala Ile Asp Ser Ile Ala Asp Ala Val Ala Arg Ile Ser Ala
370 375 380

Gln Arg Ser Leu Leu Gly Ala Val Gln Asn Arg Leu Glu His Thr Ile
385 390 395 400

Asn Asn Leu Asp Asn Val Val Glu Asn Thr Thr Ala Ala Glu Ser Gln
405 410 415

Ile Arg Asp Thr Asp Met Ala Thr Glu Met Val Lys Tyr Ser Asn Asn
420 425 430

Asn Val Leu Ala Gln Ala Gly Gln Ser Met Leu Ala Gln Ser Asn Gln
435 440 445

Ala Asn Gln Gly Val Leu Gln Leu Leu Gln
450 455

<210> SEQ ID NO 80
<211> LENGTH: 149
<212> TYPE: PRT
<213> ORGANISM: Unknown
<220> FEATURE:
<223> OTHER INFORMATION: Description of Unknown Sequence:clone CBir-1 truncated Flagellin X amino terminal conserved end from C3H/HeJ Bir mouse cecal bacteria genomic DNA random shear expression library PCR amplification

<400> SEQUENCE: 80

Val Val Gln His Asn Leu Arg Ala Met Asn Ser Asn Arg Met Leu Gly
5 10 15

Ile Thr Gln Gly Ser Leu Asn Lys Ser Thr Glu Lys Leu Ser Ser Gly
20 25 30

Tyr Lys Val Asn Arg Ala Ala Asp Asp Ala Ala Gly Leu Ser Ile Ser
35 40 45

Glu Lys Met Arg Lys Gln Ile Arg Gly Leu Ser Gln Ala Ser Leu Asn
50 55 60

Ala Glu Asp Gly Ile Ser Ala Val Gln Thr Ala Glu Gly Ala Leu Thr
65 70 75 80

Glu Val His Asp Met Leu Gln Arg Met Asn Glu Leu Ala Val Lys Ala
85 90 95

Ala Asn Gly Thr Asn Ser Thr Ser Asp Arg Gln Thr Ile Gln Asp Glu
100 105 110

Val Asp Gln Leu Leu Thr Glu Ile Asp Arg Val Ala Glu Thr Thr Lys
115 120 125

Phe Asn Glu Leu Tyr Thr Leu Lys Gly Asp Glu Asp Lys Val Thr Arg
130 135 140

Tyr Leu Ser Ala His
145

<210> SEQ ID NO 81
<211> LENGTH: 329
<212> TYPE: PRT
<213> ORGANISM: Unknown
<220> FEATURE:
<223> OTHER INFORMATION: Description of Unknown Sequence:clone CBir-1 truncated Flagellin X amino terminal conserved end plus variable portion from C3H/HeJ Bir mouse cecal bacteria genomic DNA random shear expression library PCR amplification -continued

<400> SEQUENCE: 81

Val Val Gln His Asn Leu Arg Ala Met Asn Ser Asn Arg Met Leu Gly
5 10 15

Ile Thr Gln Gly Ser Leu Asn Lys Ser Thr Glu Lys Leu Ser Ser Gly
20 25 30

Tyr Lys Val Asn Arg Ala Ala Asp Asp Ala Ala Gly Leu Ser Ile Ser
35 40 45

Glu Lys Met Arg Lys Gln Ile Arg Gly Leu Ser Gln Ala Ser Leu Asn
50 55 60

Ala Glu Asp Gly Ile Ser Ala Val Gln Thr Ala Glu Gly Ala Leu Thr
65 70 75 80

Glu Val His Asp Met Leu Gln Arg Met Asn Glu Leu Ala Val Lys Ala
85 90 95

Ala Asn Gly Thr Asn Ser Thr Ser Asp Arg Gln Thr Ile Gln Asp Glu
100 105 110

Val Asp Gln Leu Leu Thr Glu Ile Asp Arg Val Ala Glu Thr Thr Lys
115 120 125

Phe Asn Glu Leu Tyr Thr Leu Lys Gly Asp Glu Asp Lys Val Thr Arg
130 135 140

Tyr Leu Ser Ala His Asp Ala Gly Ile Glu Gly Thr Leu Thr Gln Gly
145 150 155 160

Ala Thr Asn Ala Thr Phe Ser Met Asp Gln Leu Lys Phe Gly Asp Thr
165 170 175

Ile Met Ile Ala Gly Arg Glu Tyr His Ile Ser Gly Thr Lys Ala Glu
180 185 190

Gln Ala Ala Ile Ile Thr Ala Ser Val Lys Ile Gly Gln Gln Val Thr
195 200 205

Ile Asp Gly Ile Met Tyr Thr Cys Ser Ser Val Ser Asn Ala Asp Lys
210 215 220

Phe Glu Leu Lys Ser Glu Asp Leu Ile Ala Lys Leu Asp Thr Ser Ser
225 230 235 240

Leu Ser Ile Met Ser Val Asn Gly Lys Thr Tyr Tyr Gly Ala Gly Ile
245 250 255

Thr Asp Asp Arg Thr Val Val Ser Ser Ile Gly Ala Tyr Lys Leu Ile
260 265 270

Gln Lys Glu Leu Gly Leu Ala Ser Ser Ile Gly Ala Asp Gly Ala Thr
275 280 285

Gln Ala Ser Val Asn Ala Gly Val Asp Gly Lys Thr Leu Met Lys Pro
290 295 300

Ser Phe Glu Gly Lys Trp Val Phe Ser Ile Asp Lys Gly Ser Val Gln
305 310 315 320

Val Arg Glu Asp Ile Asp Phe Ser Leu
325

<210> SEQ ID NO 82
<211> LENGTH: 129
<212> TYPE: PRT
<213> ORGANISM: Unknown
<220> FEATURE:
<223> OTHER INFORMATION: Description of Unknown Sequence:clone CBir-1 truncated Flagellin X carboxy-terminal conserved end from C3H/HeJ Bir mouse cecal bacteria genomic DNA random shear expression library PCR amplification

<400> SEQUENCE: 82

Phe Ser Leu His Val Gly Ala Asp Ala Asp Met Asn Asn Lys Ile Ala

-continued

```
                5                   10                  15

Val Lys Ile Gly Ala Leu Asp Thr Lys Gly Leu Gly Ile Gln Gly Leu
            20                  25                  30

Asn Val Lys Asp Thr Thr Gly Ala Ala Ala Thr Tyr Ala Ile Asp Ser
        35                  40                  45

Ile Ala Asp Ala Val Ala Arg Ile Ser Ala Gln Arg Ser Leu Leu Gly
    50                  55                  60

Ala Val Gln Asn Arg Leu Glu His Thr Ile Asn Asn Leu Asp Asn Val
65                  70                  75                  80

Val Glu Asn Thr Thr Ala Ala Glu Ser Gln Ile Arg Asp Thr Asp Met
                85                  90                  95

Ala Thr Glu Met Val Lys Tyr Ser Asn Asn Asn Val Leu Ala Gln Ala
            100                 105                 110

Gly Gln Ser Met Leu Ala Gln Ser Asn Gln Ala Asn Gln Gly Val Leu
        115                 120                 125

Gln


<210> SEQ ID NO 83
<211> LENGTH: 1542
<212> TYPE: DNA
<213> ORGANISM: Helicobacter bilis
<220> FEATURE:
<223> OTHER INFORMATION: full-length flagellin B coding sequence

<400> SEQUENCE: 83

atgagtttta ggataaatac aaatatcgcg gcactcaatg cgcataccat cggtgtgcaa     60

aacaataggg caatagccaa ctcgttagag aagttaagct ctggtttgag gattaacaag    120

gcagcagatg atgcttcagg tatgtcaatc gcagatagtt tgcgtagcca agcaagttca    180

ttaggacagg caatcggcaa cgcaaatgat gcgattggta tgattcagat tgcggataaa    240

gcaatggatg agcagctaaa gattcttgat accgtaaagg ttaaagcaat ccaagcagct    300

caagatgggc aaactactga atcaagacgc gcgttgcaaa acgatattgt gcgactctta    360

gaagagcttg ataatatcgc caatacaaca agctataacg ggcagcaaat gctatctggt    420

gctttctcta acaaagagtt ccaaatcggt gcgtattcta atacaacagt gaaagcttca    480

atcggtccaa caagctcaga taaaatcgga catgtaagac ttgaaagctc atctgtaaca    540

ggtattggta tgcttgctag tgctggtgct aagaatctta aagaggtagc attgaaattc    600

cgccaagttg atggtaagaa agactacaag cttgagactg cagtcatttc tacaagtgct    660

ggcacaggta ttggtgtatt agcagatact atcaacaaat tctctgatac actcggtgtg    720

cgtgcgtatg caacggtgct tgggactggt ggtgtgccgg tgcaatctgg aacagtgcat    780

ggcttagttg taaatggcac aactattggg acaatcaatg atgtgcgtaa aaatgatgct    840

gatggtagat tgattaatgc ctttaactca attaaagaaa gaacaggtgt agaagcgtat    900

gtggatatcg aaggtagatt aaaccttaga agtcttgatg gtcgtgctat atctgtgcat    960

gctgaaggta aaacaggtgc ggtgcttggt ggcggtagct ttgctggagt atctgggaca   1020

aatcacgcta tcgtgggtcg tataagcctt gttaggacag atgcaagaga tattattgta   1080

tctgggacaa actttagtag tgttggtttc cactctgctc aaggtatcgc acaatacact   1140

gtgaatttgc gttctgttcg cggtaatatg gacgcaaata tcgcaagtgc aagcggtgca   1200

aacgcaaatg cggctcaagc ggtgcagaat aaagatggta tcggcgcagg tgttacttcg   1260

cttcgcggtg cgatggtcgt tatggatatg gcagaatctg ctacaagaca gcttgataaa   1320
```

```
atccgtgctg acatgggttc tgtgcaaatg cagcttgttg ctacaatcaa caacatttct   1380

atcacgcaag ttaatgttaa agcggctgaa agtcaaatta gagatgtgga tttcgcacaa   1440

gaatctgcga cattctctaa gcataacatc ttggctcaat ctggtagctt tgctatggct   1500

caagctaacg cagtgcaaca aaatgtctta agacttttgc aa                      1542


<210> SEQ ID NO 84
<211> LENGTH: 514
<212> TYPE: PRT
<213> ORGANISM: Helicobacter bilis
<220> FEATURE:
<223> OTHER INFORMATION: full-length flagellin B

<400> SEQUENCE: 84

Met Ser Phe Arg Ile Asn Thr Asn Ile Ala Ala Leu Asn Ala His Thr
1               5                   10                  15

Ile Gly Val Gln Asn Asn Arg Ala Ile Ala Asn Ser Leu Glu Lys Leu
            20                  25                  30

Ser Ser Gly Leu Arg Ile Asn Lys Ala Ala Asp Asp Ala Ser Gly Met
        35                  40                  45

Ser Ile Ala Asp Ser Leu Arg Ser Gln Ala Ser Ser Leu Gly Gln Ala
    50                  55                  60

Ile Gly Asn Ala Asn Asp Ala Ile Gly Met Ile Gln Ile Ala Asp Lys
65                  70                  75                  80

Ala Met Asp Glu Gln Leu Lys Ile Leu Asp Thr Val Lys Val Lys Ala
                85                  90                  95

Ile Gln Ala Ala Gln Asp Gly Gln Thr Thr Glu Ser Arg Arg Ala Leu
            100                 105                 110

Gln Asn Asp Ile Val Arg Leu Leu Glu Glu Leu Asp Asn Ile Ala Asn
        115                 120                 125

Thr Thr Ser Tyr Asn Gly Gln Gln Met Leu Ser Gly Ala Phe Ser Asn
    130                 135                 140

Lys Glu Phe Gln Ile Gly Ala Tyr Ser Asn Thr Thr Val Lys Ala Ser
145                 150                 155                 160

Ile Gly Pro Thr Ser Ser Asp Lys Ile Gly His Val Arg Leu Glu Ser
                165                 170                 175

Ser Ser Val Thr Gly Ile Gly Met Leu Ala Ser Ala Gly Ala Lys Asn
            180                 185                 190

Leu Lys Glu Val Ala Leu Lys Phe Arg Gln Val Asp Gly Lys Lys Asp
        195                 200                 205

Tyr Lys Leu Glu Thr Ala Val Ile Ser Thr Ser Ala Gly Thr Gly Ile
    210                 215                 220

Gly Val Leu Ala Asp Thr Ile Asn Lys Phe Ser Asp Thr Leu Gly Val
225                 230                 235                 240

Arg Ala Tyr Ala Thr Val Leu Gly Thr Gly Gly Val Pro Val Gln Ser
                245                 250                 255

Gly Thr Val His Gly Leu Val Val Asn Gly Thr Thr Ile Gly Thr Ile
            260                 265                 270

Asn Asp Val Arg Lys Asn Asp Ala Asp Gly Arg Leu Ile Asn Ala Phe
        275                 280                 285

Asn Ser Ile Lys Glu Arg Thr Gly Val Glu Ala Tyr Val Asp Ile Glu
    290                 295                 300

Gly Arg Leu Asn Leu Arg Ser Leu Asp Gly Arg Ala Ile Ser Val His
305                 310                 315                 320

Ala Glu Gly Lys Thr Gly Ala Val Leu Gly Gly Gly Ser Phe Ala Gly
```

```
                325                 330                 335

Val Ser Gly Thr Asn His Ala Ile Val Gly Arg Ile Ser Leu Val Arg
            340                 345                 350

Thr Asp Ala Arg Asp Ile Ile Val Ser Gly Thr Asn Phe Ser Ser Val
        355                 360                 365

Gly Phe His Ser Ala Gln Gly Ile Ala Gln Tyr Thr Val Asn Leu Arg
    370                 375                 380

Ser Val Arg Gly Asn Met Asp Ala Asn Ile Ala Ser Ala Ser Gly Ala
385                 390                 395                 400

Asn Ala Asn Ala Ala Gln Ala Val Gln Asn Lys Asp Gly Ile Gly Ala
                405                 410                 415

Gly Val Thr Ser Leu Arg Gly Ala Met Val Val Met Asp Met Ala Glu
            420                 425                 430

Ser Ala Thr Arg Gln Leu Asp Lys Ile Arg Ala Asp Met Gly Ser Val
        435                 440                 445

Gln Met Gln Leu Val Ala Thr Ile Asn Asn Ile Ser Ile Thr Gln Val
    450                 455                 460

Asn Val Lys Ala Ala Glu Ser Gln Ile Arg Asp Val Asp Phe Ala Gln
465                 470                 475                 480

Glu Ser Ala Thr Phe Ser Lys His Asn Ile Leu Ala Gln Ser Gly Ser
                485                 490                 495

Phe Ala Met Ala Gln Ala Asn Ala Val Gln Gln Asn Val Leu Arg Leu
            500                 505                 510

Leu Gln


<210> SEQ ID NO 85
<211> LENGTH: 1494
<212> TYPE: DNA
<213> ORGANISM: Unknown
<220> FEATURE:
<223> OTHER INFORMATION: Description of Unknown Sequence:full length
      CBir-1 flagellin from C3H/HeJ Bir mouse cecal bacteria genomic
      DNA random shear expression library PCR amplification

<400> SEQUENCE: 85

ggaggtatta ttatggtagt acagcacaat ttacaggcaa tgaactctaa cagaatgtta      60

ggcatcacac agaagacagc atctaagtct acagaaaagt tatcttcagg ttacgcaatc     120

aaccgcgcag cagacaacgc agcaggtctt gctatttctg agaagatgag aaagcagatc     180

agaggactta cacaggcttc tacaaatgct gaggacggca tcagctctgt acagacagca     240

gaaggcgctt tgacagaagt gcatgatatg cttcagagaa tgaacgagct ggcaattcag     300

gcagcaaacg gcacaaactc agaagatgac cgctcataca ttcaggacga aattgaccag     360

ctgacacagg aaatcgatcg tgttgctgag acaacaaagt tcaatgagac atatctcttg     420

aagggtgaca caaagaacgt tgacgctatg gactatacat atagctataa ggcagttaca     480

acgaatactg tagcaagagc ttcggtttta gcagcagaga acacagctac aggtatgtca     540

gttagtattt catttgctgc aaacagcggc aaggttactg cagctgactc taacaacctt     600

gcaaaggcta tcagagatca gggcttcaca atcacaacat ctacccagaa tggtaaggtt     660

gtttacggtc ttgagctgaa cggaagcgat gcaaaggcaa actatacagt ttcaacagta     720

agtatggaag ctggtacatt caagatcctg aattctaata agcaggttgt tgcatctgta     780

acaatatcta caacagctag ctttaaaaag gtatctggta tgtcacagat cgttacggcg     840

tactctgtat cagcagctta tgcgacgggt gatgtatact ctctctatga cgcagacgga     900
```

-continued

```
aatgcaattt cagcaaacaa gctggataag tactttacgg caggcggcgc tacagaggca    960

ggcggaatag ctactacact ttcagcaaac tctggtgtgc ctaaggttta tgacgtactc   1020

ggaaaagagg tttctgcagt aagcattgca agtactttag taacagcagt taaggataag   1080

acggctgcat tgaagatgaa cttccatgta ggtgctgacg gaacagataa caacaagatt   1140

aagatcaaca ttgaggctat gacagctaag agtcttggag ttaacggtct gaaggtgagc   1200

ggttcgagcg gaacaaacgc tacaaacgct atcgagataa tcgctggcgc tatcaagaag   1260

gtttctacac agagatctgc tcttggtgcg gttcagaaca gattagagca cacaatcaac   1320

aacttggata acatcgttga gaacacaaca gcagctgagt caggaatccg cgatacagat   1380

atggctacag agatggttaa gtactctaac gctaatatcc tttcacaggc aggtcagtct   1440

atgcttgcac agtctaacca gtctaaccag ggtgtacttc agctcttaca gtaa         1494
```

<210> SEQ ID NO 86
<211> LENGTH: 493
<212> TYPE: PRT
<213> ORGANISM: Unknown
<220> FEATURE:
<223> OTHER INFORMATION: Description of Unknown Sequence:full-length CBir-1 flagellin from C3H/HeJ Bir mouse cecal bacteria genomic DNA random shear expression library PCR amplification

<400> SEQUENCE: 86

```
Met Val Val Gln His Asn Leu Gln Ala Met Asn Ser Asn Arg Met Leu
                5                   10                  15

Gly Ile Thr Gln Lys Thr Ala Ser Lys Ser Thr Glu Lys Leu Ser Ser
            20                  25                  30

Gly Tyr Ala Ile Asn Arg Ala Ala Asp Asn Ala Ala Gly Leu Ala Ile
        35                  40                  45

Ser Glu Lys Met Arg Lys Gln Ile Arg Gly Leu Thr Gln Ala Ser Thr
    50                  55                  60

Asn Ala Glu Asp Gly Ile Ser Ser Val Gln Thr Ala Glu Gly Ala Leu
65                  70                  75                  80

Thr Glu Val His Asp Met Leu Gln Arg Met Asn Glu Leu Ala Ile Gln
                85                  90                  95

Ala Ala Asn Gly Thr Asn Ser Glu Asp Asp Arg Ser Tyr Ile Gln Asp
            100                 105                 110

Glu Ile Asp Gln Leu Thr Gln Glu Ile Asp Arg Val Ala Glu Thr Thr
        115                 120                 125

Lys Phe Asn Glu Thr Tyr Leu Leu Lys Gly Asp Thr Lys Asn Val Asp
    130                 135                 140

Ala Met Asp Tyr Thr Tyr Ser Tyr Lys Ala Val Thr Thr Asn Thr Val
145                 150                 155                 160

Ala Arg Ala Ser Val Leu Ala Ala Glu Asn Thr Ala Thr Gly Met Ser
                165                 170                 175

Val Ser Ile Ser Phe Ala Ala Asn Ser Gly Lys Val Thr Ala Ala Asp
            180                 185                 190

Ser Asn Asn Leu Ala Lys Ala Ile Arg Asp Gln Gly Phe Thr Ile Thr
        195                 200                 205

Thr Ser Thr Gln Asn Gly Lys Val Val Tyr Gly Leu Glu Leu Asn Gly
    210                 215                 220

Ser Asp Ala Lys Ala Asn Tyr Thr Val Ser Thr Val Ser Met Glu Ala
225                 230                 235                 240

Gly Thr Phe Lys Ile Leu Asn Ser Asn Lys Gln Val Val Ala Ser Val
                245                 250                 255
```

```
Thr Ile Ser Thr Thr Ala Ser Phe Lys Lys Val Ser Gly Met Ser Gln
            260                 265                 270

Ile Val Thr Ala Tyr Ser Val Ser Ala Ala Tyr Ala Thr Gly Asp Val
        275                 280                 285

Tyr Ser Leu Tyr Asp Ala Asp Gly Asn Ala Ile Ser Ala Asn Lys Leu
    290                 295                 300

Asp Lys Tyr Phe Thr Ala Gly Gly Ala Thr Glu Ala Gly Gly Ile Ala
305                 310                 315                 320

Thr Thr Leu Ser Ala Asn Ser Gly Val Pro Lys Val Tyr Asp Val Leu
                325                 330                 335

Gly Lys Glu Val Ser Ala Val Ser Ile Ala Ser Thr Leu Val Thr Ala
            340                 345                 350

Val Lys Asp Lys Thr Ala Ala Leu Lys Met Asn Phe His Val Gly Ala
        355                 360                 365

Asp Gly Thr Asp Asn Asn Lys Ile Lys Ile Asn Ile Glu Ala Met Thr
    370                 375                 380

Ala Lys Ser Leu Gly Val Asn Gly Leu Lys Val Ser Gly Ser Ser Gly
385                 390                 395                 400

Thr Asn Ala Thr Asn Ala Ile Glu Ile Ile Ala Gly Ala Ile Lys Lys
                405                 410                 415

Val Ser Thr Gln Arg Ser Ala Leu Gly Ala Val Gln Asn Arg Leu Glu
            420                 425                 430

His Thr Ile Asn Asn Leu Asp Asn Ile Val Glu Asn Thr Thr Ala Ala
        435                 440                 445

Glu Ser Gly Ile Arg Asp Thr Asp Met Ala Thr Glu Met Val Lys Tyr
    450                 455                 460

Ser Asn Ala Asn Ile Leu Ser Gln Ala Gly Gln Ser Met Leu Ala Gln
465                 470                 475                 480

Ser Asn Gln Ser Asn Gln Gly Val Leu Gln Leu Leu Gln
                485                 490


<210> SEQ ID NO 87
<211> LENGTH: 2019
<212> TYPE: DNA
<213> ORGANISM: Unknown
<220> FEATURE:
<223> OTHER INFORMATION: Description of Unknown Sequence:full-length
      Cbir-11 flagellin clone 76963 cDNA from C3H/HeJ Bir mouse cecal
      bacteria genomic DNA random shear expression library PCR
      amplification

<400> SEQUENCE: 87

gtgtgtggtc cacggcgcgg ccttcaccgg cggtgagcgc acggaccagg tgctggcgga     60

cttcaccgcc ccggaggacg gtcttctcca catcctctgc ctccacggcg acgtcttcag    120

ccaggacagc gtctacggcc ccatcacccg gccccagatc gcccgcagcg gcgcggatta    180

cctggccctg ggccacgtcc accagtgcag cggcatccag cgccaggggg acaccccctg    240

ggcctacccc ggctgtcccg agggccgggg gttcgacgag ctgggggaca agggtgtgct    300

ggcggggacg gtggatcggg gcggggcggc ggatctgcgc ttcgtgcccc tgtgccgccg    360

ccggtaccgg attctggagg cggacgtgac ggaccgggac cccggcgagg ccctggaggc    420

cgtgatcccc gccaccgccg ccatggacgt gtgccgcgtg ctcctcaccg gcgaaatcgg    480

ggagccgggc gcggatctgg cggacctgga gcgccggtac caggaccgct tctacgccct    540

ggagctccgg gaccgcaccc gggccgccca gaacctgtgg gcccgggccg gagaagactt    600
```

-continued

```
ccatggaaga gcggaagagg caaagaggaa gagcagcaag aataaccccg ttgagaagat    660

ggcgggtaag atgggtaagg aataggtaaa tatgcaggga tgcctaaggt tcctgcttat    720

tataaatagc caatccgcag ggcggggagg ctttgtggaa gccaatttgc acagcttggc    780

ttatcatgga aaagctgctg tgtgaagagg aaagagttaa aacatatatg tgcgcaaacg    840

gatttgcggc atggctgttg gcttgcaaag caagtggcag taacaggcct gctgaaggga    900

agccataaat aggcaggcat atcaaaaaca aggaggaaaa atattatggc aatggtaatc    960

caacacaatc ttacagcaat gaattctaac cgtcagttgg gagtaatcac tagcgggcag   1020

gcgaaatctt ctgaaaagtt gtcatctgga tataggatta atcgtgcagc agatgatgca   1080

gcagggttaa agatttctga gaaaatgagg agccaggttc gtggattgaa tagggcatcc   1140

acaaatgcac aggatggtat ctctttgatt cagacggcag aaggtgcgct gaatgaagca   1200

cattccatcc ttcagcgtat gcacgagttg gcagtccaag gtgcaaatga tacaaaccag   1260

gatattgacc gtgaggcgat agacgaggaa ttggctgcat taacccaaga acttgatagg   1320

atttctgaaa caacacagtt taataaacag aatctattgg atggaagttt tcaggataag   1380

aatctccatg taggtgcgaa tgcaaatcag aaaatcagca tcaagattga taatatggat   1440

gcagcggcgc ttgggttaaa agattttgca tactataaag gcacagaaac agtatcttat   1500

tctaaaatga catatatggg tgtaagttat acttatgata cgtcaaaaag tgatgcggca   1560

aatagaagtg cctttaaagc cctgttaaag tcagcaggga aagcagcatt tgtggatggg   1620

atgatagcac ttcattcaga tggaaagtat tatttgagtg atacaactac aaattatacc   1680

accctttcag cagcacgtgc aaacggtaag tctaagcttg gtatacaata tgctggtttg   1740

gcaagtgccc aatggtcttc tctgctgaaa aatgcaagaa aatcttcaac aacgataggg   1800

gcatttggaa gcaaagttac attctccagt cccactgttt cagattatga tagggcaaat   1860

gccacattgc aggcagttca ggcggctatt aatattgtat ctacacagcg ttctgcactt   1920

ggtgcaattc agaatcgttt agagcataca gtggcaaatc ttgataatgt agcagaaaat   1980

acacaggcag ctgaatctag gattcgtgac acggatatg                          2019
```

<210> SEQ ID NO 88
<211> LENGTH: 358
<212> TYPE: PRT
<213> ORGANISM: Unknown
<220> FEATURE:
<223> OTHER INFORMATION: Description of Unknown Sequence:predicted translated flagellin-like protein from Cbir-11 flagellin clone 76963 cDNA from C3H/HeJ Bir mouse cecal bacteria genomic DNA random shear expression library PCR amplification

<400> SEQUENCE: 88

```
Met Ala Met Val Ile Gln His Asn Leu Thr Ala Met Asn Ser Asn Arg
  1               5                  10                  15

Gln Leu Gly Val Ile Thr Ser Gly Gln Ala Lys Ser Ser Glu Lys Leu
             20                  25                  30

Ser Ser Gly Tyr Arg Ile Asn Arg Ala Ala Asp Asp Ala Ala Gly Leu
         35                  40                  45

Lys Ile Ser Glu Lys Met Arg Ser Gln Val Arg Gly Leu Asn Arg Ala
     50                  55                  60

Ser Thr Asn Ala Gln Asp Gly Ile Ser Leu Ile Gln Thr Ala Glu Gly
 65                  70                  75                  80

Ala Leu Asn Glu Ala His Ser Ile Leu Gln Arg Met His Glu Leu Ala
                 85                  90                  95
```

-continued

```
Val Gln Gly Ala Asn Asp Thr Asn Gln Asp Ile Asp Arg Glu Ala Ile
            100                 105                 110

Asp Glu Glu Leu Ala Ala Leu Thr Gln Glu Leu Asp Arg Ile Ser Glu
        115                 120                 125

Thr Thr Gln Phe Asn Lys Gln Asn Leu Leu Asp Gly Ser Phe Gln Asp
    130                 135                 140

Lys Asn Leu His Val Gly Ala Asn Ala Asn Gln Lys Ile Ser Ile Lys
145                 150                 155                 160

Ile Asp Asn Met Asp Ala Ala Ala Leu Gly Leu Lys Asp Phe Ala Tyr
                165                 170                 175

Tyr Lys Gly Thr Glu Thr Val Ser Tyr Ser Lys Met Thr Tyr Met Gly
            180                 185                 190

Val Ser Tyr Thr Tyr Asp Thr Ser Lys Ser Asp Ala Ala Asn Arg Ser
        195                 200                 205

Ala Phe Lys Ala Leu Leu Lys Ser Ala Gly Lys Ala Ala Phe Val Asp
    210                 215                 220

Gly Met Ile Ala Leu His Ser Asp Gly Lys Tyr Tyr Leu Ser Asp Thr
225                 230                 235                 240

Thr Thr Asn Tyr Thr Thr Leu Ser Ala Ala Arg Ala Asn Gly Lys Ser
                245                 250                 255

Lys Leu Gly Ile Gln Tyr Ala Gly Leu Ala Ser Ala Gln Trp Ser Ser
            260                 265                 270

Leu Leu Lys Asn Ala Arg Lys Ser Ser Thr Thr Ile Gly Ala Phe Gly
        275                 280                 285

Ser Lys Val Thr Phe Ser Ser Pro Thr Val Ser Asp Tyr Asp Arg Ala
    290                 295                 300

Asn Ala Thr Leu Gln Ala Val Gln Ala Ala Ile Asn Ile Val Ser Thr
305                 310                 315                 320

Gln Arg Ser Ala Leu Gly Ala Ile Gln Asn Arg Leu Glu His Thr Val
                325                 330                 335

Ala Asn Leu Asp Asn Val Ala Glu Asn Thr Gln Ala Ala Glu Ser Arg
            340                 345                 350

Ile Arg Asp Thr Asp Met
        355
```

<210> SEQ ID NO 89
<211> LENGTH: 227
<212> TYPE: PRT
<213> ORGANISM: Unknown
<220> FEATURE:
<223> OTHER INFORMATION: Description of Unknown Sequence:predicted translated phosphoesterase-like protein from Cbir-11 flagellin clone 76963 cDNA from C3H/HeJ Bir mouse cecal bacteria genomic DNA random shear expression library PCR amplification

<400> SEQUENCE: 89

```
Cys Val Val His Gly Ala Ala Phe Thr Gly Gly Glu Arg Thr Asp Gln
  1               5                  10                  15

Val Leu Ala Asp Phe Thr Ala Pro Glu Asp Gly Leu Leu His Ile Leu
             20                  25                  30

Cys Leu His Gly Asp Val Phe Ser Gln Asp Ser Val Tyr Gly Pro Ile
         35                  40                  45

Thr Arg Pro Gln Ile Ala Arg Ser Gly Ala Asp Tyr Leu Ala Leu Gly
     50                  55                  60

His Val His Gln Cys Ser Gly Ile Gln Arg Gln Gly Asp Thr Pro Trp
 65                  70                  75                  80
```

-continued

```
Ala Tyr Pro Gly Cys Pro Glu Gly Arg Gly Phe Asp Glu Leu Gly Asp
                85                  90                  95

Lys Gly Val Leu Ala Gly Thr Val Asp Arg Gly Gly Ala Ala Asp Leu
            100                 105                 110

Arg Phe Val Pro Leu Cys Arg Arg Arg Tyr Arg Ile Leu Glu Ala Asp
        115                 120                 125

Val Thr Asp Arg Asp Pro Gly Glu Ala Leu Glu Ala Val Ile Pro Ala
    130                 135                 140

Thr Ala Ala Met Asp Val Cys Arg Val Leu Leu Thr Gly Glu Ile Gly
145                 150                 155                 160

Glu Pro Gly Ala Asp Leu Ala Asp Leu Glu Arg Arg Tyr Gln Asp Arg
                165                 170                 175

Phe Tyr Ala Leu Glu Leu Arg Asp Arg Thr Arg Ala Ala Gln Asn Leu
            180                 185                 190

Trp Ala Arg Ala Gly Glu Asp Phe His Gly Arg Ala Glu Glu Ala Lys
        195                 200                 205

Arg Lys Ser Ser Lys Asn Asn Pro Val Glu Lys Met Ala Gly Lys Met
    210                 215                 220

Gly Lys Glu
225


<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence:six
      histidine purification tag

<400> SEQUENCE: 90

His His His His His His
  1               5
```